(12) United States Patent
Bradley et al.

(10) Patent No.: US 7,745,642 B2
(45) Date of Patent: Jun. 29, 2010

(54) GLYCINE TRANSPORT INHIBITORS

(75) Inventors: Daniel Marcus Bradley, Harlow (GB); Roderick Alan Porter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/718,333

(22) PCT Filed: Dec. 21, 2005

(86) PCT No.: PCT/GB2005/004951

§ 371 (c)(1),
(2), (4) Date: May 1, 2007

(87) PCT Pub. No.: WO2006/067423

PCT Pub. Date: Jun. 29, 2006

(65) Prior Publication Data

US 2008/0287547 A1    Nov. 20, 2008

(30) Foreign Application Priority Data

| Dec. 23, 2004 | (GB) | .................................. 0428231.5 |
| May 5, 2005 | (GB) | .................................. 0509204.4 |
| Nov. 29, 2005 | (GB) | .................................. 0524320.9 |

(51) Int. Cl.
C07C 233/78   (2006.01)
C07C 211/36   (2006.01)

(52) U.S. Cl. ....................... 548/568; 548/566; 548/567; 564/175

(58) Field of Classification Search ........................ None
See application file for complete search history.

(56) References Cited

U.S. PATENT DOCUMENTS

| 2,746,959 | A | 5/1956 | Bruce et al. ............... 260/239.1 |
| 3,145,209 | A | 8/1964 | Krapcho ..................... 260/268 |
| 5,194,644 | A | 3/1993 | Brunner et al. ............. 556/137 |
| 2005/0267152 | A1 * | 12/2005 | Bloomfield et al. ......... 514/319 |

FOREIGN PATENT DOCUMENTS

| FR | 2861073 | 10/2003 |
| GB | 1410011 | 10/1975 |
| WO | WO 99/44596 | 9/1999 |
| WO | WO 01/81308 | 11/2001 |
| WO | WO 03/010132 | 2/2003 |
| WO | WO 03/055478 | 7/2003 |
| WO | WO 2004/072034 | 8/2004 |
| WO | WO 2004/098589 | 11/2004 |
| WO | WO 2005/023260 | 3/2005 |
| WO | WO 2005/037782 | 4/2005 |
| WO | WO 2005/037785 | 4/2005 |
| WO | WO 2005/095343 | 10/2005 |
| WO | WO 2005/103042 | 11/2005 |
| WO | WO 2005/110983 | 11/2005 |
| WO | WO 2006/067414 | 6/2006 |
| WO | WO 2006/067417 | 6/2006 |
| WO | WO 2006/067423 | 6/2006 |
| WO | WO 2007/147831 | 12/2007 |

OTHER PUBLICATIONS

Adams et al. J. Org. Chem. 1998, 63, p. 9932-9934.*
Javitt, Biol. Psychiatry 2008, 63, p. 6-8.*
A Viso et al, Highly diatereoselective [3+2]cycloadditions between nonracemic p-Tolylsulfinimines and iminoesters: An efficient entry to enantiopure imidazolidines and vicinal diaminoalcohol; Chem. Eur. J, 2003, vol. 9, p. 2867-2876.
P N Becker et al, A New Method for 1,2-Diamination of Alkenes Using Cyclopentadienylnitrosylcobalt Dimer/NO/LiAlH4; J. Am Chem. Soc., 1980, vol. 102, p5676-5677.
Kindai Chemical Industry Co, Japan; Chemical abstract: "Sizing of Paper"; Chemical abstracts service (online), 1982.
Sandra M Lechner, Elsevier Limited, Glutamate-based therapeutic approaches: inhibitors of glycine transport; Current Opinion in Pharmacology, Dec. 22, 2005, vol. 6, p75-81.
Basolo F et al, Steric effects and the stability of complex compounds. IV. The chelating tendencies of C-substituted ethylenediamines with copper (II) and nickel (II) ions; J. Am. Chem. Soc., 1954, vol. 76, p. 956-959.
Sunil A. Pansare, Stereoselective synthesis of 3,4-disubstituted 1,2,5-thiadiazolidine 1,1, dioxides and their conversion to unsymmetrical vicinal diamines; Synlett, 1998, vol. 6, p. 623-624.
Hayden T Revert et al, Radiosynthesis of a ligand for studying the glycine transporter, Journal of Labelled Compounds and Radiopharmaceuticals, 2001, vol. 44, p241-246.

* cited by examiner

*Primary Examiner*—Daniel M Sullivan
*Assistant Examiner*—Yevegeny Velenrod
(74) *Attorney, Agent, or Firm*—James M. Kanagy; Edward R. Gimmi; Charles M. Kinzig

(57) ABSTRACT

The present invention relates to compounds of formula (I), or to salts or solvates thereof, their use in the manufacture of medicaments for treating neurological and neuropsychiatric disorders, in particular psychoses, dementia or attention deficit disorder. The invention further comprises processes to make these compounds and pharmaceutical formulations thereof.

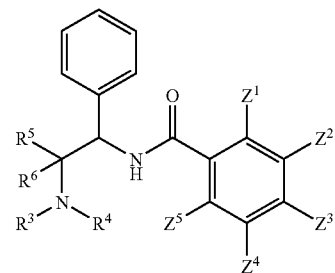

13 Claims, No Drawings

GLYCINE TRANSPORT INHIBITORS

This application is a 35 U.S.C. 371 application, which claims the benefit of Provisional Application No. GB0428231.5, filed 23 Dec. 2004.

The present invention relates to glycine transporter inhibiting compounds, their use in the manufacture of medicaments for treating neurological and neuropsychiatric disorders, in particular psychoses, dementia or attention deficit disorder. The invention further comprises processes to make these compounds and pharmaceutical formulations thereof.

Molecular cloning has revealed the existence in mammalian brains of two classes of glycine transporters, termed GlyT1 and GlyT2. GlyT1 is found predominantly in the forebrain and its distribution corresponds to that of glutamatergic pathways and NMDA receptors (Smith, et al., Neuron, 8, 1992: 927-935). Molecular cloning has further revealed the existence of three variants of GlyT1, termed GlyT-1a, GlyT-1b and GlyT-1c (Kim et al., Molecular Pharmacology, 45, 1994: 608-617), each of which displays a unique distribution in the brain and peripheral tissues. The variants arise by differential splicing and exon usage, and differ in their N-terminal regions. GlyT2, in contrast, is found predominantly in the brain stem and spinal cord, and its distribution corresponds closely to that of strychnine-sensitive glycine receptors (Liu et al., J. Biological Chemistry, 268, 1993: 22802-22808; Jursky and Nelson, J. Neurochemistry, 64, 1995: 1026-1033). Another distinguishing feature of glycine transport mediated by GlyT2 is that it is not inhibited by sarcosine as is the case for glycine transport mediated by GlyT1. These data are consistent with the view that, by regulating the synaptic levels of glycine, GlyT1 and GlyT2 selectively influence the activity of NMDA receptors and strychnine-sensitive glycine receptors, respectively.

NMDA receptors are critically involved in memory and learning (Rison and Staunton, *Neurosci. Biobehav. Rev.*, 19 533-552 (1995); Danysz et al, *Behavioral Pharmacol.*, 6 455-474 (1995)); and, furthermore, decreased function of NMDA-mediated neurotransmission appears to underlie, or contribute to, the symptoms of schizophrenia (Olney and Farber, *Archives General Psychiatry*, 52, 998-1007 (1996). Thus, agents that inhibit GlyT1 and thereby increase glycine activation of NMDA receptors can be used as novel antipsychotics and anti-dementia agents, and to treat other diseases in which cognitive processes are impaired, such as attention deficit disorders and organic brain syndromes. Conversely, over-activation of NMDA receptors has been implicated in a number of disease states, in particular the neuronal death associated with stroke and possibly neurodegenerative diseases, such as Alzheimer's disease, multi-infarct dementia, AIDS dementia, Huntington's disease, Parkinson's disease, amyotrophic lateral sclerosis or other conditions in which neuronal cell death occurs, such as stroke or head trauma. Coyle & Putffarcken, *Science*, 262, 689-695 (1993); Lipton and Rosenberg, *New Engl. J. of Medicine*, 330, 613-622 (1993); Choi, *Neuron*, 1, 623-634 (1988). Thus, pharmacological agents that increase the activity of GlyT1 will result in decreased glycine-activation of NMDA receptors, which activity can be used to treat these and related disease states. Similarly, drugs that directly block the glycine site of the NMDA receptors can be used to treat these and related disease states.

Glycine transport inhibitors are already known in the art, for example as disclosed in published international patent application WO03/055478 (SmithKline Beecham).

However, there still remains the need to identify further compounds that can inhibit GlyT1 transporters, including those that inhibit GlyT1 transporters selectively over GlyT2 transporters.

It has now been found that a novel class of compounds inhibit GlyT1 transporters and are thus useful in the treatment of certain neurological and neuropsychiatric disorders, including schizophrenia.

Thus, in a first aspect, there is provided a compound of formula (I) or a salt or solvate thereof:

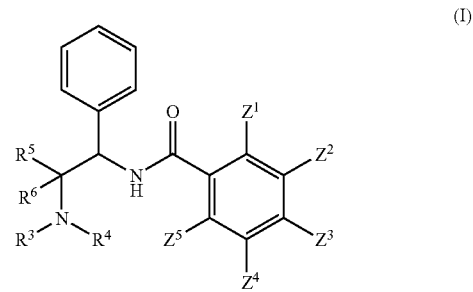

(I)

wherein $Z^1$ is selected from the group consisting of $C_{1-4}$alkyl, $C_{3-6}$cycloalkyl, $C_{1-4}$alkoxy, $C_{1-4}$alkylthio, halo$C_{1-4}$alkyl, phenyl, halo$C_{1-4}$alkoxy, halophenyl, $C_{1-4}$alkylsulfoxy, $C_{1-4}$alkylsulfonyl, bromo and chloro;

$Z^2$ is selected from the group consisting of hydrogen, halogen, cyano, $C_{1-4}$alkyl, phenyl, halo$C_{1-4}$alkyl, halo$C_{1-4}$alkoxy, halophenyl, $C_{1-4}$alkoxy$C_{1-4}$alkyl and $C_{3-6}$cycloalkyl;

$Z^3$ is selected from the group consisting of hydrogen, halogen, $C_{1-4}$alkyl, $C_{1-4}$alkoxy, $C_{1-4}$alkylthio, halo$C_{1-4}$alkyl, halo$C_{1-4}$alkoxy, and $C_{3-6}$cycloalkyl;

$Z^4$ is selected from the group consisting of hydrogen, halogen, $C_{1-3}$alkyl, halo$C_{1-4}$alkyl, $C_{1-4}$alkoxy, $C_{1-4}$alkylthio, phenyl, halo$C_{1-4}$alkoxy, halophenyl, $C_{1-4}$alkoxy$C_{1-4}$alkyl and $C_{3-6}$cycloalkyl;

$Z^5$ is selected from the group consisting of hydrogen, fluoro, chloro, bromo, iodo, hydroxy, $C_{1-4}$alkyl, $C_{1-4}$alkoxy, $C_{1-4}$alkylthio, phenyl, halo$C_{1-4}$alkyl, halo$C_{1-4}$alkoxy, halophenyl, $C_{1-4}$alkoxy$C_{1-4}$alkyl and $C_{3-6}$cycloalkyl;

whereby if more than one of $Z^1$ to $Z^5$ is methoxy, then only $Z^1$ and $Z^5$ are methoxy $R^3$ and $R^4$ are independently selected from hydrogen and $C_{1-4}$alkyl, optionally substituted with one or more groups Y; or $R^3$ and $R^4$ together with the nitrogen atom to which they are attached form a saturated or partially unsaturated 4-, 5-6- or 7-membered carbocyclic ring optionally substituted with a group Y';

Y is selected from the group consisting of $C_{1-4}$alkoxy, hydroxy, halo$C_{1-4}$alkoxy and $C_{3-5}$cycloalkyl;

Y' is selected from the group consisting of $C_{1-4}$alkyl, $C_{1-4}$alkoxy, halogen, hydroxy, halo$C_{1-4}$alkoxy, $C_{3-5}$cycloalkyl and $C_{5-10}$aryl or Y' forms a —$CH_2$— or —$CH_2$—$CH_2$— bridge between two atoms on the 4-, 5-, 6-, or 7-membered carbocyclic ring;

$R^5$ and $R^6$ are independently $C_{1-4}$alkyl, optionally substituted with one or more groups X; or $R^5$ and $R^6$ together with the carbon atom to which they are attached form a saturated 5- or 6-membered carbocyclic ring optionally substituted with one or more groups X', in the case of $R^5$ and $R^6$ together with the carbon atom to which they are attached forming a 5-membered saturated carbocyclic ring, that ring may optionally further comprise an additional heteroatom group selected from O, N and $S(O)_m$; where m=0, 1 or 2.

X is selected from the group consisting of halogen, hydroxy, $C_{1-4}$alkoxy, halo$C_{1-4}$alkyl, halo$C_{1-4}$alkoxy and $C_{5-10}$aryl; and X' is selected from the group consisting of halogen, hydroxy, $C_{1-4}$alkyl, $C_{1-4}$alkoxy, halo$C_{1-4}$alkyl, halo$C_{1-4}$alkoxy and $C_{5-10}$aryl;

whereby $R^3$, $R^4$, $R^5$ and $R^6$ are not all simultaneously unsubstituted methyl;

with the provisos that when simultaneously Z1 is propyloxy, Z3 is chloro, Z2=Z4=Z5=H, and R5 and R6 are both methyl, then $R^3$ and $R^4$ together with the nitrogen atom to which they are attached do not form a 2-methylpyrrolidine group;

when simultaneously Z1 is methyl, Z3 is methoxy, Z2=Z4=Z5=H, and R5 and R6 are both methyl, then $R^3$ and $R^4$ together with the nitrogen atom to which they are attached do not form a pyrrolidine group.

As used herein, the term "alkyl" refers to a straight or branched alkyl group in all isomeric forms. Examples of $C_{1-4}$alkyl include methyl, ethyl, propyl, isopropyl, butyl, isobutyl, sec-butyl and tert-butyl.

As used herein, the term "cycloalkyl" refers to a non-aromatic cyclic saturated hydrocarbon ring. Examples of $C_{3-6}$cycloalkyl include cyclopropyl, cyclobutyl, cyclopentyl, and cyclohexyl.

As used herein, the term "alkoxy" refers to the group —O-alkyl wherein alkyl is as defined above. The term "methoxy" refers to the group —O-methyl.

As used herein, the term "alkylthio" refers to the group —S-alkyl wherein alkyl is as defined above. The term "methylthio" refers to the group —S-methyl.

As used herein, the term "alkylsulfoxy" refers to the group —S(O)-alkyl wherein alkyl is as defined above.

As used herein, the term "alkysulfonyl" refers to the group —S(O)$_2$-alkyl wherein alkyl is as defined above.

As used herein, the term "$C_{5-10}$aryl" refers to a 5- or 6-membered monocyclic aromatic group or a 8- to 10-membered bicyclic aromatic group. Examples of $C_{5-10}$aryl include phenyl, indenyl, azulenyl and naphthyl.

As used herein, the terms "halogen" and its abbreviation "hal" refer to fluorine, chlorine, bromine, or iodine.

As used herein, the term "haloalkyl" refers to an alkyl group as defined above which is substituted with any number of fluorine, chlorine, bromine, or iodine atoms, including with mixtures of those atoms. A haloalkyl group may, for example contain 1, 2 or 3 halogen atoms. For example, a haloalkyl group may have all hydrogen atoms replaced with halogen atoms. Examples of haloalkyl groups include fluoromethyl, difluoromethyl and trifluoromethyl.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations. The salts may have any suitable stoichiometry. For example, a salt may have 1:1 or 2:1 stoichiometry. Non-integral stoichiometry ratios are also possible.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

In one embodiment, $R^3$ and $R^4$ are both simultaneously the same $C_{1-4}$alkyl, the same $C_{1-4}$alkyl substituted with one or more groups Y, or $R^3$ and $R^4$ together with the nitrogen atom to which they are attached form a saturated 5- or 6-membered carbocyclic ring optionally substituted with a group Y'.

In one embodiment, $R^3$ and $R^4$ are both $C_{1-4}$alkyl, for example methyl or ethyl, for example methyl.

Y may, for example, be selected from the group consisting of $C_{1-4}$alkoxy, halo$C_{1-4}$alkoxy and $C_{5-10}$aryl. In one embodiment, Y is selected from the group consisting of $C_{1-4}$alkoxy, $C_{5-10}$aryl.

Y' may, for example, be selected from the group consisting of halogen, $C_{1-4}$alkyl, $C_{1-4}$alkoxy, halo$C_{1-4}$alkoxy and $C_{5-10}$aryl. In one embodiment, Y' is selected from the group consisting of $C_{1-4}$alkyl, $C_{1-4}$alkoxy, $C_{5-10}$aryl.

In one embodiment, $R^3$ and $R^4$ are independently selected from hydrogen, methyl and ethyl, optionally substituted with a group Y, or $R^3$ and $R^4$ together with the nitrogen atom to which they are attached form a saturated or partially unsaturated (for example saturated) 4-, 5-, 6- or 7-membered carbocyclic ring optionally substituted with a group Y'.

In a further embodiment, $R^3$ and $R^4$ are selected from methyl and ethyl, optionally substituted with a group Y, or $R^3$ and $R^4$ together with the nitrogen atom to which they are attached form a saturated 4-, 5- or 6-membered carbocyclic ring optionally substituted with a group Y'. For example, $R^3$ and $R^4$ are both unsubstituted methyl, or $R^3$ and $R^4$ together with the nitrogen atom to which they are attached form a saturated 5- or 6-membered carbocyclic ring.

Y may, for example, be selected from the group consisting of $C_{1-4}$alkoxy, hydroxy and $C_{3-5}$cycloalkyl.

Y' may, for example, be selected from the group consisting of halogen and $C_{1-4}$alkyl or Y' may form a —CH$_2$— bridge between two atoms on the 5- or 6-membered carbocyclic ring.

In one embodiment, $R^5$ and $R^6$ are both simultaneously the same $C_{1-4}$alkyl, the same $C_{1-4}$alkyl substituted with one or more groups X, or $R^5$ and $R^6$ together with the carbon atom to which they are attached form a saturated 5- or 6-membered carbocyclic ring optionally substituted with a group X', the 5- or 6-membered saturated carbocyclic ring optionally further comprising an additional heteroatom group selected from O, N and $S(O)_m$ (where m is 0, 1, or 2);

In a further embodiment, $R^5$ and $R^6$ together with the carbon atom to which they are attached form a saturated 5- or 6-membered carbocyclic ring, for example a 5-membered carbocyclic ring.

X is, for example, selected from the group consisting of halogen, $C_{1-4}$alkoxy, halo$C_{1-4}$alkyl, halo$C_{1-4}$alkoxy and $C_{5-10}$aryl.

In one embodiment, $R^5$ and $R^6$ are independently selected from methyl and ethyl, optionally substituted with one or more groups X; or $R^5$ and $R^6$ together with the carbon atom to which they are attached form a saturated 5- or 6-membered carbocyclic ring and in the case of $R^5$ and $R^6$ together with the carbon atom to which they are attached forming a 5-membered saturated carbocyclic ring, that ring may optionally further comprise an oxygen heteroatom. In one embodiment one of $R^5$ and $R^6$ is ethyl and the other is methyl.

For example, in one embodiment $R^5$ and $R^6$ are independently selected from methyl and ethyl, or $R^5$ and $R^6$ together with the carbon atom to which they are attached form a saturated 5-membered carbocyclic ring. For example, in a further embodiment, $R^5$ and $R^6$ are both methyl, or $R^5$ and $R^6$ together with the carbon atom to which they are attached form a saturated 5-membered carbocyclic ring.

X may, for example, be selected from the group consisting of hydroxy and $C_{1-4}$alkoxy.

X' may, for example, be selected from the group consisting of hydroxy and $C_{1-4}$alkoxy.

In one embodiment, at least one of the pairs of groups $R^3/R^4$ and $R^5/R^6$ forms a cyclic group with the Nitrogen or Carbon atom to which they are respectively attached. For example, that cyclic group may be a 5-membered carbocyclic ring.

In one embodiment of the invention, $Z^1$ is selected from the group consisting of chloro, $C_{1-4}$alkyl, halo$C_{1-4}$alkyl, $C_{1-4}$alkoxy, halo$C_{1-4}$alkoxy, $C_{1-4}$alkylthio, phenyl, and halophenyl;

$Z^2$ is selected from the group consisting of hydrogen, iodo, bromo, chloro, fluoro, $C_{1-4}$alkyl, halo$C_{1-4}$alkyl, halo $C_{1-4}$alkoxy, phenyl, and halophenyl;

$Z^3$ is selected from the group consisting of hydrogen, iodo, bromo, chloro, $C_{1-4}$alkyl, halo$C_{1-4}$alkyl, $C_{1-4}$alkoxy, halo $C_{1-4}$alkoxy;

$Z^4$ is selected from the group consisting of hydrogen, iodo, bromo, chloro, fluoro, $C_{1-4}$alkoxy, halo$C_{1-4}$alkoxy, phenyl, and halophenyl; and $Z^5$ is selected from the group consisting of hydrogen, iodo, bromo, chloro, $C_{1-4}$alkyl, $C_{1-4}$alkoxy, halo$C_{1-4}$alkoxy, phenyl, and halophenyl;

wherein no more than three of $Z^1$, $Z^2$, $Z^3$, $Z^4$, and $Z^5$ are hydrogen.

In another embodiment, $Z^1$ is selected from the group consisting of chloro, halo$C_{1-4}$alkyl, $C_{1-4}$alkoxy, halo$C_{1-4}$alkoxy, phenyl, and halophenyl, and $Z^2$, $Z^3$, $Z^4$ and $Z^5$ are hydrogen.

In a further embodiment, $Z^1$ is selected from the group consisting of, chloro, $C_{1-4}$alkyl, and $C_{1-4}$alkoxy;

$Z^2$ is selected from the group consisting of hydrogen, halo$C_{1-4}$alkyl, and $C_{1-4}$alkyl;

$Z^3$ is hydrogen;

$Z^4$ is hydrogen; and $Z^5$ is selected from the group consisting of hydrogen, and $C_{1-4}$alkyl;

wherein no more than three of $Z^1$, $Z^2$, $Z^3$, $Z^4$, and $Z^5$ are hydrogen.

In one embodiment, $Z^1$ is selected from the group consisting of $C_{1-4}$alkyl, $C_{3-6}$cycloalkyl, $C_{1-2}$alkoxy, $C_{1-4}$alkylthio, halo$C_{1-4}$alkyl, phenyl, halo$C_{1-4}$alkoxy, halophenyl, $C_{1-4}$alkylsulfoxy, $C_{1-4}$alkylsulfonyl, bromo and chloro.

In one embodiment, $Z^1$ is selected from the group consisting of $C_{1-4}$alkyl, $C_{1-2}$alkoxy, $C_{1-4}$alkylthio, halo$C_{1-4}$alkyl, phenyl, halo$C_{1-4}$alkoxy, halophenyl and chloro;

For example, $Z^1$ is selected from the group consisting of $C_{1-4}$alkyl, $C_{1-2}$alkoxy, $C_{1-4}$alkylthio, halo$C_{1-4}$alkyl, and chloro, particularly from the group consisting of $C_{1-4}$alkyl and $C_{1-2}$alkoxy. For example, $Z^1$ may be selected from methyl, methylthio, ethoxy and methoxy.

In one embodiment, $Z^2$ is selected from the group consisting of hydrogen, halogen, $C_{1-4}$alkyl, phenyl and halo $C_{1-4}$alkyl. For example, $Z^2$ may be selected from the group consisting of hydrogen, halogen, and $C_{1-4}$alkyl. For example $Z^2$ may be selected from hydrogen, bromo and methyl. For example $Z^2$ may be hydrogen In one embodiment, $Z^3$ is selected from the group consisting of hydrogen, halogen, $C_{1-4}$alkyl, $C_{1-4}$alkoxy and halo $C_{1-4}$alkyl. For example, $Z^3$ may be selected from the group consisting of hydrogen, halogen, $C_{1-4}$alkyl and halo $C_{1-4}$alkyl. For example $Z^3$ may be selected from hydrogen, fluoro, chloro and trifluoromethyl.

In one embodiment, $Z^4$ is selected from the group consisting of hydrogen, halogen, $C_{1-3}$alkyl, phenyl, $C_{1-4}$alkoxy and halo$C_{1-4}$alkyl. For example $Z^4$ may be selected from the group consisting of hydrogen and halogen. For example $Z^4$ may be hydrogen.

In one embodiment, $Z^5$ is selected from the group consisting of hydrogen, hydroxy, fluoro, chloro, bromo, $C_{1-4}$alkyl, $C_{1-4}$alkoxy, halo$C_{1-4}$alkyl and halo$C_{1-4}$alkoxy; $Z^5$ may be selected from the group consisting of chloro, bromo, $C_{1-4}$alkyl, $C_{1-4}$alkoxy and halo$C_{1-4}$alkyl. For example, $Z^5$ may be selected from the group consisting of bromo, methyl, and trifluoromethyl.

In one embodiment, $Z^1$ and $Z^5$ are both simultaneously not hydrogen. In a further embodiment, $Z^1$, $Z^3$ and $Z^5$ are all simultaneously not hydrogen.

Accordingly, in one embodiment, the present invention provides a compound of formula (Ia) or a salt or solvate thereof:

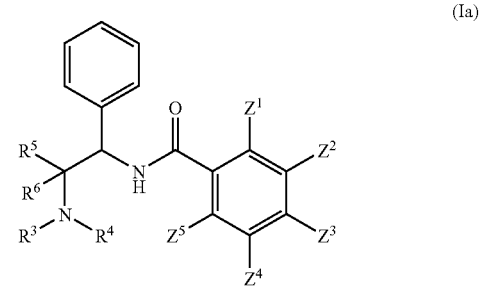

(Ia)

wherein $Z^1$ is selected from the group consisting of $C_{1-4}$alkyl, $C_{1-2}$alkoxy, $C_{1-4}$alkylthio, halo$C_{1-4}$alkyl, and chloro;

$Z^2$ is selected from the group consisting of hydrogen, halogen, halo$C_{1-4}$alkyl, and $C_{1-4}$alkyl;

$Z^3$ is selected from the group consisting of hydrogen, halogen, halo$C_{1-4}$alkyl and $C_{1-4}$alkyl;

$Z^4$ is selected from the group consisting of hydrogen and halogen;

$Z^5$ is selected from the group consisting of bromo, $C_{1-4}$alkyl, $C_{1-4}$alkoxy and halo$C_{1-4}$alkyl;

$R^3$ and $R^4$ are independently unsubstituted methyl or ethyl, or $R^3$ and $R^4$ together with the nitrogen atom to which they are attached form a saturated 5- or 6-membered carbocyclic ring;

$R^5$ and $R^6$ are independently methyl or ethyl, or $R^5$ and $R^6$ together with the carbon atom to which they are attached form a saturated 5-membered carbocyclic ring;

and at least one of the pairs of groups $R^3/R^4$ and $R^5/R^6$ forms a cyclic group with the Nitrogen or Carbon atom to which they are respectively attached.

It is to be understood that features of an embodiment of the invention described with reference to one parameter can be combined with the features of another embodiment. The disclosure herein thus includes the combination of the features of any one embodiment with the features of any other embodiment described. All embodiments and features of compounds of formula (I) apply to compounds of formula (Ia).

Examples of compounds of the invention include Examples 1 to 260 shown below, as well as salts and solvates thereof.

The compounds of formula (I) may have the ability to crystallise in more than one form. This is a characteristic known as polymorphism, and it is understood that such polymorphic forms ("polymorphs") are within the scope of formula (I). Polymorphism generally can occur as a response to changes in temperature or pressure or both and can also result from variations in the crystallisation process. Polymorphs can be distinguished by various physical characteristics known in the art such as x-ray diffraction patterns, solubility, and melting point.

Certain of the compounds described herein may exist in stereoisomeric forms (i.e. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

As referred to above, individual enantiomers of compounds of formula (I) may be prepared. In a preferred embodiment, an optically pure enantiomer is desired. The term "optically pure enantiomer" means that the compound contains greater than about 90% of the desired isomer by weight, preferably greater than about 95% of the desired isomer by weight, and most preferably greater than about 99% of the desired isomer by weight, said weight percent based upon the total weight of the isomer(s) of the compound. In some cases, one enantiomer of a particular structure may have a significantly higher activity than the other enantiomer of the same structure. Chirally pure, or chirally enriched compounds may be prepared by chirally selective synthesis or by separation of enantiomers. The separation of enantiomers may be carried out on the final product or, alternatively on a suitable intermediate.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of general formula (I) may be prepared by methods known in the art of organic synthesis as set forth in part by the following synthesis schemes. It is also recognised that in all of the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognise if a stereocentre exists in compounds of formula (I). Accordingly, the present invention includes both possible stereoisomers and includes not only racemic compounds but the individual enantiomers as well. Where the stereochemistry is indicated as being variable at certain positions, a mixture of stereoisomers may be obtained, this mixture having been separated where indicated. Stereoisomers may be separated by high-performance liquid chromatography or other appropriate means. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Typical reaction routes for the preparation of a compound of formula (I) as hereinbefore defined, are shown in the following schemes. The starting materials and reagents are known to the skilled person in the art and/or can be prepared using methods known in the art.

Compounds of formula (I) can be synthesised by known methods; for example by, but not limited to, the synthetic route outlined in the scheme below

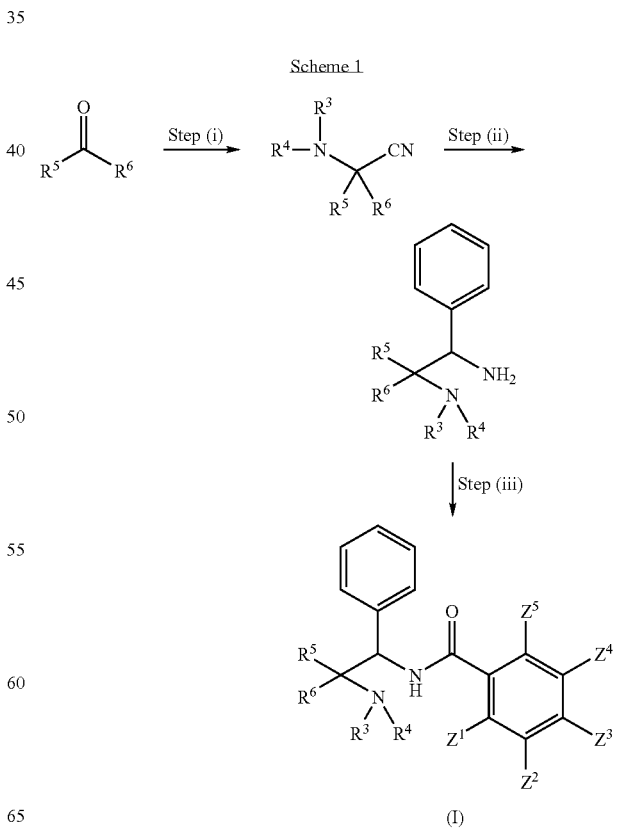

wherein $R^3$, $R^4$, $R^5$, $R^6$, $Z^1$, $Z^2$, $Z^3$, $Z^4$ and $Z^5$ are as defined for the compound of formula (I).

Step (i) is carried out for example by reaction of a ketone with an amine or amine salt in the presence of inorganic cyanide, for example potassium cyanide, in solvent such as water or by reaction of a ketone with an amine and trimethylsilyl cyanide in either the absence of solvent or in a solvent such as acetic acid.

Step (ii) can be achieved by successive reaction with an appropriate organometallic reagent, for example phenyllithium, in a suitable inert solvent for example tetrahydrofuran, followed by reduction with a reducing agent, for example, sodium borohydride in a suitable solvent, for example methanol.

Acylation step (iii) can be achieved by reaction with a compound of formula (III):

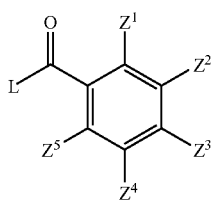

(III)

wherein $Z^1$, $Z^2$, $Z^3$, $Z^4$ and $Z^5$ are as defined in formula (I) and L represents a suitable leaving group. Examples of leaving groups include halogen, hydroxy, OC(=O)alkyl, OC(=O)O-alkyl and $OSO_2Me$. L may be halogen and acylation in step (iii) may be carried out in an inert solvent such as dichloromethane, in the presence of a base such as triethylamine. When L represents hydroxy, the reaction preferably takes place in an inert solvent such as dichloromethane in the presence of a coupling reagent, for example a diimide reagent such as N,N dicyclohexylcarbodiimide (DCC), N-(3-(dimethylamino)propyl)-N-ethylcarbodiimide hydrochloride (EDC), polymer-supported EDC, polymer-supported DCC or O-(7-azabenzotriazol-1-yl)-1,1,3,3-tetramethyluronium hexafluoro phosphate (HATU).

Within the scheme there is scope to convert a group $R^3$ into another group $R^3$ and similarly for groups $R^4$, $R^5$ and $R^6$, and $Z^1$, $Z^2$, $Z^3$, $Z^4$ and $Z^5$.

Accordingly, in a second aspect, the present invention provides a method of preparing a compound of formula (I), comprising the step of:

reacting a compound of formula (II):

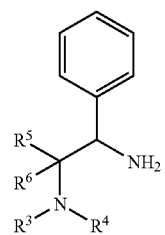

(II)

wherein $R^3$, $R^4$, $R^5$ and $R^6$ are as defined in formula (I), with a compound of formula (III):

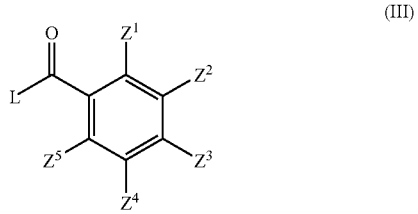

(III)

wherein $Z^1$, $Z^2$, $Z^3$, $Z^4$ and $Z^5$ are as defined in formula (I) and L represents a suitable leaving group;

and thereafter optionally:
removing any protecting groups and/or
converting a compound of formula (I) into another compound of formula (I) and/or
forming a salt or solvate.

Suitable leaving groups L include halogen, hydroxy, OC(=O)alkyl, OC(=O)O-alkyl and $OSO_2Me$.

Compounds of formula (I) can be converted into further compounds of formula (I) using standard techniques. For example, and by way of illustration rather than limitation, possible conversion reactions include acylation with an appropriate acylating agent such as acetyl chloride, alkylation using an appropriate alkylating reagent such as methyl iodide, and sulfonylation using a sulfonylating agent such as methanesulfonic anhydride and N-alkylation by reductive amination using a ketone or an aldehyde in the presence of a reducing agent such as sodiumtriacetoxyborohydride.

Pharmaceutically acceptable salts may be prepared conventionally by reaction with the appropriate acid or acid derivative.

In a further aspect, the present invention provides a compound of formula (II):

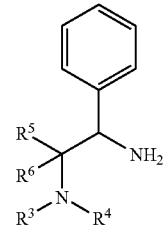

(II)

wherein $R^3$, $R^4$, $R^5$ and $R^6$ are as defined in formula (I), with the proviso that the compound of formula (II) is not the compound wherein simultaneously $R^3$ and $R^4$ together with the nitrogen atom to which they are attached form an unsubstituted piperidine ring and $R^5$ and $R^6$ together with the carbon atom to which they are attached form an unsubstituted cyclopentyl ring.

Compounds of formula (II) are useful as intermediates in the synthesis of compounds of the invention.

The compounds of the present invention inhibit the GlyT1 transporter. The compounds may selectively inhibit the GlyT1 transporter over the GlyT2 transporter.

Such compounds would be suitable for the treatment of certain neurological and neuropsychiatric disorders. As used herein, the terms "treatment" and "treating" refer to the alleviation and/or cure of established symptoms as well as prophylaxis.

The affinities of the compounds of this invention for the GlyT1 transporter can be determined by the following assay:

HEK293 cells expressing the Glycine (Type 1) transporter were grown in cell culture medium [DMEM/NUT mix F12 containing 2 mM L-Glutamine, 0.8 mg/mL G418 and 10% heat inactivated fetal calf serum] at 37° C. and 5% $CO_2$. Cells grown to 70-80% confluency in T175 flasks were harvested and resuspended at $1.32 \times 10^6$ cells/mL in assay buffer [140 mM NaCl, 5.4 mM KCl, 1.8 mM $CaCl_2$, 0.8 mM $MgSO_4$, 20 mM HEPES, 5 mM glucose and 5 mM alanine, pH 7.4]. Compounds were serially diluted 2.5-fold in DMSO from a top concentration of 2.5 mM with each compound giving a 11 data point dose-response. 100 nL of compound at each concentration was added to the assay plate. An equal volume of Leadseeker™ WGA SPA beads (12.5 mg/ml suspended in assay buffer) was added to the cell suspension ($1.32 \times 10^6$) and 5 μL of the cell/bead suspension transferred to each well of a 384-well white solid bottom plate (3300 cells/well) containing 100 mL of test compounds. Substrate (5 μL) was added to each well (1:100 dilution of [$^3$H]-glycine stock in assay buffer containing 2.5 μM glycine). Final DMSO concentration was 1% v/v. Data was collected using a Perkin Elmer Viewlux. $pIC_{50}$ values were determined using ActivityBase.

The following assay may also be used:

HEK293 cells expressing the Glycine (Type 1) transporter are grown in cell medium (DMEM/NUT mix F12) containing 2 mM L-Glutamine, 0.8 mg/mL G418 and 10% heat inactivated fetal calf serum (Gibco BRL) at 37° C. in 5% $CO_2$. Cells grown to 70-80% confluency in T175 flasks are harvested and resuspended at $4 \times 10^5$ cells/ml in assay buffer [NaCl (140 mM), KCl (5.4 mM), $CaCl_2$ (1.8 mM), $MgSO_4$ (0.8 mM), HEPES (20 mM), glucose (5 mM) and alanine (5 mM), pH 7.4]. An equal volume of Leadseeker™ SPA beads (12.5 mg/ml suspended in assay buffer) is added to the cell suspension. Compounds are prepared as 10 mM stocks in DMSO. 2.5 fold serial dilutions of the compounds are made in DMSO from a top conc of 2.5 mM. 100 mL of compound at each concentration is added to the assay plate (384-well white solid bottom plate) using the hummingbird dispenser. 5 uL of the cell/bead mix is then added on top of the compound using a multidrop dispenser. Substrate (5 uL) is then added to each well (1:100 dilution of H3-glycine in assay buffer containing 2.5 uM glycine) Data is collected using a PerkinElmer Viewlux as 5 minute exposures. pIC50 data values are determined using Activity Base.

Compounds may be assayed in their free base form or in the form of a salt, for example the hydrochloride salt or the formate salt. The assays described above are generally considered to provide data that is correct to ±3 standard deviations=±0.5.

Compounds having a $pIC_{50}$ at the GlyT1 transporter of greater than or equal to 5.0 are considered to be active at the GlyT1 transporter. The example compounds below were found to have a $pIC_{50}$ at the GlyT1 transporter of greater than or equal to 5.0.

Accordingly, in a further aspect of the invention, there is provided a compound of formula (I) or a salt or solvate thereof: for use in therapy.

In another aspect of the invention, there is provided a compound of formula (I) as hereinbefore described or a salt or solvate thereof, for use in the treatment of a disorder mediated by GlyT1.

As used herein, the term "a disorder mediated by GlyT1" refers to a disorder that may be treated by the administration of a medicament that alters the activity of the GlyT1 transporter. As hereinbefore described, the action of GlyT1 transporters affects the local concentration of glycine around NMDA receptors. As a certain amount of glycine is needed for the efficient functioning of NMDA receptors, any change to that local concentration can affect NMDA-mediated neurotransmission. As hereinbefore described, changes in NMDA-mediated neurotransmission have been implicated in certain neuropsychiatric disorders such as dementia, depression and psychoses, for example schizophrenia, and learning and memory disorders, for example attention deficit disorders and autism. Thus, alterations in the activity of the GlyT1 transporter are expected to influence such disorders.

The disorders mediated by GlyT1 referred to herein include neurological and neuropsychiatric disorders, including psychoses such as schizophrenia, dementia and other forms of impaired cognition such as attention deficit disorders and organic brain syndromes. Other neuropsychiatric disorders include drug-induced (phencyclidine, ketamine and other dissociative anesthetics, amphetamine and other psychostimulants and cocaine) psychosis, psychosis associated with affective disorders, brief reactive psychosis, schizoaffective psychosis, and psychosis NOS, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), and NMDA receptor-related disorders such as autism, depression, benign forgetfulness, childhood learning disorders and closed head injury.

The compounds of formula (I) are of use as antipsychotic agents for example in the treatment of schizophrenia, schizoaffective disorders, schizophreniform diseases, psychotic depression, mania, acute mania, paranoid and delusional disorders.

Within the context of the present invention, the terms used herein are classified in the Diagnostic and Statistical Manual of Mental Disorders, 4$^{th}$ Edition, published by the American Psychiatric Association (DSM-IV) and/or the International Classification of Diseases, 10$^{th}$ Edition (ICD-10). The various subtypes of the disorders mentioned herein are contemplated as part of the present invention. Numbers in brackets after the listed diseases below refer to the classification code in DSM-IV.

In particular, the compounds of formula (I) are of use in the treatment of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-induced Psychotic Disorder including the subtypes With Delusions (293.81) and With Hallucinations (293.82); and Psychotic Disorder Not Otherwise Specified (298.9).

The compounds of formula (I) are also of use in the treatment of mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

The compounds of formula (I) are also of use in the treatment of anxiety disorders including Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-induced Anxiety Disorder and Anxiety Disorder Not Otherwise Specified (300.00).

The compounds of formula (I) are also of use in the treatment of substance-related disorders including Substance Use Disorders such as Substance Dependence and Substance Abuse; Substance-Induced Disorders such as Substance Intoxication, Substance Withdrawal, Substance-induced Delirium, Substance-Induced Persisting Dementia, Substance-induced Persisting Amnestic Disorder, Substance-induced Psychotic Disorder, Substance-induced Mood Disorder, Substance-induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-induced Psychotic Disorder, Alcohol-induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) are also of use in the treatment of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-induced Sleep Disorder including the subtypes Insomnia Type, Hypersomnia Type, Parasomnia Type and Mixed Type.

The compounds of formula (I) are also of use in the treatment of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50).

The compounds of formula (I) are also of use in the treatment of Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) are also of use in the treatment of Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9).

The compounds of Formula (I) are also of use in the enhancement of cognition including the treatment of cognition impairment in other diseases such as schizophrenia, bipolar disorder, depression, other psychiatric disorders and psychotic conditions associated with cognitive impairment. Within the context of the present invention, the term cognitive impairment includes for example the treatment of impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypothyroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The compounds of formula (I) are also of use in the treatment of sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The invention also provides a compound of formula (I) as hereinbefore described or a pharmaceutically acceptable salt or solvate thereof for use in the treatment of schizophrenia, mood disorders, anxiety disorders, substance-related disorders, sleep disorders, eating disorders, autistic disorder, attention-deficit/hyperactivity disorder, disruptive behaviour disorder, tic disorders, personality disorders, cognition impairment in other diseases, sexual dysfunction, Parkinson's disease, dyskinetic disorders, depression, bipolar disorder, cognitive impairment, obesity, emesis, movement disorders, obsessive-compulsive disorders, amnesia, aggression, vertigo, dementia and circadian rhythm disorders.

The invention also provides a compound of formula (I) as hereinbefore described or a pharmaceutically acceptable salt or solvate thereof for use in the treatment of psychotic disorders, substance abuse, cognitive impairment, obesity, and gastric motility disorders.

In another aspect of the invention, there is provided a method of treating a mammal, including a human, suffering from or susceptible to a disorder mediated by GlyT1, which comprises administering an effective amount of a compound of formula (I) as hereinbefore defined or a salt or solvate thereof.

The invention also provides a method of treating schizophrenia, mood disorders, anxiety disorders, substance-related disorders, sleep disorders, eating disorders, autistic disorder, attention-deficit/hyperactivity disorder, disruptive behaviour disorder, tic disorders, personality disorders, cognition impairment in other diseases, sexual dysfunction, Parkinson's disease, dyskinetic disorders, depression, bipolar disorder, cognitive impairment, obesity, emesis, movement disorders, obsessive-compulsive disorders, amnesia, aggression, vertigo, dementia and circadian rhythm disorders which comprises administering to a mammal in need thereof an effective amount of a compound of formula (I) as hereinbefore described or a pharmaceutically acceptable salt or solvate thereof.

The invention also provides a method of treating psychotic disorders, substance abuse, cognitive impairment, obesity and gastric motility disorders which comprises administering to a mammal in need thereof an effective amount of a compound of formula (I) as hereinbefore described or a pharmaceutically acceptable salt or solvate thereof.

The compounds of formula (I) are also of use as anticonvulsants. The compounds of formula (I) are thus useful in the treatment of convulsions in mammals, and particularly epilepsy in humans. "Epilepsy" is intended to include the following seizures: simple partial seizures, complex partial seizures, secondary generalised seizures, generalised seizures including absence seizures, myoclonic seizures, clonic seizures, tonic seizures, tonic clonic seizures and atonic seizures. The invention also provides a method of treating convulsions, which comprises administering to a mammal in need thereof an effective amount of a compound of formula (I) as hereinbefore described or a pharmaceutically acceptable salt or solvate thereof. Treatment of epilepsy may be carried out by the administration of a non-toxic anticonvulsant effective amount of a compound of the formula (III) or a pharmaceutically acceptable salt, or a composition as hereinbefore defined.

The compounds of formula (I) also find use in the treatment of neuropathic pain, for example in diabetic neuropathy, sciatica, non-specific lower back pain, multiple sclerosis pain, fibromyalgia, HIV-related neuropathy, neuralgia such as post-herpetic neuralgia and trigeminal neuralgia and pain resulting from physical trauma, amputation, cancer, toxins or chronic inflammatory conditions.

In another aspect of the invention, there is provided use of a compound of formula (I) as hereinbefore defined or a salt or solvate thereof in the preparation of a medicament for the treatment of a disorder mediated by GlyT1.

Preferably, the disorder mediated by GlyT1 to be treated by the use or method as hereinbefore described is a psychosis, including schizophrenia, dementia and attention deficit disorders, particularly schizophrenia.

The invention also provides the use of a compound of formula (I) as hereinbefore described or a pharmaceutically acceptable salt or solvate thereof in the manufacture of a medicament for the treatment of schizophrenia, mood disorders, anxiety disorders, substance-related disorders, sleep disorders, eating disorders, autistic disorder, attention-deficit/hyperactivity disorder, disruptive behaviour disorder, tic disorders, personality disorders, cognition impairment in other diseases, sexual dysfunction, Parkinson's disease, dyskinetic disorders, depression, bipolar disorder, cognitive impairment, obesity, emesis, movement disorders, obsessive-compulsive disorders, amnesia, aggression, vertigo, dementia and circadian rhythm disorders.

The invention also provides the use of a compound of formula (I) as hereinbefore described or a pharmaceutically acceptable salt or solvate thereof in the manufacture of a medicament for the treatment of psychotic disorders, substance abuse, cognitive impairment, obesity and gastric motility disorders.

As used herein, the term "effective amount" means that amount of a drug or pharmaceutical agent that will elicit the biological or medical response of a tissue, system, animal or human that is being sought, for instance, by a researcher or clinician.

Compounds for use according to the invention may be administered as the raw material but the active ingredients are preferably provided in the form of pharmaceutical compositions.

Accordingly, in a further aspect of the invention, there is provided a pharmaceutical composition comprising a compound of formula (I) as hereinbefore described or a salt or solvate thereof, and at least one pharmaceutically acceptable carrier, diluent or excipient.

These pharmaceutical compositions may be used in the treatment of clinical conditions for which a GlyT1 inhibitor is indicated such as, for example, schizophrenia. The carrier must be pharmaceutically acceptable to the recipient and must be compatible with, i.e. not have a deleterious effect upon, the other ingredients in the composition. The carrier may be a solid or a liquid and is preferably formulated with at least one compound of formula (I) or a salt or solvate thereof as a unit dose formulation. If desired, other physiologically active ingredients may also be incorporated in the pharmaceutical compositions of the invention.

It will be appreciated by those skilled in the art that the compounds according to the invention may advantageously be used in conjunction with one or more other therapeutic agents, for instance, different antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1B antagonists, 5HT1D antagonists, D1 agonists, M1 agonists and/or anticonvulsant agents, as well as atypical antipsychotic drugs and cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

Suitable atypical antipsychotic drugs which may be used in combination of the compounds of the invention include for example risperidone, olanzapine, ziprasidone, aripiprazole and clozapine.

It will be appreciated that the compounds of the combination or composition may be administered simultaneously (either in the same or different pharmaceutical formulations), separately or sequentially.

The compounds of formula (I) and their pharmaceutically acceptable salts and solvates thereof are also suitable for combination with other typical and atypical antipsychotics to provide improved treatment of psychotic disorders. Particular advantages associated with the combinations, uses and methods of treatment of compounds of formula (I) and their pharmaceutically acceptable salts and solvates thereof include equivalent or improved efficacy at doses of administration which are lower than those commonly used for the individual components. Improved treatments of positive symptoms and/or negative symptoms and/or cognitive symptoms of the psychotic disorder may also be observed. The combinations, uses and methods of treatment of the invention may also provide advantages in treatment of patients who fail to respond adequately or who are resistant to treatment with certain neuroleptic agents.

The combination therapies of the invention are preferably administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a pharmaceutically acceptable salt or solvate thereof and at least one neuroleptic agent are within the scope of the current invention. In one embodiment of adjunctive therapeutic administration as described herein, a patient is typically stabilised on a therapeutic administration of one or more of the components for a period of time and then receives administration of another component. Within the scope of this invention, it is preferred that the compounds of formula (I) or a pharmaceutically acceptable salt or solvate thereof is administered as adjunctive therapeutic treatment to patients who are receiving administration of at least one neuroleptic agent, but the scope of the invention also includes the adjunctive therapeutic administration of at least one neuroleptic agent to patients who are receiving administration of compounds of formula (I) or a pharmaceutically acceptable salt or solvate thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a pharmaceutically acceptable salt or solvate thereof to a patient receiving therapeutic administration of at least one neuroleptic agent. In a further aspect, the invention provides the use of compounds of formula (I) or a pharmaceutically acceptable salt or solvate thereof in the manufacture of a medicament for adjunctive therapeutic administration for the treatment of a psychotic disorder in a patient receiving therapeutic administration of at least one neuroleptic agent. The invention further provides compounds of formula (I) or a pharmaceutically acceptable salt or solvate thereof for use for adjunctive therapeutic administration for the treatment of a psychotic disorder in a patient receiving therapeutic administration of at least one neuroleptic agent.

In a further aspect, the invention provides a method of treatment of a psychotic disorder by adjunctive therapeutic administration of at least one neuroleptic agent to a patient receiving therapeutic administration of compounds of formula (I) or a pharmaceutically acceptable salt or solvate thereof. In a further aspect, the invention provides the use of at least one neuroleptic agent in the manufacture of a medicament for adjunctive therapeutic administration for the treatment of a psychotic disorder in a patient receiving therapeutic administration of compounds of formula (I) or a pharmaceutically acceptable salt or solvate thereof. The invention further provides at least one neuroleptic agent for adjunctive therapeutic administration for the treatment of a psychotic disorder in a patient receiving therapeutic administration of compounds of formula (I) or a pharmaceutically acceptable salt or solvate thereof.

In a further aspect, the invention provides a method of treatment of a psychotic disorder by simultaneous therapeutic administration of compounds of formula (I) or a pharmaceutically acceptable salt or solvate thereof in combination with at least one neuroleptic agent. The invention further provides the use of a combination of compounds of formula (I) or a pharmaceutically acceptable salt or solvate thereof and at least one neuroleptic agent in the manufacture of a medicament for simultaneous therapeutic administration in the treatment of a psychotic disorder. The invention further provides the use of compounds of formula (I) or a pharmaceutically acceptable salt thereof in the manufacture of a medicament for simultaneous therapeutic administration with at least one neuroleptic agent in the treatment of a psychotic disorder. The invention further provides compounds of formula (I) or a pharmaceutically acceptable salt thereof for use for simultaneous therapeutic administration with at least one neuroleptic agent in the treatment of a psychotic disorder. The invention further provides the use of at least one neuroleptic agent in the manufacture of a medicament for simultaneous therapeutic administration with compounds of formula (I) or a pharmaceutically acceptable salt thereof in the treatment of a psychotic disorder.

In further aspects, the invention provides a method of treatment of a psychotic disorder by simultaneous therapeutic administration of a pharmaceutical composition comprising compounds of formula (I) or a pharmaceutically acceptable salt or solvate thereof and at least one mood stabilising or antimanic agent, a pharmaceutical composition comprising compounds of formula (I) or a pharmaceutically acceptable salt or solvate thereof and at least one mood stabilising or antimanic agent, the use of a pharmaceutical composition comprising compounds of formula (I) or a pharmaceutically acceptable salt or solvate thereof and at least one mood stabilising or antimanic agent in the manufacture of a medicament for the treatment of a psychotic disorder, and a pharmaceutical composition comprising compounds of formula (I) or a pharmaceutically acceptable salt or solvate thereof and at least one mood stabilising or antimanic agent for use in the treatment of a psychotic disorder.

In a further aspect, the invention provides a kit-of-parts for use in the treatment of a psychotic disorder comprising a first dosage form comprising compounds of formula (I) or a pharmaceutically acceptable salt or solvate thereof and one or more further dosage forms each comprising a neuroleptic agent for simultaneous therapeutic administration.

Within the context of the present invention, the term psychiatric disorder includes those disorders mentioned above, such as schizophrenia, mood disorders, anxiety disorders, substance-related disorders, sleep disorders, eating disorders, autistic disorder, attention-deficit/hyperactivity disorder, disruptive behaviour disorder, tic disorders, personality disorders, cognition impairment in other diseases, sexual dysfunction, dyskinetic disorders, depression, bipolar disorder, cognitive impairment and obsessive-compulsive disorders and all the various forms of the disorders as mentioned herein. which are contemplated as part of the present invention.

Examples of neuroleptic/antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of neuroleptic drugs that are preferred for use in the present invention are shown in Table A.

TABLE A

Neuroleptic drugs

| Common Name | Trade Name | Route of Administration | Form | Dosage Range and (Median)[a] |
|---|---|---|---|---|
| Clozapine | CLOZARIL | oral | tablets | 12.5-900 mg/day (300-900 mg/day) |
| Olanzapine | ZYPREXA | oral | tablets | 5-25 mg/day (10-25 mg/day) |
| Ziprasidone | GEODON | oral | capsules | 20-80 mg/twice a day (80-160 mg/day) |
| Risperidone | RISPERDAL | oral | solution tablets | 2-16 mg/day tablets (4-12 mg/day) |
| Quetiapine fumarate | SEROQUEL | oral | tablets | 50-900 mg/day (300-900 mg/day) |
| Sertindole | SERLECT | | | (4-24 mg/day) |
| Amisulpride | | | | |
| Haloperidol | HALDOL | oral | tablets | 1-100 mg/day (1-15 mg/day) |
| Haloperidol Decanoate | HALDOL Decanoate | parenteral | injection | |
| Haloperidol lactate | HALDOL INTENSOL | oral parenteral | solution injection | |
| Chlorpromazine | THORAZINE | rectal oral parenteral | suppositories capsules solution tablets injection | 30-800 mg/day (200-500 mg/day) |
| Fluphenazine | PROLIXIN | | | 0.5-40 mg/day (1-5 mg/day) |
| Fluphenazine decanoate | PROLIXIN Decanoate | parenteral | injection | (about one-half the dosage shown for oral) |
| Fluphenazine enanthate | PROLIXIN | parenteral | injection | (same as above |
| Fluphenazine hydrochloride | PROLIXIN | oral parenteral | elixer solution injection | |
| Thiothixene | NAVANE | oral | capsules | 6-60 mg/day (8-30 mg/day) |
| Thiothixene hydrochloride | NAVANE | oral parenteral | solution injection | |
| Trifluoperazine | STELAZINE | | | (2-40 mg/day) |
| Perphenazine | TRILAFON | oral parenteral | solution tablets injection | 12-64 mg/day (16-64 mg/day) |
| Perpehazine and Amitriptyline hydrochloride | ETRAFON TRIAVIL | oral | tablets | |
| Thioridazine | MELLARIL | oral | suspension solution tablets | 150-800 mg/day (100-300 mg/day) |
| Mesoridazine | | | | (30-400 mg/day) |
| Molindone | MOBAN | | | 50-225 mg/day (15-150 mg/day) |
| Molindone hydrochloride | MOBAN | oral | solution | |
| Loxapine | LOXITANE | | | 20-250 mg/day (60-100 mg/day) |
| Loxapine hydrochloride | LOXITANE | oral parenteral | solution injection | |
| Loxapine succinate | LOXITANE | oral | capsules | |
| Pimozide | | | | (1-10 mg/day) |
| Flupenthixol | | | | |
| Promazine | SPARINE | | | |
| Triflupromazine | VESPRIN | | | |
| Chlorprothixene | TARACTAN | | | |
| Droperidol | INAPSINE | | | |
| Acetophenazine | TINDAL | | | |
| Prochlorperazine | COMPAZINE | | | |
| Methotrimeprazine | NOZINAN | | | |
| Pipotiazine | PIPOTRIL | | | |
| Aripiprazole | | | | |
| Hoperidone | | | | |

Examples of tradenames and suppliers of selected neuroleptic drugs are as follows clozapine (available under the tradename CLOZARIL®, from Mylan, Zenith Goldline, UDL, Novartis); olanzapine (available under the tradename ZYPREX®, from Lilly ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK); fluphenazine (available under the tradename PROLIXIN®, from Apothecon, Copley, Schering, Teva, and American Pharmaceutical Partners, Pasadena); thiothixene (available under the tradename NAVANE®;, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman; perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE®; from Watson). Furthermore, benperidol (Glianimon®), perazine (Taxilan®) or melperone (Eunerpan®)) may be used.

Other preferred neuroleptic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

Particularly preferred neuroleptic agents for use in the invention are olanzapine, risperidone, quetiapine, aripiprazole, haloperidol, clozapine, ziprasidone and osanetant.

It will be appreciated by those skilled in the art that the compounds according to the invention may advantageously be used in conjunction with one or more other therapeutic agents, for instance, different antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1B antagonists, 5HT1D antagonists, D1 agonists, M1 agonists and/or anticonvulsant agents, as well as atypical antipsychotic drugs and cognitive enhancers.

Suitable 5HT3 antagonists which may be used in combination of the compounds of the inventions include for example ondansetron, granisetron, metoclopramide. Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

Suitable atypical antipsychotic drugs which may be used in combination of the compounds of the invention include for example risperidone, olanzapine, ziprasidone, aripiprazole and clozapine.

It will be appreciated that the compounds of the combination or composition may be administered simultaneously (either in the same or different pharmaceutical formulations), separately or sequentially.

For use in medicine, the compounds of the present invention are usually administered as a standard pharmaceutical composition. The present invention therefore provides in a further aspect a pharmaceutical composition comprising a compound of formula (I) as hereinbefore described or a pharmaceutically (i.e. physiologically) acceptable salt thereof and a pharmaceutically (i.e. physiologically) acceptable carrier. The pharmaceutical composition can be for use in the treatment of any of the conditions described herein.

Possible formulations include those suitable for oral, sublingual, buccal, parenteral (for example, subcutaneous, intramuscular, or intravenous), rectal, topical and intranasal administration and in forms suitable for administration by inhalation or insufflation (either through the mouth or nose). The most suitable means of administration for a particular patient will depend on the nature and severity of the conditions being treated and on the nature of the active compound, but, where possible, oral administration is preferred.

Formulations suitable for oral administration may be provided as discrete units, such as tablets, capsules, cachets, or lozenges, each containing a predetermined amount of the active compound; as powders or granules; as solutions or suspensions in aqueous or non-aqueous liquids; or as oil-in-water or water-in-oil emulsions. For example, a compound of the invention may be prepared as a formulation with a controlled release profile. This may be in any of the above mentioned pharmaceutical forms. For example, it may be a gel formulation in a non aqueous oily vehicle, for example Miglyol, with a suitable gelling agent if required, for example methyl cellulose or hydrophobic colloidal silica.

Formulations suitable for sublingual or buccal administration include lozenges comprising the active compound and, typically, a flavoured base, such as sugar and acacia or tragacanth and pastilles comprising the active compound in an inert base, such as gelatin and glycerin or sucrose and acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient and one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethylene glycols, alcohols, and combinations thereof.

Formulations of compounds of the invention may, for example, be composed so as to improve the exposure profile of the compound of the invention.

Compositions suitable for transdermal administration include ointments, gels and patches. Preferably the composition is in unit dose form such as a tablet, capsule or ampoule.

The formulations of the invention may be prepared by any suitable method, typically by uniformly and intimately admixing the active compound(s) with liquids or finely divided solid carriers, or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions for parenteral administration are typically prepared by dissolving the active compound in sufficient water to give the desired concentration and then rendering the resulting solution sterile and isotonic.

It will be appreciated that the precise dose administered will depend on the age and condition of the patient and the frequency and route of administration and will be at the ultimate discretion of the attendant physician. The compound may be administered in single or divided doses and may be administered one or more times, for example 1 to 4 times per day.

A proposed dose of the active ingredient for use according to the invention for oral, sub-lingual, parenteral, buccal, rectal, intranasal or topical administration to a human (of approximately 70 kg bodyweight) for the treatment of neurological and neuropsychiatric disorders mediated by a GlyT1 inhibitor, including schizophrenia, may be about 1 to about 1000 mg, preferably about 5 to about 500 mg, more preferably about 10 to about 100 mg of the active ingredient per unit dose which could be administered, for example, 1 to 4 times per day.

Compounds of the invention may be used as PET ligands (for example labelled with carbon-11 or fluorine-18) or as SPECT ligands (for example labelled with iodine-123 or meta stable technetium-99) for in vivo visualisation and quantification of the GlyT1 transporter. For example, they may be used in PET or SPECT imaging of the brain. In the context of this patent, PET shall mean: positron emission tomography and SPECT (=SPET) shall mean: single photon emission (computed) tomography.

All publications, including but not limited to patents and patent applications, cited in this specification are herein incorporated by reference as if each individual publication were specifically and individually indicated to be incorporated by reference herein as though fully set forth.

The invention is further illustrated by the following non-limiting examples.

Abbreviations:

| | |
|---|---|
| THF | tetrahydrofuran |
| DCM | dichloromethane |
| DMF | dimethylformamide |
| HATU | O-(7-azabenzotriazol-1-yl)-N,N,N',N'-tetramethyluroniumhexafluorophosphate |
| EDC | N-(3-(dimethylamino)propyl)-N-ethylcarbodiimide hydrochloride |
| HOAt | 3H-(1,2,3)-triazolo(4,5-b)pyridine-3-ol |

-continued

| | |
|---|---|
| NMP | N-methylpyrrolidinone |
| DIPEA | N,N-diisopropylethylamine |
| HOBt | 1-hydroxybenzotriazole hydrate |

Analytical LC/MS Chromatography Conditions:

| Method A | |
|---|---|
| Column: | Waters Atlantis 50 mm × 4.6 mm, 3 um particle size |
| Mobile phase: | A: 0.05% Formic acid + Water<br>B: Acetonitrile + 0.05% Formic acid |
| Gradient: | 5-min runtime: 3% B to 97% B over 4 min |
| Flow rate: | 3 ml/min |
| UV wavelength range: | 220-330 nm |
| Temperature: | 30° C. |
| Method B * | |
| Column: | Waters Atlantis 20 mm × 4.6 mm, 3 um particle size |
| Mobile phase: | A: 0.1% Formic acid + Water<br>B: Acetonitrile + 0.1% Formic acid |
| Gradient: | 5.5-min runtime: 3% B to 97% B over 5.3 min |
| Flow rate: | 1 ml/min |
| UV wavelength range: | 210-350 nm |
| Temperature: | Ambient |

Mass Directed Auto-Purification System Chromatography Conditions:

| | |
|---|---|
| Column: | Waters Atlantis 19 mm × 100 mm or 30 mm × 100 mm, 5 um particle size |
| Mobile phase: | A: 0.1% Formic acid + Water<br>B: Acetonitrile + 0.1% Formic acid |
| Gradient: | 13.5 min runtime with 10 min gradient dependant on analytical retention time |
| Flow rate: | 20 or 40 ml/min |

General:

Throughout the examples section, the following terminology is adopted with regard to chiral compounds: when a mixture of two enantiomers has been prepared, the compound is described as (±). When a single enantiomer (that is to say mixture chirally enriched in one of the enantiomers) has been prepared, it is referred to as "chiral". The absolute stereochemistry has not been ascertained at the time of filing. Individual enantiomers of some materials prepared are identified by virtue of optical rotations and such materials are identified as the (+) or (−) enantiomers. Where optical rotation information is not yet available, individual enantiomers of the products are individually identifiable by virtue of the chiral HPLC characteristics of the amine intermediate.

Where reactions are described as having been carried out in a similar manner to earlier, more completely described reactions, the general reaction conditions used were essentially

Description 1: 1-(Dimethylamino)cyclopentanecarbonitrile

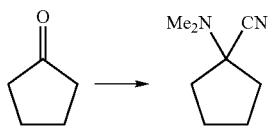

To a suspension of dimethylamine hydrochloride (8.15 g; 0.1 mol) in cyclopentanone (8.4 g; 0.1 mol) cooled (ice bath) was added dropwise a solution of potassium cyanide (6.5 g; 0.1 mol) in water (50 ml) over 10 min. After vigorous stirring at room temperature for 18 h, the crude reaction mixture was extracted three times with diethyl ether (3×200 ml) and the combined extracts washed twice with water (2×50 ml), dried ($Na_2SO_4$), and evaporated to afford the title product as a pale yellow oil (12.5 g) which was used without further purification. $^1$H NMR (CDCl$_3$) δ: 1.7-2.0 (6H, m), 2.15-2.3 (2H, m), 3.3 (6H, s). Mass Spectrum (Electrospray LC/MS): Found 112 (MH$^+$–HCN). $C_8H_{14}N_2$ requires 138.

Alternative Method:

To a stirred, ice cooled mixture of dimethylamine hydrochloride (26.32 g; 0.323 mol) and cyclopentanone (27.15 g; 0.323 mol) was added dropwise a solution of potassium cyanide (21.02 g; 0.323 mol) in water (170 ml) over 10 min. The mixture was stirred at room temperature overnight. Then, the mixture was extracted into diethylether (2×200 ml) and the combined organics were washed with brine (200 ml), dried ($Na_2SO_4$), and evaporated in vacuo to afford the title product as a colourless liquid (43 g, 96.5%)

Description 2: (±){1-[Amino(phenyl)methyl]cyclopentyl}dimethylamine

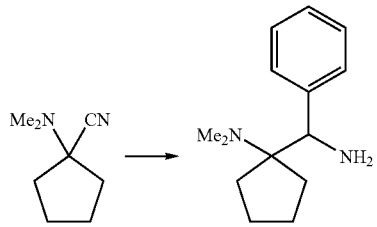

To a solution of 1-(dimethylamino)cyclopentanecarbonitrile D1 (4 g; 28.9 mmol) in THF (30 ml) at –70° C. under argon was added dropwise a solution of phenyllithium in dibutylether (17.7 ml of a 1.8M solution; 32 mmol). The reaction mixture was allowed to warm to room temperature over 3 h., recooled to 0° C. and methanol added (30 ml) followed by careful addition of sodium borohydride (3.3 g; 87 mmol). After stirring at room temperature for 18 h, the reaction mixture was cooled to 0° C. and saturated aqueous sodium bicarbonate added. The organic phase was evaporated and the resulting slurry extracted three times with DCM (3×150 ml). The combined extracts were dried ($Na_2SO_4$), and evaporated to afford the crude product as a yellow oil (6.8 g). Half of the crude product was chromatographed on silica gel eluting with DCM-methanol (9/1) and DCM-2M ammonia in methanol mixtures (95/5 to 9/1 to 8/2) to afford the title product as a colourless oil (2.3 g). This oil was dissolved in diethyl ether (20 ml) and hydrogen chloride in diethylether was added at 0° C. After 20 min, the suspension was filtered to give the dihydrochloride salt (2.8 g) of the title product as a white solid. $^1$H NMR (DMSO) δ: 1.25 (2H, bs), 1.36 (2H, bs), 1.66-2.13 (4H, m), 2.64 (3H, s), 2.79 (3H, s), 4.92 (1H, bs), 7.32 (3H, m), 7.54 (2H, m), 8.95 (3H, bs), 10.82 (1H, bs).

Alternative Method:

To a solution of 1-(dimethylamino)cyclopentanecarbonitrile D1 (43 g; 311 mmol) in THF (1 L) at –70° C. under argon was added dropwise a solution of phenyllithium in dibutylether (346 ml of a 1.8M solution; 622 mmol) over 10 minutes. The reaction mixture was stirred at –70° C. for 2 h, then allowed to warm to room temperature and it was stirred overnight. The reaction mixture was cooled in ice and saturated aqueous sodium bicarbonate solution was added. The mixture was stirred for 30 minutes, separated and the aqueous layer extracted with diethyl ether. The combined organics were dried ($Na_2SO_4$) and concentrated under reduced pressure to give an oil.

The oil was dissolved in methanol (1.2 L) and cooled in ice. Sodium borohydride (20 g) was added in 4 portions over 5 minutes and the mixture was stirred for half an hour with ice cooling. The cooling was then removed and stirring was continued at room temperature for one and a half hours. The reaction mixture was then ice cooled and water was added. The resultant mixture was evaporated in vacuo and fractioned between 2N HCl and ethyl acetate. The organics were extracted with 2N HCl. The combined acid extracts were washed with ethyl acetate, basified with NaOH and extracted into DCM. The combined DCM extracts were dried ($Na_2SO_4$), and evaporated in vacuo to afford the product as a pale green liquid (64.66 g, 95.4%).

Description 3: {1-[Amino(phenyl)methyl]cyclopentyl}dimethylamine Enantiomer 1 and Enantiomer 2

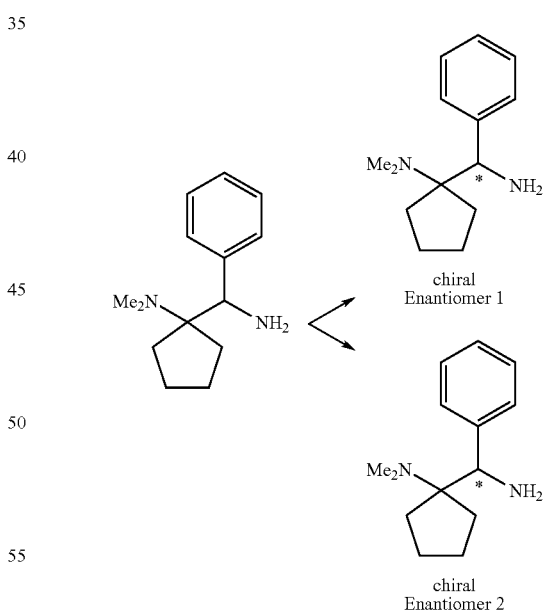

Method 1.

Racemic {1-[amino(phenyl)methyl]cyclopentyl}dimethylamine D2 (0.6 g; 2.75 mmol) was separated by semi-preparative chiral HPLC using the conditions described below to afford the title products, enantiomer 1, (0.27 g); Chiral HPLC: 98% ee; $^1$H NMR (CDCl3) δ: 0.42 (1H, m), 1.32 (3H, m), 1.49 (1H, m), 1.63 (1H, m), 1.76 (1H, m), 1.95 (3H, m), 2.29 (6H, s), 4.39 (1H, s), 7.28 (3H, m), 7.50 (2H, d);

Mass spectrum (Electrospray LC/MS): Found 219 (MH+). C$_{14}$H$_{22}$N$_2$ requires 218; and enantiomer 2 (0.28 g); Chiral HPLC: 98% ee; $^1$H NMR (CDCl3) δ: 0.42 (1H, m), 1.32 (3H, m), 1.49 (1H, m), 1.63 (1H, m), 1.76 (1H, m), 1.95 (3H, m), 2.29 (6H, s), 4.39 (1H, s), 7.28 (3H, m), 7.50 (2H, d); Mass spectrum (Electrospray LC/MS): Found 219 (MH+). C$_{14}$H$_{22}$N$_2$ requires 218.

Semi-Preparative HPLC Conditions:

| Column: | Chiralpak AD-H 5 μm, 250 × 21 mm |
|---|---|
| Mobile phase: | A: n-Hexane; B: Ethanol + 0.1% isopropylamine |
| Gradient: | isocratic 5% B |
| Flow rate: | 7 ml/min |
| UV wavelength range: | 225 nm |
| Elution time: | 30 min |

Analytical Chromatography Conditions:

| Column: | chiralpak AD-H 5 um, 250 × 4.6 mm |
|---|---|
| Mobile phase: | A: n-Hexane; B: Ethanol + 0.1% isopropyl amine |
| Gradient: | isocratic 5% B |
| Flow rate: | 1 ml/min |
| UV wavelength range: | 200-400 nm |
| Analysis time: | 10 min |
| Ret. Time: | 5.9 min (Enantiomer 1); 7.6 min (Enantiomer 2) |

Method 2.

Salt Formation:

To a solution of racemic {1-[amino(phenyl)methyl] cyclopentyl}dimethylamine D2 (16.9 g; 77.5 mmol) in isopropanol (170 ml) at 50° C., was added dropwise a solution of (R)-methoxy phenylacetic acid (12.84 g; 77.5 mmol) in isopropanol (75 ml). After 20 min the mixture was cooled to room temperature and left stirring for a further 4 h. The precipitated solid was collected by filtration (13.42 g).

Regeneration of Chiral Free Base:

The solid was then treated with 1M NaOH (50 ml) and DCM (167 ml). The phases were separated and the aqueous phase washed with DCM (4×167 ml). The combined organic phases were washed with 1M NaOH (2×35 ml), then brine (100 ml), dried (Na$_2$SO$_4$), and concentrated to yield the title compound, enantiomer 2, as a colourless oil (7.6 g). Chiral HPLC:>96% ee; $^1$H NMR (CDCl$_3$) δ: 0.42 (1H, m), 1.32 (3H, m), 1.49 (1H, m), 1.63 (1H, m), 1.76 (1H, m), 1.95 (3H, m), 2.29 (6H, s), 4.39 (1H, s), 7.28 (3H, m), 7.50 (2H, d); Mass spectrum (Electrospray LC/MS): Found 219 (MH+). C$_{14}$H$_{22}$N$_2$ requires 218.

Description 4:
2-Methyl-2-(1-pyrrolidinyl)propanenitrile

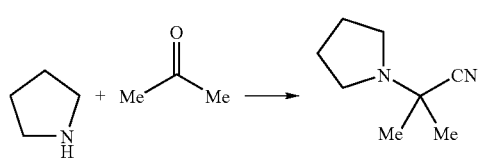

To a stirred, ice-cooled mixture of pyrrolidine (8.35 ml; 0.1 mol) and acetone (7.34 ml; 0.1 mol) was added a solution of potassium cyanide (6.51 g; 0.1 mol) in water (50 ml) dropwise over 10 min. After stirring at room temperature overnight, the crude reaction mixture was extracted with diethyl ether (2×250 ml) and the combined extracts washed with saturated brine (150 ml), dried (MgSO$_4$), and evaporated under reduced pressure to afford the title product as a pale green liquid (10.7 g; 78%) which was used without further purification. $^1$H NMR (CDCl$_3$) δ: 1.51 (6H, s), 1.80-1.90 (4H, m), 2.70-2.80 (4H, m).

Description 5: (±)[2-Methyl-1-phenyl-2-(1-pyrrolidinyl)propyl]amine

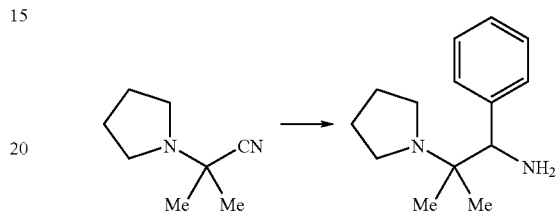

To a solution of 2-methyl-2-(1-pyrrolidinyl)propanenitrile D4 (10.7 g; 77.54 mmol) in THF (400 ml) at −70° C. under argon was added over 10 minutes a solution of phenyllithium in dibutylether (86.3 ml of a 1.8M solution; 155 mmol). The reaction mixture was stirred at −70° C. for 2 hours then allowed to warm to room temperature and stirred overnight. The reaction mixture was cooled in ice as saturated aqueous sodium hydrogen carbonate (400 ml) was added. After stirring for a further 30 minutes the layers were separated, and the aqueous layer extracted with ether (200 ml). Combined organics were dried (MgSO$_4$) and evaporated. The residual amber oil was dissolved in methanol (400 ml), cooled in ice and sodium borohydride (5.2 g; 137 mmol) added in four portions over 5 minutes. The reaction mixture was stirred with ice cooling for 30 minutes, the ice removed and stirred at room temperature for 1.5 hours. The mixture was cooled in ice as water (50 ml) was added prior to concentration in vacuo to approx 70 ml. The mixture was partitioned between 2N HCl (100 ml) and ethyl acetate (400 ml) and the organics extracted with 2N HCl (2×100 ml). Combined acidic aqueous layers were washed with ethyl acetate (200 ml), basified with 50% NaOH and extracted with DCM (3×150 ml). Combined DCM organic extracts were dried (Na$_2$SO$_4$) and evaporated in vacuo to afford the title compound as a colourless solid (15 g: 88%) $^1$H NMR (CDCl$_3$), δ: 0.75 (3H, s), 0.99 (3H, s), 1.70-1.76 (4H, m), 1.80 (2H, bs), 2.65-2.70 (4H, m), 4.08 (1H, s), 7.20-7.42 (5H, m).

Description 6: (+)-[2-Methyl-1-phenyl-2-(1-pyrrolidinyl)propyl]amine

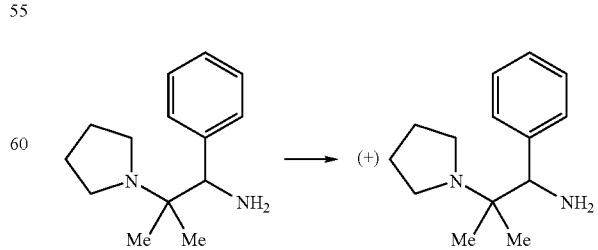

A solution of (R)-(−)-α-methoxyphenylacetic acid (8.08 g; 49 mmol) in 2-propanol (50 ml) was added dropwise over 10 minutes to a stirred solution of [2-methyl-1-phenyl-2-(1-pyrrolidinyl)propyl]amine D5 (10.64 g; 49 mmol) in 2-propanol (107 ml) at 57° C. After complete addition heating was continued for a further 10 minutes. Heating was then removed and stirring continued for one and three quarter hours. Further 2-propanol (100 ml) was added and the mixture filtered and the solid washed with 2-propanol (3×50 ml), ether (100 ml) and dried. The solid was recrystallised from boiling 2-propanol (1 L) and the crystals filtered, washed with cold 2-propanol, ether and dried. A sample was partitioned between saturated aqueous sodium hydrogen carbonate and DCM and the organic layer passed through a phase separation cartridge and blown down with argon to afford the title compound as a colourless solid. $^1$H NMR (CDCl$_3$), δ: 0.75 (3H, s), 0.99 (3H, s), 1.70-1.79 (4H, m), 1.85 (2H, bs), 2.65-2.70 (4H, m), 4.08 (1H, s), 7.20-7.42 (5H, m). Chiral HPLC: 97.5% ee, corresponding to the slower running enantiomer 2. $[\alpha]_D$=+28.5° (c=1, CHCl$_3$ at 27.5° C.). The remaining free base was liberated in a similar manner (3.55 g, 66%).

Conditions for Resolution of Racemate D5 were as Follows:—

Analytical Chromatography Conditions:

| | |
|---|---|
| Column: | chiralcel OD-H 5 um, 250 × 4.6 mm i.d. 10 micron particle size |
| Mobile phase: | Heptane:Ethanol (90:10) |
| Gradient: | isocratic |
| Flow rate: | 1 ml/min |
| UV wavelength range: | 254 nm |
| Analysis time: | 10 min |
| Ret. Time: | 5.4 min (Enantiomer 1); 7.0 min (Enantiomer 2) |

Description 7:
2-Methyl-2-(1-piperidinyl)propanenitrile

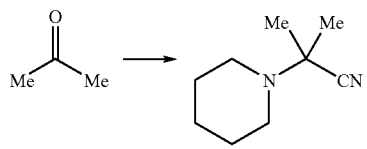

The title compound (2.33 g, 77%) was prepared from piperidine hydrochloride (2.43 g, 20 mmol), acetone (1.16 g, 20 mmol) and potassium cyanide (1.30 g, 20 mmol) in water (10 ml) in a similar manner to that described in D1. $^1$H NMR (CDCl$_3$) δ: 1.46 (2H, m), 1.50 (6H, s), 1.63 (4H, m), 2.59 (4H, m).

Description 8: (±)2-Methyl-1-phenyl-2-(1-piperidinyl)-1-propanamine

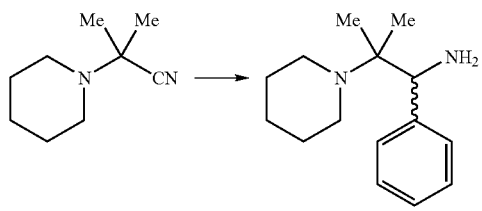

The title compound (1.16 g, 56%) was prepared from 2-methyl-2-(1-piperidinyl)propanenitrile D7 (1.30 g, 8.6 mmol), and phenyllithium in dibutylether (5.2 ml of a 1.8M solution; 9.4 mmol) in THF (15 ml), followed by reaction with sodium borohydride (0.975 g, 25.7 mmol) in methanol (20 ml) in a similar manner to that described in D2. $^1$H NMR (CDCl$_3$) δ: 0.76 (3H, s), 0.91 (3H, s), 1.44 (2H, m), 1.54-1.65 (4H, m), 1.95 (2H, m), 2.57 (4H, m), 4.19 (1H, s), 7.20-7.31 (3H, m), 7.40 (2H, m).

Description 9:
1-(1-Pyrrolidinyl)cyclopentanecarbonitrile

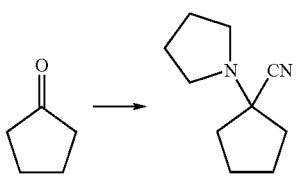

The title compound (2.50 g, 76%) was prepared from pyrrolidine (1.42 g, 20 mmol), cyclopentanone (1.68 g, 20 mmol) and potassium cyanide (1.30 g, 20 mmol) in water (10 ml) in a similar manner to that described in D4. $^1$H NMR (CDCl$_3$) δ: 1.80-1.90 (10H, m), 2.15 (2H, m), 2.71 (4H, m).

Description 10: (±)1-Phenyl-1-[1-(1-pyrrolidinyl)cyclopentyl]methanamine

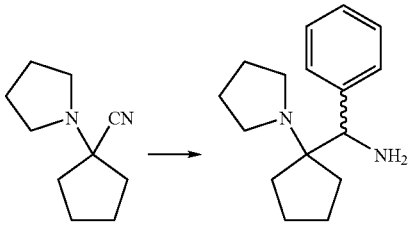

The title compound (0.55 g, 56%) was prepared from 1-(1-pyrrolidinyl)cyclopentane carbonitrile D9 (0.66 g, 4 mmol), and phenyllithium in dibutylether (2.4 ml of a 1.8M solution; 4.4 mmol) in THF (4 ml), followed by reaction with sodium borohydride (0.456 g, 12 mmol) in methanol (4 ml) in a similar manner to that described in D2. $^1$H NMR (CDCl$_3$) δ: 0.41 (1H, m), 1.17 (1H, m), 1.35 (2H, m), 1.60 (2H, m), 1.73 (5H, m), 1.84-2.02 (3H, m), 2.64-2.74 (4H, m), 4.27 (1H, s), 7.21-7.31 (3H, m), 7.48 (2H, m).

Description 11:
1-(Diethylamino)cyclopentanecarbonitrile

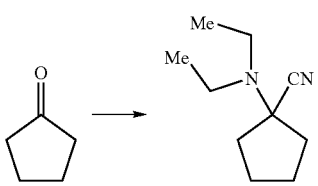

The title compound (2.06 g, 62%) was prepared from diethylamine hydrochloride (2.14 g, 20 mmol), cyclopentanone (1.68 g, 20 mmol) and potassium cyanide (1.30 g, 20 mmol) in water (10 ml) in a similar manner to that described in D1. $^1$H NMR (CDCl$_3$) δ: 1.11 (6H, t, J=7 Hz), 1.78-1.88 (6H, m), 2.22 (2H, m), 2.71 (4H, q, J=7 Hz).

Description 12: (±)1-[Amino(phenyl)methyl]-N,N-diethylcyclopentanamine

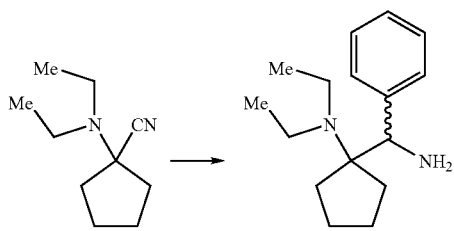

The title compound (0.45 g, 47%) was prepared from 1-(diethylamino)cyclopentane carbonitrile D11 (0.65 g, 3.9 mmol), and phenyllithium in dibutylether (2.4 ml of a 1.8M solution; 4.3 mmol) in THF (4 ml), followed by reaction with sodium borohydride (0.445 g, 11.7 mmol) in methanol (4 ml) in a similar manner to that described in D2. $^1$H NMR (CDCl$_3$) δ: 0.42 (1H, m), 1.10 (6H, m), 1.35 (3H, m), 1.55 (1H, m), 1.66 (2H, m), 1.80-2.08 (3H, m), 2.53-2.70 (4H, m), 4.22 (1H, s), 7.20-7.31 (3H, m), 7.47 (2H, m).

Description 13:
1-(1-Azetidinyl)cyclopentanecarbonitrile

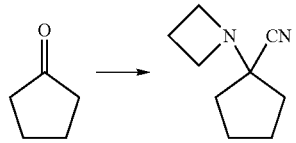

The title compound (1.29 g, 43%) was prepared from azetidine hydrochloride (1.85 g, 20 mmol), cyclopentanone (1.68 g, 20 mmol) and potassium cyanide (1.30 g, 20 mmol) in water (10 ml) in a similar manner to that described in D1. $^1$H NMR (CDCl$_3$) δ: 1.70-1.82 (6H, m), 1.86 (2H, m), 2.07 (2H, quin, J=7 Hz), 3.32 (4H, t, J=7 Hz).

Description 14: (±)1-[1-(1-Azetidinyl)cyclopentyl]-1-phenylmethanamine

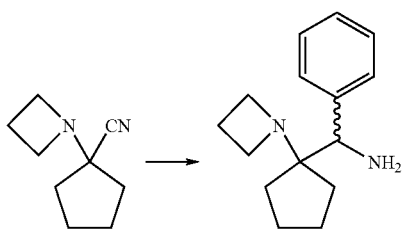

The title compound (0.45 g, 47%) was prepared from 1-(1-azetidinyl)cyclopentanecarbonitrile D13 (0.60 g, 4.0 mmol), and phenyllithium in ethers (2.6 ml of a 1.7M solution; 4.4 mmol) in THF (5 ml), followed by reaction with sodium borohydride (0.456 g, 12 mmol) in methanol (5 ml) in a similar manner to that described in D2. $^1$H NMR (CDCl$_3$) δ: 0.67 (1H, m), 1.06 (1H, m), 1.32 (4H, m), 1.48 (2H, m), 1.91-2.03 (4H, m), 3.24 (4H, m), 3.83 (1H, s), 7.20-7.32 (3H, m), 7.44 (2H, m).

Description 15: 2-(3-Azabicyclo[3.1.0]hex-3-yl)-2-methylpropanenitrile

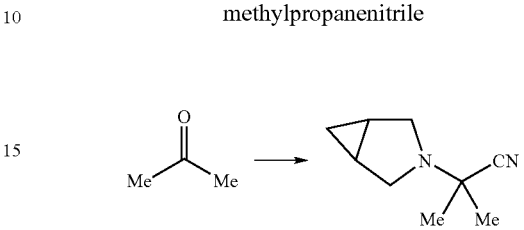

The title compound (583 mg, 84%) was prepared from 3-azabicyclo[3.1.0]hexane hydrochloride (550 mg, 4.6 mmol) [Pestic. Chem: Hum. Welfar Environ., Proc, Int, Congr. Pestic. Che., 5$^{th}$, 1982, 1,159-64, 1983], acetone (267 mg, 4.6 mmol) and potassium cyanide (300 mg, 4.6 mmol) in water (2.5 ml) in a similar manner to that described in D1. $^1$H NMR (CDCl$_3$) δ: 0.40 (1H, m), 0.58 (1H, m), 1.43 (8H, m), 2.64 (2H, m), 3.10 (2H, d, J=8 Hz).

Description 16: (±)2-(3-Azabicyclo[3.1.0]hex-3-yl)-2-methyl-1-phenyl-1-propanamine

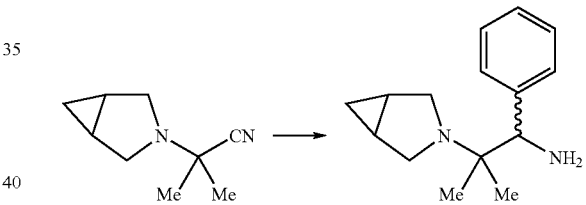

The title compound (393 mg, 44%) was prepared from 2-(3-azabicyclo[3.1.0]hex-3-yl)-2-methylpropanenitrile D15 (583 mg, 3.9 mmol), and phenyllithium in dibutylether (2.15 ml of a 2.0M solution; 4.3 mmol) in THF (7 ml), followed by reaction with sodium borohydride (445 mg, 11.7 mmol) in methanol (10 ml) in a similar manner to that described in D2. $^1$H NMR (CDCl$_3$) δ: 0.38 (1H, m), 0.66 (1H, m), 0.74 (3H, s), 0.93 (3H, s), 1.30-1.40 (2H, m), 1.74 (2H, bs), 2.67 (2H, m), 2.91 (2H, t, J=8 Hz), 4.03 (1H, s), 7.20-7.30 (3H, m), 7.38 (2H, m).

Description 17:
2-Ethyl-2-(1-pyrrolidinyl)butanenitrile

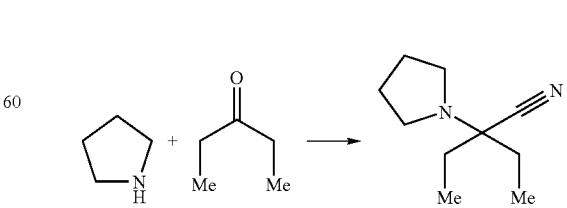

The title compound (8.8 g, 100%) was prepared from pyrrolidine (8.96 ml, 0.107 mol), 3-pentanone (8.61 g, 0.1 mol)

and potassium cyanide (6.51 g, 0.1 mol) in water (50 ml) in a similar manner to that described in D4. $^1$H NMR (CDCl$_3$) δ: 0.95 (6H, t, J=7.6 Hz), 1.67-1.90 (8H, m), 2.67-2.72 (4H, m).

Description 18: (±)[2-Ethyl-1-phenyl-2-(1-pyrrolidinyl)butyl]amine

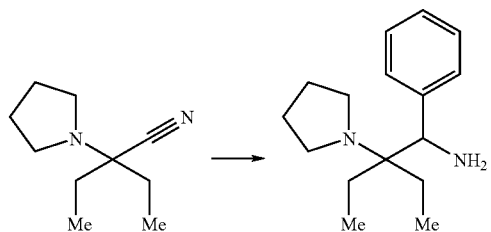

The title compound (11.5 g, 88%) was prepared from 2-ethyl-2-(1-pyrrolidinyl)butanenitrile D17 (8.8 g, 0.053 mol) and phenyllithium in dibutylether (59 ml of a 1.8M solution; 0.106 mol) in THF (350 ml), followed by reaction with sodium borohydride (3.9 g, 0.103 mol) in methanol (300 ml) in a similar manner to that described in D5. $^1$H NMR (CDCl$_3$) δ: 0.75 (3H, t), 0.95 (3H, t, J=7.6 Hz), 1.50-1.90 (10H, m), 2.70-2.95 (4H, m), 4.01 (1H, s), 7.19-7.41 (5H, m).

Description 19:
2-(Dimethylamino)-2-ethylbutanenitrile

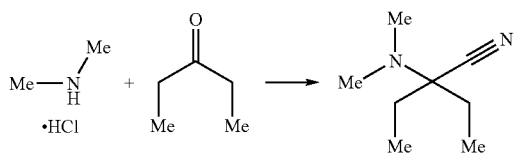

The title compound (8.05 g, 57.5%) was prepared from dimethylamine hydrochloride (8.154 g, 0.1 mol), 3-pentanone (8.61 g, 0.1 mol) and potassium cyanide (6.51 g, 0.1 mol) in water (50 ml) in a similar manner to that described in D1. $^1$H NMR (CDCl$_3$) δ: 0.96 (6H, t, J=7.6 Hz), 1.67-1.90 (4H, m), 2.33 (6H, s).

Description 20: (±){1-[Amino(phenyl)methyl]-1-ethylpropyl}dimethylamine

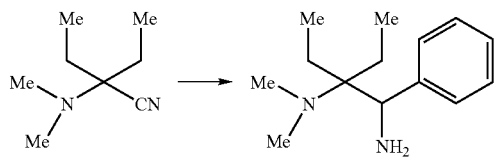

The title compound (11.12 g, 88%) was prepared from 2-(dimethylamino)-2-ethylbutanenitrile D19 (8.05 g, 0.0575 mol) and phenyllithium in dibutylether (64 ml of a 1.8M solution; 0.115 mol) in THF (350 ml), followed by reaction with sodium borohydride (3.9 g, 0.103 mol) in methanol (300 ml) in a similar manner to that described in D5. $^1$H NMR (CDCl$_3$) δ: 0.72 (3H, t, J=7.6 Hz), 0.97 (3H, t, J=7.6 Hz), 1.40-1.68 (4H, m), 1.70 (2H, br, m), 2.43 (6H, s), 4.09 (1H, s), 7.19-7.43 (5H, m).

Description 21:
2-Methyl-2-(1-pyrrolidinyl)butanenitrile

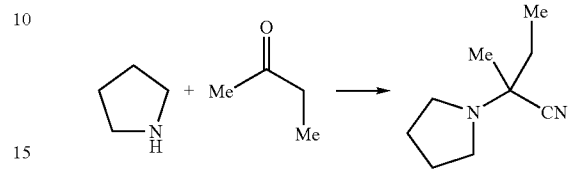

The title compound (9.6 g, 63%) was prepared from pyrrolidine (8.35 ml, 0.1 mol), 2-butanone (8.96 g, 0.1 mol) and potassium cyanide (6.51 g, 0.1 mol) in water (50 ml) in a similar manner to that described in D4. $^1$H NMR (CDCl$_3$) δ: 1.06 (3H, t, J=7.2 Hz), 1.45 (3H, s), 1.66-1.93 (6H, m), 2.70-2.75 (4H, m).

Description 22: (±)[2-Methyl-1-phenyl-2-(1-pyrrolidinyl)butyl]amine

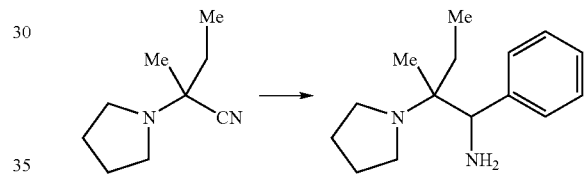

The title compound (13.4 g, 94%) was prepared from 2-methyl-2-(1-pyrrolidinyl)butanenitrile D21 (9.6 g, 0.063 mol) and phenyllithium in dibutylether (63 ml of a 2M solution; 0.126 mol) in THF (200 ml), followed by reaction with sodium borohydride (3.5 g, 0.092 mol) in methanol (200 ml) in a similar manner to that described in D5, except that after addition of the sodium borohydride stirring was continued with ice cooling for 0.5 hours then at room temperature for 66 hours. Mass spectrum (Electrospray LC/MS), ES$^+$: Found 233 (MH$^+$). C$_{15}$H$_{24}$N$_2$ requires 232. Ret. times 0.78 and 1.06 min.

Description 23:
2-(Dimethylamino)-2-methylbutanenitrile

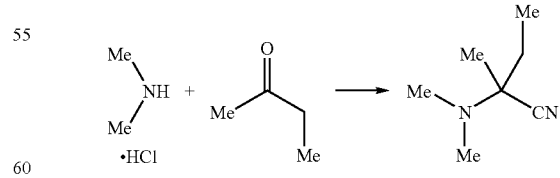

The title compound (9.95 g, 78%) was prepared from dimethylamine hydrochloride (8.15 g, 0.1 mol), 2-butanone (8.96 ml, 0.1 mol) and potassium cyanide (6.51 g, 0.1 mol) in water (50 ml) in a similar manner to that described in D1. $^1$H NMR (CDCl$_3$) δ: 1.00 (3H, t, J=7.2 Hz), 1.43 (3H, s), 1.75-1.87 (2H, m), 2.33 (6H, s).

Description 24: (±){1-[Amino(phenyl)methyl]-1-methylpropyl}dimethylamine

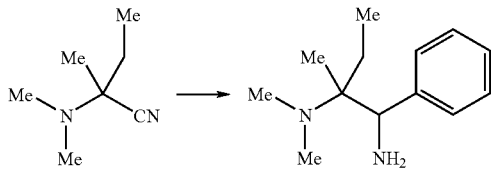

The title compound (15 g, 93%) was prepared from 2-(dimethylamino)-2-methylbutanenitrile D23 (9.9 g, 0.078 mol) and phenyllithium in dibutylether (87.3 ml of a 1.8M solution; 0.157 mol) in THF (400 ml), followed by reaction with sodium borohydride (5.25 g, 0.138 mol) in methanol (450 ml) in a similar manner to that described in D5. Mass spectrum (Electrospray LC/MS), ES⁺: Found 207 (MH⁺). $C_{13}H_{22}N_2$ requires 206. Ret. times 0.83 and 1.10 min.

Description 25: 2-Methyl-2-(2-methyl-1-pyrrolidinyl)propanenitrile

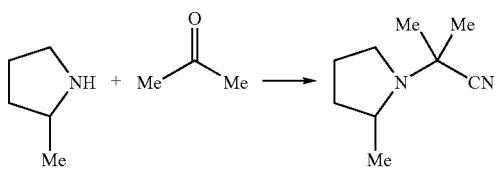

To a stirred, ice-cooled mixture of 2-(RS)-methylpyrrolidine (4.25 g; 0.05 mol) and acetone (3.67 ml; 0.05 mol) was added a solution of potassium cyanide (3.25 g; 0.05 mol) in water (25 ml) dropwise over 10 min. After stirring at room temperature overnight, the crude reaction mixture was extracted with diethyl ether (2×200 ml) and the combined extracts washed with brine (200 ml), dried (Na₂SO₄) and evaporated under reduced pressure to afford a pale yellow oil. This was dissolved in DCM and PS-Isocyanate (4.5 g of resin loading 1.53 mmol/g) added. The mixture was stirred for 3 hours, filtered and the filtrate evaporated to afford the title compound as a colourless semi-solid (2.82 g; 37.5%). ¹H NMR (CDCl₃) δ(inter alia): 1.10 (3H, d), 1.45 (3H, s), 1.55 (3H, s), 1.75-2.00 (4H, m) 2.65 (1H, m) and 3.05-3.20 (2H, m).

Description 26: (±)[2-Methyl-2-(2-methyl-1-pyrrolidinyl)-1-phenylpropyl]amine

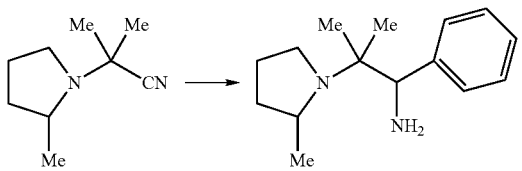

To a solution of 2-methyl-2-(2-methyl-1-pyrrolidinyl)propanenitrile D25 (2.82 g; 18.56 mmol) in THF (100 ml) at −70° C. under argon was added over 15 minutes a solution of phenyllithium in dibutylether (20.6 ml of a 1.8M solution; 37.11 mmol). The reaction mixture was stirred at −70° C. for 2 hours then allowed to warm to room temperature and stirred overnight. Saturated aqueous sodium hydrogen carbonate (100 ml) was added and stirring continued for a further 10 minutes. The mixture was extracted with diethyl ether (2×150 ml). Combined organics were dried (Na₂SO₄) and evaporated in vacuo. The residual yellow oil was dissolved in methanol (100 ml) and sodium borohydride (2.12 g; 0.056 mol) added portionwise over 5 minutes. The reaction mixture was stirred at room temperature for 4 hours, further sodium borohydride (1 g; 0.026 mol) added and the mixture heated at 60° C. for 1.5 hours. The mixture was cooled and excess sodium borohydride decomposed by dropwise addition of water. The reaction mixture was evaporated in vacuo and the residue partitioned between saturated sodium hydrogen carbonate (150 ml) and DCM (150 ml). Solid potassium carbonate was added and the aqueous layer extracted with DCM (150 ml) Combined organic extracts were dried (Na₂SO₄) and evaporated to give a green oil. This was divided into 8 portions and each portion passed down a 10 g SCX column. After washing each column with DCM, 50% DCM in methanol and methanol the product was eluted with 1 M ammonia in methanol to yield the title compound as a pale yellow oil (3.46 g: 80%). Mass spectrum (Electrospray LC/MS), ES⁺: Found 233 (MH⁺). $C_{15}H_{24}N_2$ requires 232. Ret. times 0.96 and 1.07 min.

Description 27: 1-[Methyl(phenylmethyl)amino]cyclopentanecarbonitrile

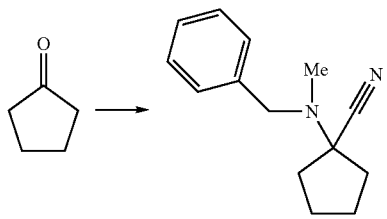

The title compound (15 g; 84%) was prepared from N-methylbenzylamine (10.08 g; 83 mmol), cyclopentanone (7 g; 83 mmol) and potassium cyanide (5.41 g; 83 mmol) in water (45 ml) in a similar manner to that described in D1. ¹H NMR (CDCl3) δ: 1.90 (6H, m), 2.20 (3H, s), 2.3 (2H, m), 3.62 (2H, s), 7.25 (1H, m), 7.32 (4H, m); Mass Spectrum (Electrospray LC/MS): Found 188 (MH⁺−HCN). $C_{14}H_{18}N_2$ requires 214. Ret. time 1.21 min.

Description 28: (±) -{1-[Amino(phenyl)methyl]cyclopentyl}methyl (phenylmethyl) amine

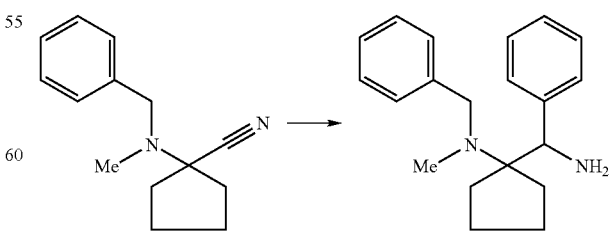

The title compound (3.90 g; 47%) was prepared from 1-[methyl(phenylmethyl)amino]cyclopentanecarbonitrile D28 (6.0 g; 28 mmol) and phenyllithium in di-n-butylether (16.21 ml of 1.9M solution; 30.8 mmol) in THF (60 ml), followed by reaction with sodium borohydride (3.2 g; 84 mmol) in methanol (60 ml) in a similar manner to that described in D2. Mass Spectrum (Electrospray LC/MS), API⁺: Found 295 (MH⁺). $C_{20}H_{26}N_2$ requires 294. Ret. time 2.12 min.

Description 29: (±)-{1-[Amino(phenyl)methyl]cyclopentyl}methylamine dihydrochloride

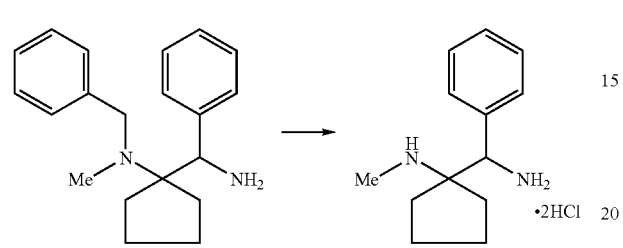

To a solution of (±)-{1-[amino(phenyl)methyl]cyclopentyl}methyl(phenylmethyl)amine D28 (0.5 g; 1.7 mmol) in ethanol was added 3N HCl (1 ml) and 10% palladium carbon (0.1 g). The catalytic hydrogenation was carried out for 16 h at room temperature and atmospheric pressure. The catalyst was filtered off through kieselguhr and the filtrate evaporated under reduced pressure to give the title compound (0.32 g; 69%). ¹H NMR (DMSO) δ: 1.3-2.2 (8H, m), 2.5 (3H, s), 4.6 (1H, s), 7.4 (3H, m), 7.6 (2H, m), 8.0 (2H, bs), 9.0 (1H, bs).

Description 30: (±)-2-Chloro-N-[{1-[(2-{[(1,1-dimethylethyl)(dimethyl)silyl]oxy}ethyl)(methyl)amino]cyclopentyl}(phenyl)methyl]-3-(trifluoromethyl)benzamide

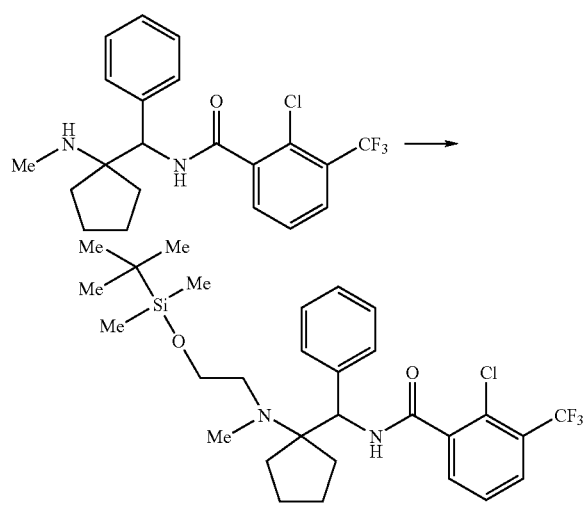

The title compound (0.390 g, 99%) was prepared from (±)-2-chloro-N-[[1-(methylamino)cyclopentyl](phenyl)methyl]-3-(trifluoromethyl)benzamide (0.282 g; 0.686 mmol), (tert-butyldimethylsilyloxy acetaldehyde (90%; 0.265 g; 1.52 mmol) and sodium triacetoxyborohydride (0.290 g; 1.52 mmol) in DCM (5 ml) in a similar manner to that described in E30. Mass Spectrum (Electrospray LC/MS). Found 569 (MH⁺). $C_{29}H_{40}{}^{35}ClF_3N_2O_2Si$ requires 568. Ret. time: 3.04 min.

Description 31: {1-[Amino(phenyl)methyl]cyclopentyl}methylamine Enantiomer 1 and Enantiomer 2

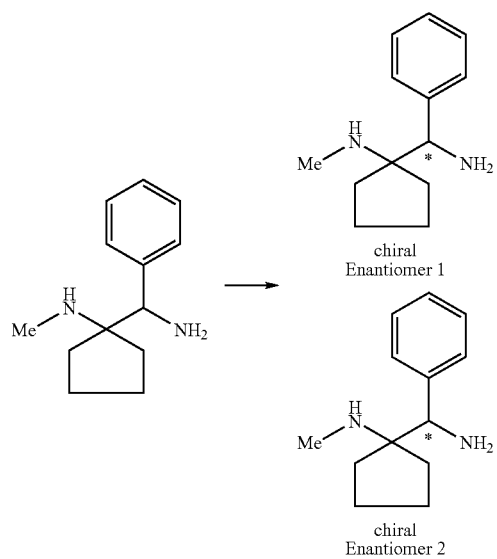

Racemic (±)-{1-[amino(phenyl)methyl]cyclopentyl}methylamine D29 (0.342 g; 1.67 mmol) was separated by preparative chiral HPLC to afford the title products enantiomer 1 (0.134 g); Chiral HPLC: 99.8% ee; ¹H NMR (CDCl₃) δ: 1.30-1.78 (11H, m), 2.33 (3H, s), 4.08 (1H, s), 7.22 (1H, m), 7.28 (2H, m), 7.35 (2H, m), and enantiomer 2 (0.127 g); Chiral HPLC: 99.8% ee; ¹H NMR (CDCl₃) δ: 1.30-1.78 (11H, m), 2.33 (3H, s), 4.08 (1H, s), 7.22 (1H, m), 7.28 (2H, m), 7.35 (2H, m).

Analytical HPLC Conditions:

| Column: | Chiral OD 10 micron particle size |
| --- | --- |
| | 20 mm i.d. × 250 mm |
| Mobile phase: | Heptane:Absolute Ethanol (90:10 v/v) |
| Gradient: | Isocratic |
| UV Wavelength: | 215 nm |
| Flow rate: | 1 ml/min |
| Ret. Time: | 7.5 min (Enantiomer 1); 15.6 min (Enantiomer 2) |

Preparative HPLC Conditions:

| Column: | Chiral OD 10 micron particle size |
| --- | --- |
| | 20 mm i.d. × 250 mm |
| Mobile phase: | Heptane:Absolute Ethanol (90:10 v/v) |
| Gradient: | Isocratic |
| UV Wavelength: | 215 nm |
| Flow rate: | 17 ml/min |

Description 32: 1-[Bis(phenylmethyl)amino]cyclopentanecarbonitrile

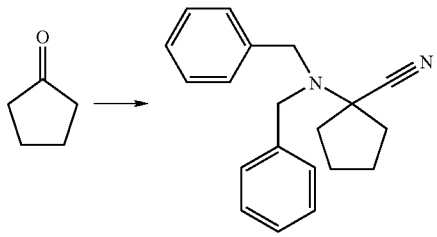

To an ice-cooled suspension of dibenzylamine hydrochloride (13.5 g; 0.058 mol) and cyclopentanone (4.86 g; 0.058 mol) in 25% ethanol in water (100 ml) was added ethanol (60 ml) and a solution of potassium cyanide (3.78 g; 0.058 mol) in water (35 ml) dropwise over 20 minutes with stirring. After 6 days the reaction mixture was extracted with ethyl acetate, washed with sodium bicarbonate solution, dried ($Na_2SO_4$) and evaporated in vacuo to afford the title compound as an off white solid (8.32 g, 49%). $^1$H NMR ($CDCl_3$) δ: 1.72 (6H, m), 2.12 (2H, m), 3.78 (4H, m), 7.1-7.3 (10H, m); Mass Spectrum (Electrospray LC/MS): Found 264 ($MH^+$–HCN). $C_{20}H_{22}N_2$ requires 290. Ret. time 1.88 min.

Description 33: (±)-{1-[Amino(phenyl)methyl]cyclopentyl}bis(phenylmethyl)amine

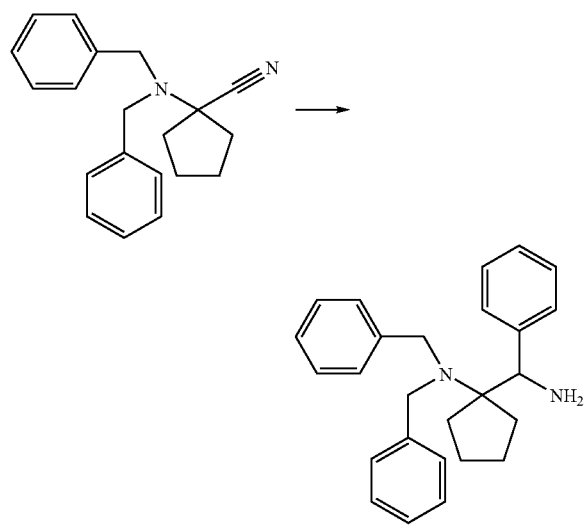

The title compound (2.31 g; 38%) was prepared from 1-[bis(phenylmethyl)amino]cyclopentanecarbonitrile D32 (4.0 g; 13.8 mmol), and phenyllithium in di-n-butylether (8.4 ml of 1.8M solution; 15.2 mmol) in THF (80 ml), followed by reaction with sodium borohydride (1.57 g; 41.4 mmol) in methanol (80 ml) in a similar manner to that described in D2. Mass Spectrum (Electrospray LC/MS), $API^+$: Found 371 ($MH^+$). $C_{26}H_{30}N_2$ requires 370. Ret. time 2.62 min.

Description 34: (±)-N-[{1-[bis(phenylmethyl)amino]cyclopentyl}(phenyl)methyl]-2,6-dimethylbenzamide

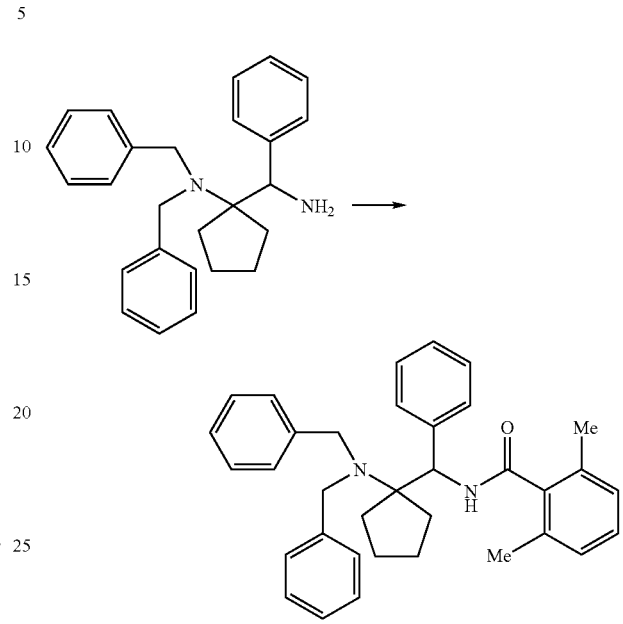

The title compound (2.51 g; 80%) was prepared from (±)-{1-[amino(phenyl)methyl]cyclopentyl}bis(phenylmethyl)amine D33 (2.31 g; 6.23 mmol), 2,6-dimethyl benzoyl chloride (1.15 g; 6.85 mmol), triethylamine (1.73 ml; 12.5 mmol) in DCM (70 ml) in a similar manner to that described in E13. $^1$H NMR (CDCl3) δ: 1.40-2.05 (8H, m), 2.28 (6H, s), 3.68 (4H, s), 5.37 (1H, d), 6.78 (1H, m), 6.95-7.36 (16H, m), 7.45 (2H, m); Mass Spectrum (Electrospray LC/MS), $API^+$: Found 503 ($MH^+$). $C_{35}H_{38}N_2O$ requires 502. Ret. time 3.77 min.

Description 35: 1-{Methyl[2-(methyloxy)ethyl]amino}cyclopentanecarbonitrile

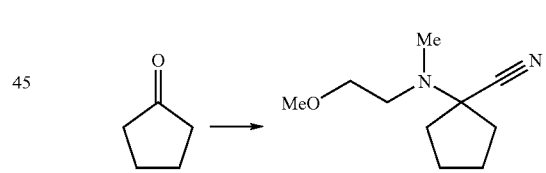

The title compound (3.39 g; 82%) was prepared from N-(2-methoxyethyl)methylamine hydrochloride (2.84 g; 22.6 mmol), cyclopentanone (1.90 g, 22.6 mmol) and potassium cyanide (1.47 g; 22.6 mmol) in water (15 ml) in a similar manner to that described in D1. $^1$H NMR ($CDCl_3$) δ: 1.83 (6H, m). 2.20 (2H, m), 2.48 (3H, s), 2.68 (2H, t), 3.46 (3H, s), 3.5 (2H, t).

Description 36: (±)-{1-[Amino(phenyl)methyl]cyclopentyl}methyl[2-(methyloxy)ethyl]amine

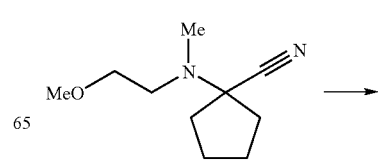

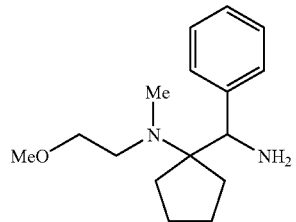

The title compound (1.22 g; 42%) was prepared from 1-{methyl[2-(methyloxy)ethyl]amino}cyclopentanecarbonitrile D35 (2.0 g; 11 mmol), and phenyllithium in di-n-butylether (6.7 ml of 1.8M solution; 12 mmol) in THF (25 ml), followed by reaction with sodium borohydride (1.25 g; 33 mmol) in methanol (25 ml) in a similar manner to that described in D2. Mass Spectrum (Electrospray LC/MS). Found 263 (MH$^+$). C$_{16}$H$_{26}$N$_2$O requires 262. Ret. time 1.57 min.

Description 37: 1-(2,5-Dihydro-1H-pyrrol-1-yl)cyclopentanecarbonitrile

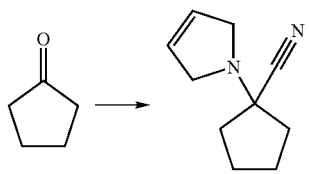

The title compound (2.8 g; 64%) was prepared from 3-pyrroline (1.86 g; 27 mmol), cyclopentanone (2.26 g; 27 mmol) and potassium cyanide (1.75 g; 27 mmol) in water (15 ml) in a similar manner to that described in D1. $^1$H NMR (CDCl3) δ: 1.85 (6H, m), 2.08 (2H, m), 3.61 (4H, s), 5.78 (2H, s).

Description 38: (±)-[[1-(2,5-Dihydro-1H-pyrrol-1-yl)cyclopentyl](phenyl)methyl]amine

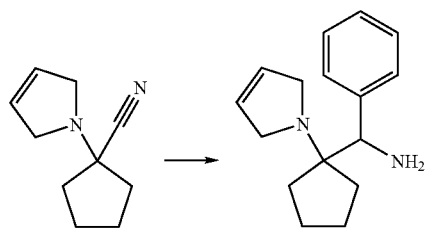

The title compound (1.35 g; 45%) was prepared from 1-(2,5-dihydro-1H-pyrrol-1-yl)cyclopentanecarbonitrile D37 (2.0 g; 12.3 mmol), and phenyllithium in di-n-butylether (7.5 ml of 1.8M solution; 13.5 mmol) in THF (20 ml), followed by reaction with sodium borohydride (1.402 g; 36.9 mmol) in methanol (20 ml) in a similar manner to that described in D2. Mass Spectrum (Electrospray LC/MS): Found 243 (MH$^+$). C$_{16}$H$_{22}$N$_2$ requires 242. Ret. time 1.02 min.

Description 39: (±)-1-(2-Methyl-1-pyrrolidinyl)cyclopentanecarbonitrile

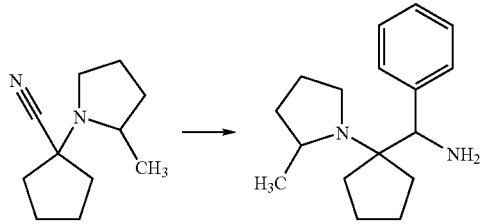

A mixture of cyclopentanone (1.34 g, 16 mmol) and 2-methylpyrrolidine (1.36 g; 16 mmol) was cooled to 0° C. (ice bath). A solution of potassium cyanide (1.04 g, 16 mmol) in water (10 ml) was added dropwise over 10 min and the whole mixture stirred vigorously for 18 h at 20° C., and then partitioned between ethyl acetate and water. The organic layer was dried (Na$_2$SO$_4$) and evaporated in vacuo to afford the title compound (2.24 g; 79%). $^1$NMR (CDCl3) δ: 1.1 (3H, d), 1.45 (1H, m), 1.75-2.05 (9H, m), 2.13 (2H, m), 2.65 (1H, m), 3.1 (2H, m).

Description 40: (±)-[[1-(2-methyl-1-pyrrolidinyl)cyclopentyl](phenyl)methyl]amine A solution of (±)-1-(2-methyl-1-pyrrolidinyl)cyclopentanecarbonitrile D39 (0.997 g; 5.6 mmol) in dry THF was cooled to −70° C. To this phenyllithium (1.7M in C6H14/ether, 1.1 equiv) was added slowly. The whole mixture was allowed to warm slowly to room temperature over 3 h with stirring under argon. Reaction cooled to 0° C. and methanol added followed by sodium borohydride (portionwise) and allowed to react at 20° C. overnight. The reaction was cooled to 0° C. and quenched with saturated sodium bicarbonate, extracted with ethyl acetate, dried (Na2SO4) and evaporated. The product was purified by chromatography on a 5 g SCX column eluting from 0-100% ethyl acetate in pet. ether, 0-10% methanol in ethyl acetate then 2% 0.880 ammonia in ethyl acetate to give the title compound as an oil (0.67 g; 46%) was obtained. Mass Spectrum (Electrospray LC/MS): Found 259 (MH$^+$). C$_{17}$H$_{26}$N$_2$ requires 258. Ret. time 1.19 min.

Description 41: 2-(Hexahydro-1H-azepin-1-yl)-2-methylpropanenitrile

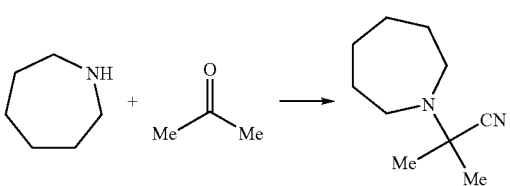

The title compound (6.6 g: 80%) was prepared from homopiperidine hydrochloride (6.7 g; 49 mmol), acetone (3.67 ml; 50 mmol), and potassium cyanide (3.25 g; 50 mmol) in water (25 ml) in a similar manner to that described in D1. ¹H NMR (CDCl₃) δ 1.43 (6H, s), 1.50-1.65 (8H, m), 2.66 (4H, m).

Description 42: (±)[2-(Hexahydro-1H-azepin-1-yl)-2-methyl-1-phenylpropyl]amine

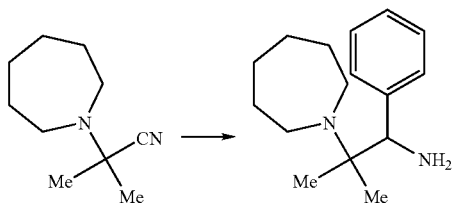

The title compound (3.7 g; 83%) was prepared from 2-(hexahydro-1H-azepin-1-yl)-2-methylpropanenitrile D41 (3 g; 18 mmol) and phenyllithium in dibutylether (18 ml of a 2M solution; 36 mmol) in THF (100 ml), followed by reaction with sodium borohydride (2.13 g, 54 mmol) in methanol (100 ml) in a similar manner to that described in D5. ¹H NMR (CDCl₃) δ 0.78 (3H, s), 0.98 (3H, s), 1.55-1.70 (8H, m), 1.83 (2H, br s), 2.67-2.79 (4H, m), 4.18 (1H, s), 7.20-7.30 (3H, m), 7.40-7.42 (2H, m).

Description 43: (±){1-[Amino(phenyl)methyl]cyclohexyl}dimethylamine

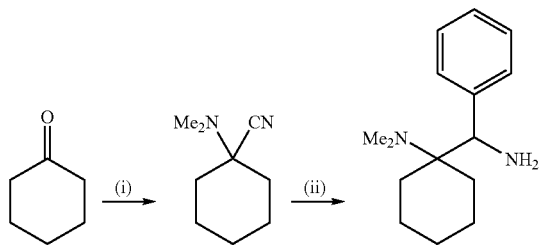

The title compound was prepared in two stages from (i) dimethylamine hydrochloride (3.26 g, 0.04 mol), cyclohexanone (3.9 g, 0.04 mol) and potassium cyanide (2.60 g, 0.04 mol) in water (25 ml) in a similar manner to that described in D1 to make 1-(dimethylamino)cyclohexanecarbonitrile (6.6 g, 100%). This was reacted directly in (ii) with phenyl lithium in dibutyl ether (10.5 ml of a 1.9M solution, 0.02 mol) in THF (30 ml) followed by sodium borohydride (1.51 g, 0.04 mol) in a similar manner to that described in D2 to afford the title compound (2.5 g, 36%). ¹H NMR (CDCl₃) δ: 0.85 (1H, m), 1.00 (1H, m), 1.25 (2H, m), 1.35-1.60 (6H, br m), 1.70 (1H, m), 2.10 (1H, m), 2.46 (6H, s), 4.15 (1H, s), 7.20-7.32 (5H, m).

Description 44: Dihydro-3(2H)-furanone

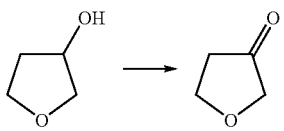

A mixture of 3-hydroxytetrahydrofuran (3.0 g, 0.034 mol) and pyridinium chlorochromate (14.7 g, 0.068 mol) in DCM (100 ml) was stirred at room temperature overnight. The title product was obtained by pouring the crude product through a silica pad using ethyl acetate as the eluent. The title product was obtained from 2 elutions (2.29 g; 79%). ¹H NMR (CDCl₃) δ: 2.50 (2H, t), 3.87 (2H, s), 4.26 (2H, t).

Description 45: (±)-3-(Dimethylamino)tetrahydro-3-furancarbonitrile

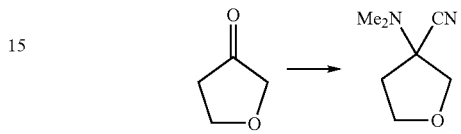

The title compound (6.54 g, 88%) was prepared from dihydro-3(2H)-furanone D44 (4.54 g, 0.053 mol), dimethylamine hydrochloride (4.9 g, 0.06 mol) and potassium cyanide (3.5 g, 0.054 mol) in water (100 ml) in a similar manner to that described in D1. ¹H NMR (CDCl₃) δ: 2.15 (1H, m), 2.33 (6H, s), 2.44 (1H, m), 3.69 (1H, d), 4.02-4.13 (2H, m), 4.17 (1H, m).

Description 46: (±){3-[Amino(phenyl)methyl]tetrahydro-3-furanyl}dimethylamine diastereoisomers

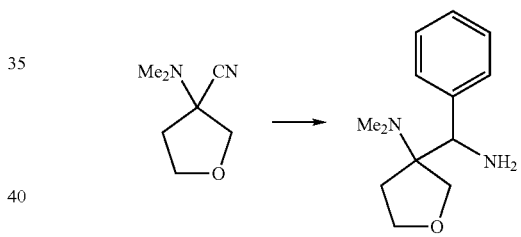

To a solution of 3-(dimethylamino)tetrahydro-3-furancarbonitrile D45 (4.55 g, 0.032 mol) in tetrahydrofuran (30 ml) at −70° C. under argon was added dropwise a solution of phenyllithium in dibutylether (36.1 ml of a 1.8M solution; 0.064 mol). The reaction mixture was stirred and maintained at −50 to −70° C. for 16 hours followed by careful addition of saturated aqueous sodium bicarbonate. The resulting slurry was extracted three times with DCM. The combined extracts were dried (Na₂SO₄) and evaporated to afford the crude product as an orange oil which was chromatographed on silica gel eluting with 0 to 100% ethyl acetate/pentane to afford the imine intermediate as a yellow oil (5.18 g). The oil was dissolved in methanol, sodium borohydride (1.8 g, 0.047 mol) added and the mixture stirred at room temperature overnight. The methanol was evaporated and the slurry partitioned between DCM and saturated aqueous sodium bicarbonate. The organics were dried by passage through a Phase-Sep column and evaporated to afford the title compound (3.47 g, 49%). ¹H NMR (CDCl₃) δ: 1.68 and 2.20 (1H, 2×m), 1.75 (2H, br s), 1.90 and 2.05 (1H, 2×m), 2.32 and 2.35 (6H, 2×s), 2.70 and 3.42 (1H, 2×m), 3.66-3.98 (3H, br m), 4.32 and 4.48 (1H, 2×s), 7.20-7.51 (5H, m).

Description 47: (±)2-(Dimethylamino)-3-{[(1,1-dimethylethyl)(dimethyl)silyl]oxy}-2-methylpropanenitrile

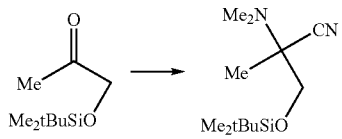

The title compound (2.16 g, 45%) was prepared from 1-(t-butyldimethylsilyloxy)-2-propanone (3.77 g, 0.02 mol), dimethylamine hydrochloride (1.71 g, 0.02 mol) and potassium cyanide (1.37 g, 0.02 mol) in water (50 ml) in a similar manner to that described in D1. An additional purification step was passage of the compound through SCX resin, elution with DCM to remove the starting material and then elution with 1 M ammonia in methanol to elute the title compound. $^1$H NMR (CDCl$_3$) δ: 0.00 (6H, d), 0.81 (9H, s), 1.38 (3H, s), 2.25 (6H, s), 3.36 (1H, d), 3.78 (1H, d).

Description 48: (±)[2-Amino-1-({[(1,1-dimethylethyl)(dimethyl)silyl]oxy}methyl)-1-methyl-2-phenylethyl]dimethylamine diastereoisomers

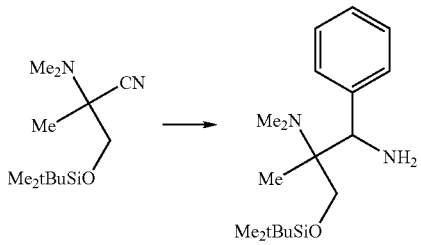

The title compound (930 mg, 33%) was prepared from 2-(dimethylamino)-3-{[(1,1-dimethylethyl)(dimethyl)silyl]oxy}-2-methylpropanenitrile D47 (2.1 g, 8.67 mmol), phenyl lithium (10.0 ml of a 1.8M solution in dibutyl ether, 18.0 mmol) in THF (30 ml) followed by sodium borohydride (830 mg, 26.0 mmol) in methanol (50 ml) in a similar manner to that described in D2. Chromatography (Biotage Horizon) to isolate the title compound was carried out using (i) 0 to 100% ethyl acetate/pentane, (ii) 100% ethyl acetate and (iii) 0 to 20% methanol/ethyl acetate. The product containing fractions were combined and evaporated. Mass spectrum (Electrospray LC/MS), API$^+$: Found 323 (MH$^+$), 306 (M−16). C$_{18}$H$_{34}$N$_2$OSi requires 322. Ret. time 2.35-2.39 min. (broad peak).

Description 49: (±)N-(2-(Dimethylamino)-3-{[(1,1-dimethylethyl)(dimethyl)silyl]oxy}-2-methyl-1-phenylpropyl)-2,3-dimethylbenzamide diastereoisomers

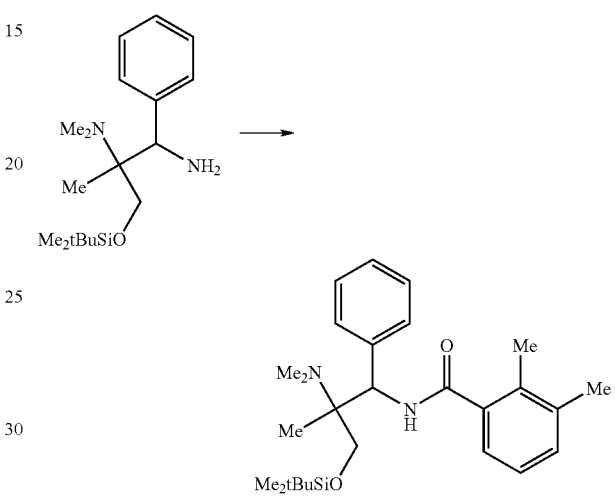

The title compound (64 mg; 30%) was prepared from [2-amino-1-({[(1,1-dimethylethyl)(dimethyl)silyl]oxy}methyl)-1-methyl-2-phenylethyl]dimethylamine D48 (150 mg; 0.46 mmol), 2,3-dimethylbenzoic acid (75 mg; 0.5 mmol), PL-dicyclohexylcarbodiimide (385 mg; 0.5 mmol; Polymer Labs 1.3 mmol/g), 1-hydroxybenzotriazole (77 mg; 0.5 mmol) in DCM (5 ml) in a similar manner to that described in E1. Mass spectrum (Electrospray LC/MS): Found 455 (MH$^+$), C$_{27}$H$_{42}$N$_2$O$_2$Si requires 454. Ret. time 2.57 and 2.61 min.

The compounds in Table 1 below were prepared in a manner similar to that described in description D49.

TABLE 1

| Description | Structure | Mass spectrum (Electrospray LC/MS), API$^+$ Ret. time (min) | Name |
|---|---|---|---|
| 50 | Me, Me, Si, O, Me, Me, N, Me, H, N, Me, O, Me (structure) | Found 455 (MH$^+$) C$_{27}$H$_{42}$N$_2$O$_2$Si requires 454; 2.60 and 2.62. | (±)-N-(2-(dimethylamino)-3-{[(1,1-dimethylethyl)(dimethyl)silyl]oxy}-2-methyl-1-phenylpropyl)-2,6-dimethylbenzamide diastereoisomers |

TABLE 1-continued

| Description | Structure | Mass spectrum (Electrospray LC/MS), API+ Ret. time (min) | Name |
|---|---|---|---|
| 51 | 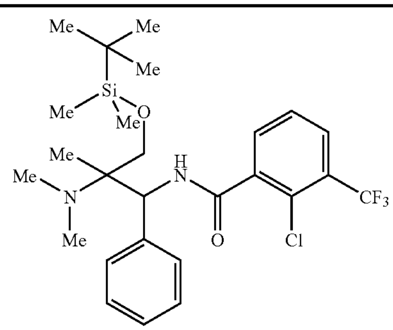 | Found 529 (MH+) $C_{26}H_{36}{}^{35}ClF_3N_2O_2$ Si requires 528; 2.72 and 2.79. | (±)-2-chloro-N-(2-(dimethylamino)-3-{[(1,1-dimethylethyl)(dimethyl)silyl]oxy}-2-methyl-1-phenylpropyl)-3-(trifluoromethyl)benzamide diastereoisomers |

Description 52:
2-Methyl-4,6-bis(trifluoromethyl)benzoic acid

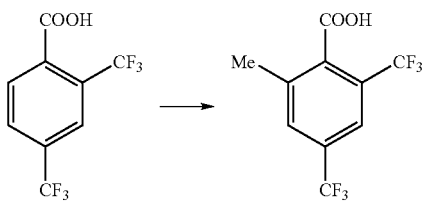

Dry THF (5 ml) was stirred under argon at −80° C. and treated with sec-butyl lithium (3.05 ml of a 1.4M solution in cyclohexane, 4.27 mmol) and N,N,N',N'-tetramethylethylenediamine (640 ul, 4.27 mmol). A solution of 2,4-bis(trifluoromethyl)benzoic acid (0.50 g, 1.94 mmol) in dry THF (2 ml) was added dropwise over 30 minutes and allowed to stir for a further 30 minutes at −80° C. Iodomethane (483 ul, 7.76 mmol) was added dropwise over 5 minutes and the reaction stirred at −70° C. for a further 20 minutes and allowed to warm to room temperature. Water (1 ml) was added dropwise and the mixture partitioned between ethyl acetate and water. The water layer was acidified with 2M hydrochloric acid and extracted twice with ethyl acetate. The combined extracts were dried over magnesium sulphate and evaporated to afford a crude solid (416 mg). NMR indicated this to be a mixture of 2-methyl-4,6-bis(trifluoromethyl)benzoic acid and recovered 2,4-bis(trifluoromethyl)benzoic acid. It was used without further purification.

Description 52:
2-Methyl-4,6-bis(trifluoromethyl)benzoic acid—Alternative method Dry THF (5 ml) was stirred under argon at −80° C. and treated with sec-butyl lithium (4.0 ml of a 1.4M solution in cyclohexane, 5.60 mmol) and N,N,N',N'-tetramethylethylenediamine (640 ul, 4.27 mmol). A solution of 2,4-bis(trifluoromethyl)benzoic acid (0.50 g, 1.94 mmol) in dry THF (2 ml) was now added dropwise over 30 minutes and allowed to stir for a further 30 minutes at −80° C. Iodomethane (483 ul, 7.76 mmol) was now added dropwise over 5 minutes and the reaction stirred at −70° C. for a further 20 minutes and allowed to warm to room temperature. Water (1 ml) was added dropwise and the mixture partitioned between ethyl acetate and water. The water layer was acidified with 2M hydrochloric acid and extracted twice with ethyl acetate. The combined extracts were dried over magnesium sulphate and evaporated to afford a crude solid (420 mg). NMR indicated this to be a mixture of 2-methyl-4,6-bis(trifluoromethyl)benzoic acid (ca. 80%), $^1$H NMR (CDCl$_3$) δ: 2.54 (3H, s), 7.73 (1H, s), 7.81 (1H, s), and recovered 2,4-bis(trifluoromethyl)benzoic acid (ca. 20%).

Description: 53:
2-Methyl-4,6-bis(trifluoromethyl)benzoyl chloride

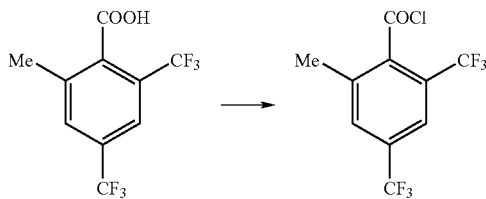

A solution of 2-methyl-4,6-bis(trifluoromethyl)benzoic acid D52 alternative method (400 mg, approximately 1.47 mmol) in DCM (5 ml), containing DMF (1 drop), was treated with oxalyl chloride (166 ul, 1.91 mmol) and stirred under argon for 1 hour. The solvent was carefully removed under reduced pressure and the residue re-evaporated from further DCM. The mixture of acid chlorides was then treated with methanol (3 ml) and kept at room temperature for 2 hours after which time the solvent was again carefully removed under reduced pressure. NMR data indicated this to be a mixture of the title product 2-methyl-4,6-bis(trifluoromethyl)benzoyl chloride and methyl 2,4-bis(trifluoromethyl)benzoate. The mixture was used without further purification.

Description: 54:
2-(Methylthio)-4,6-bis(trifluoromethyl)benzoic acid

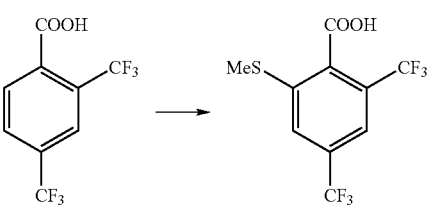

Dry THF (5 ml) was stirred under argon at −80° C. and treated with N,N,N',N'-tetramethylethylenediamine (640 ul, 4.27 mmol) followed by sec-butyl lithium (3.05 ml of a 1.4M solution in cyclohexane, 4.27 mmol). A solution of 2,4-bis(trifluoromethyl)benzoic acid (0.50 g, 1.94 mmol) in dry THF (2 ml) was now added dropwise over 15 minutes and allowed to stir for a further 60 minutes at −80° C. Dimethyldisulphide (687 ul, 7.76 mmol) was now added dropwise over 2 minutes and the reaction stirred at −80° C. for a further 40 minutes and allowed to warm to room temperature by cooling bath removal. Stirred at room temperature overnight. Water (1 ml) was added dropwise and the mixture partitioned between ethyl acetate and water. The water layer was acidified with 2M hydrochloric acid and extracted twice with ethyl acetate. The combined extracts were dried over magnesium sulphate and evaporated to afford a crude solid (400 mg). NMR indicated this to be a mixture of the title product 2-(methylthio)-4,6-bis(trifluoromethyl)benzoic acid and recovered 2,4-bis(trifluoromethyl)benzoic acid which was used without further purification.

Description: 55:
2-(Methylthio)-4,6-bis(trifluoromethyl)benzoyl chloride

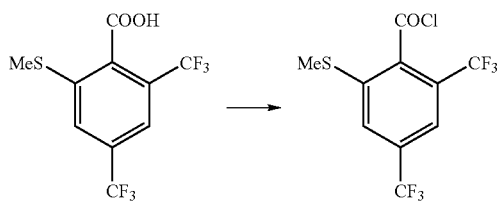

A solution of the mixture containing 2-(methylthio)-4,6-bis(trifluoromethyl)benzoic acid D54 (225 mg) in dry DCM (4 ml), containing dry DMF (1 drop), was treated with oxalyl chloride (87 ul, 1.0 mmol) and stirred at room temperature for 1 hour. The solvent was removed under reduced pressure to afford a crude product which was treated with dry methanol (2 ml) and stirred at room temperature overnight. The solvent was then carefully removed under reduced pressure. The residue was chromatographed on silica gel, eluting with 0-10% ethyl acetate in pentane to afford the title product 2-(methylthio)-4,6-bis(trifluoromethyl)benzoyl chloride (60 mg). $^1$H NMR (CDCl$_3$) δ: 2.62 (3H, s), 7.77 (1H, s), 7.82 (1H, s). Further elution gave methyl 2,4-bis(trifluoromethyl)benzoate (100 mg).

EXAMPLE 1

(±)-2,6-Dichloro-N-[[1-(dimethylamino)cyclopentyl](phenyl)methyl]benzamide

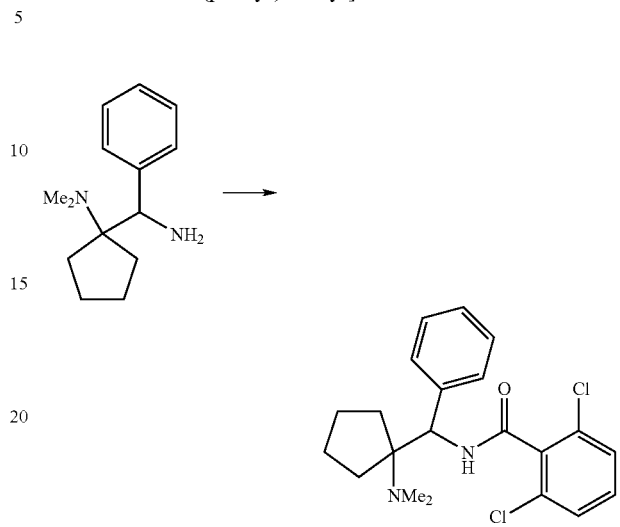

To a solution of 2,6-dichlorobenzoic acid (20 mg; 0.105 mmol) in DCM (2 ml) and N-methylpyrrolidinone (0.1-0.5 ml) was added 1-hydroxybenzotriazole (18 mg; 0.11 mmol) and PL-dicyclohexylcarbodiimide (88 mg; 0.14 mmol; Polymer Labs 1.59 mmol/g). The mixture was shaken at room temperature for 1 hour and then 1-[amino(phenyl)methyl]cyclopentyl}dimethylamine dihydrochloride D2 (20 mg; 0.07 mmol) and PS-diisopropylethylamine (82 mg; 0.21 mmol; Polymer Labs 2.59 mmol/g) were then added and shaking continued overnight at room temperature. An excess of PS-Trisamine was then added and after shaking for a further 4 h, the mixture was filtered and the resins washed well with DCM and methanol. The filtrate was reduced in volume by evaporation in vacuo and loaded onto an SCX cartridge (500 mg). Washing with DCM, then methanol followed by elution with 1M ammonia in methanol afforded the title product (22.8 mg). $^1$H NMR (CDCl$_3$) δ: 0.98 (1H, m), 1.26 (1H, m), 1.40 (2H, m), 1.68 (2H, m), 1.85 (2H, m), 2.22 (6H, s), 5.08 (1H, bs), 7.27 (7H, m), and 7.47 (2H, m). Mass Spectrum (Electrospray LC/MS): Found 391 (MH$^+$). C$_{21}$H$_{24}$$^{35}$Cl$_2$N$_2$O requires 390. Ret. time 1.88 min.

The compounds in Table 2 below were prepared using similar methods to that described for Example 1. Coupling method: P=Polymer-supported DCC

TABLE 2

| Ex | Structure | Method | Mass spectrum (Electrospray LC/MS), API$^+$ Ret. time (min) | Name |
| --- | --- | --- | --- | --- |
| 2 | 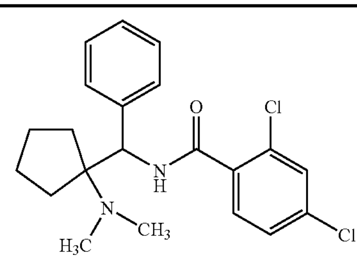 | P | Found 391 (MH$^+$) C$_{21}$H$_{24}$$^{35}$Cl$_2$N$_2$O requires 390; 2.03 | (±)-2,4-Dichloro-N-[[1-(dimethylamino)cyclopentyl](phenyl)methyl]benzamide |

TABLE 2-continued

| Ex | Structure | Method | Mass spectrum (Electrospray LC/MS), API+ Ret. time (min) | Name |
|---|---|---|---|---|
| 3 | 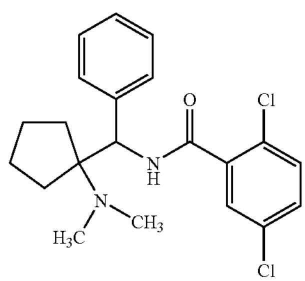 | P | Found 391 (MH+) $C_{21}H_{24}{}^{35}Cl_2N_2O$ requires 390; 2.01 | (±)-2,5-Dichloro-N-[[1-(dimethylamino)cyclopentyl](phenyl)methyl]benzamide |
| 4 | 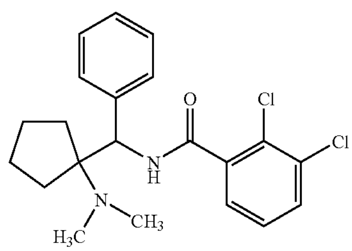 | P | Found 391 (MH+) $C_{21}H_{24}{}^{35}Cl_2N_2O$ requires 390; 2.02 | (±)-2,3-Dichloro-N-[[1-(dimethylamino)cyclopentyl](phenyl)methyl]benzamide |
| 5 | 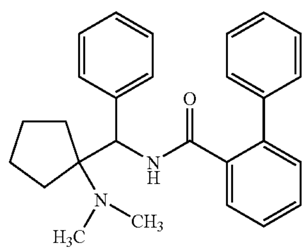 | P | Found 399 (MH+) $C_{27}H_{30}N_2O$ requires 398; 2.13 | (±)-N-[[1-(Dimethylamino cyclopentyl)(phenyl)methyl]-2-biphenylcarboxamide |
| 6 | 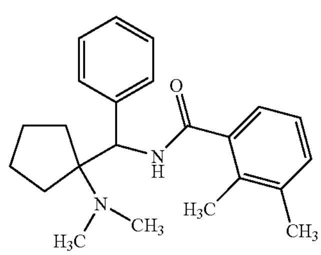 | P | Found 351 (MH+) $C_{23}H_{30}N_2O$ requires 350; 1.96 | (±)-N-[[1-(Dimethylamino)cyclopentyl](phenyl)methyl]-2,3-dimethylbenzamide |
| 7 | 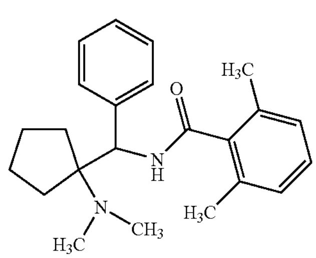 | P | Found 351 (MH+) $C_{23}H_{30}N_2O$ requires 350; 1.87 | (±)-N-[[1-(Dimethylamino)cyclopentyl](phenyl)methyl]-2,6-dimethylbenzamide |

TABLE 2-continued

| Ex | Structure | Method | Mass spectrum (Electrospray LC/MS), API+ Ret. time (min) | Name |
|---|---|---|---|---|
| 8 | 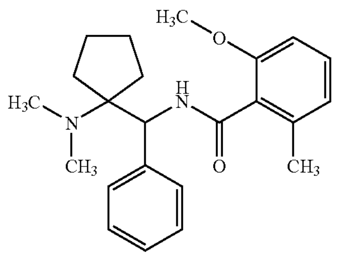 | P | Found 367 (MH+) $C_{23}H_{30}N_2O_2$ requires 366; 1.80 | (±)-N-[[1-(Dimethylamino)cyclopentyl](phenyl)methyl]-2-methyl-6-(methyloxy)benzamide |
| 9 | 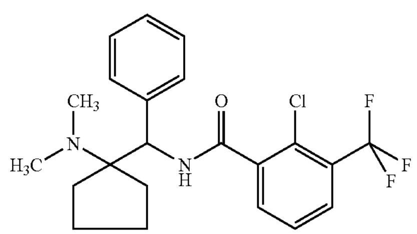 | P | Found 425 (MH+) $C_{22}H_{24}{}^{35}ClF_3N_2O$ requires 424; 2.16 and 2.19. | (±)-2-Chloro-N-[[1-(dimethylamino)cyclopentyl](phenyl)methyl]-3-(trifluoromethyl)benzamide |

EXAMPLE 10

2-Chloro-N-[[1-(dimethylamino)cyclopentyl](phenyl)methyl]-3-(trifluoromethyl)benzamide enantiomer 2

Racemic 2-chloro-N-[[1-(dimethylamino)cyclopentyl](phenyl)methyl]-3-(trifluoro methyl)benzamide E9 (250 mg; 0.59 mmol) was separated by semi-preparative chiral HPLC to afford the title product enantiomer 1 (82 mg); Chiral HPLC>99.8% ee; and the title product enantiomer 2 (86 mg); Chiral HPLC>99.8% ee.

Semi-Preparative Chromatography Conditions

| | |
|---|---|
| Column: | chiralpak AD-H 5 um, 250 × 21 mm |
| Mobile phase: | A: n-Hexane; B: Isopropanol + 0.1% isopropylamine |
| Gradient: | isocratic 15% B |
| Flow rate: | 7 ml/min |
| UV wavelength range: | 225 nm |
| Analysis time: | 45 min |

Analytical Chromatography Conditions

| | |
|---|---|
| Column: | chiralpak AD-H 5 um, 250 × 4.6 mm |
| Mobile phase: | A: n-Hexane; B: Isopropanol |
| Gradient: | isocratic 15% B |
| Flow rate: | 1 ml/min |
| UV wavelength range: | 200-400 nm |
| Analysis time: | 25 min |
| Ret. Time: | 6.5 min (Enantiomer 1); 10.1 min (Enantiomer 2) |

EXAMPLE 11

N-[[1-(Dimethylamino)cyclopentyl](phenyl)methyl]-2,3-dimethyl benzamide chiral

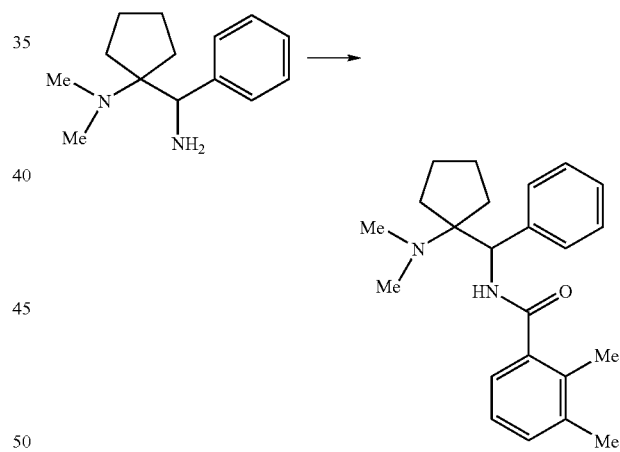

A mixture of {1-[amino(phenyl)methyl]cyclopentyl}dimethylamine D3 enantiomer 2 (0.102 g, 0.47 mmol), 2,3-dimethylbenzoic acid (0.100 g, 0.67 mmol), 1-hydroxybenzotriazole hydrate (0.092 g, 0.6 mmol) and PS-DCC (0.63 g of 1.3 mmol/g loading, 0.82 mmol) in DCM (7 ml) was shaken for 20 h. The mixture was filtered and the resin washed with DCM (2×4 ml). Combined organics were washed with saturated sodium hydrogen carbonate (20 ml), the layers separated and the organic layer applied to a 2 g SCX cartridge. The cartridge was washed with DCM (2 volumes), 50% methanol in DCM (1 volume) and methanol (2 volumes). Elution with 1M ammonia in methanol (2 volumes) and evaporation of the solvent afforded a colourless gum. Chromatography on silica gel (10 g) eluting with 0-100% ethyl acetate in pentane gradient afforded the title compound as a colourless solid (0.14 g; 86%). $^1$H NMR (CDCl$_3$) δ: 0.90-1.15 (1H, m), 1.20-1.38 (1H, m), 1.40-1.55 (2H, m), 1.60-

1.75 (2H, m), 1.79-1.90 (2H, m), 2.22 (6H, s), 2.28 (6H, s), 5.15 (1H, d, J=6 Hz), 6.98 (1H, d, J=6 Hz), 7.10-7.15 (1H, m), 7.19-7.27 (3H, m), 7.29-7.35 (2H, m), 7.39-7.43 (2H, m). Mass spectrum (Electrospray LC/MS), ES+: Found 351 (MH+). $C_{23}H_{30}N_2O$ requires 350. Ret. time 1.90 min. The title product was converted to the corresponding hydrochloride salt (0.150 g).

EXAMPLE 12

N-[[1-(Dimethylamino)cyclopentyl](phenyl)methyl]-2-methyl-6-(methyloxy)benzamide chiral

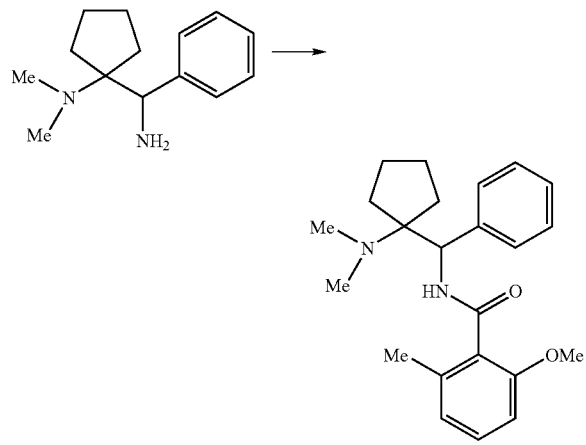

A mixture of {1-[amino(phenyl)methyl]cyclopentyl}dimethylamine D3 enantiomer 2 (0.220 g, 1 mmol), 2-methoxy-6-methylbenzoic acid (0.200 g, 1.2 mmol), 1-hydroxybenzotriazole hydrate (0.183 g, 1.2 mmol) and PS-DCC (1 g of 1.3 mmol/g loading, 1.3 mmol) in DCM (10 ml) was stirred vigorously overnight. The mixture was washed with saturated aqueous sodium hydrogen carbonate, the layers separated through a phase separation cartridge and the organic layer applied to an SCX cartridge. The cartridge was eluted with DCM (×2), and then methanol (×2) followed by 1M ammonia in methanol. Evaporation of the solvent afforded the title compound which was characterised. $^1$H NMR (CDCl$_3$) δ: 1.00-1.10 (1H, m), 1.25-1.40 (1H, m), 1.40-1.60 (2H, m), 1.60-1.80 (2H, m), 1.80-2.00 (2H, m), 2.24 (6H, s), 2.28 (3H, s), 3.80 (3H, s), 5.17 (1H, d, J=6 Hz), 6.75 (1H, d, J=8 Hz), 6.79 (1H, d, J=8 Hz), 7.10 (1H, br s), 7.15-7.30 (4H, m), 7.44 (2H, m). Mass Spectrum (Electrospray LC/MS): Found 367 (MH+). $C_{23}H_{30}N_2O_2$ requires 366. Ret. time 1.92 min. The title product was converted to the corresponding hydrochloride salt (0.34 g, 85%).

EXAMPLE 13

N-[[1-(Dimethylamino)cyclopentyl](phenyl)methyl]-2,6-dimethyl benzamide chiral

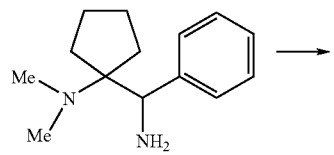

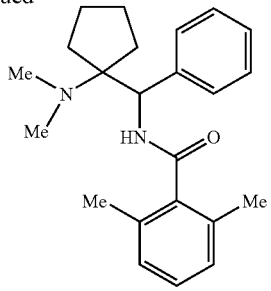

A solution of 2,6-dimethylbenzoyl chloride (1.7 g, 10.1 mmol) in DCM (10 ml) was added dropwise to a mixture of {1-[amino(phenyl)methyl]cyclopentyl}dimethylamine D3 enantiomer 2 (2.0 g, 9.2 mmol), and triethylamine (1.4 ml, 10.0 mmol) in DCM (40 ml) and stirred at room temperature for 2 h. The mixture was washed with saturated aqueous sodium hydrogen carbonate, the organic layer was separated through a phase separation cartridge and then evaporated to a white solid. Chromatography with eluent 50-100% ethyl acetate/pentane, then 0-10% methanol/ethyl acetate afforded the title product as a white solid (3.1 g, 97%). $^1$H NMR (CDCl$_3$) δ: 0.85-1.00 (1H, m), 1.30-1.55 (3H, m), 1.60-1.75 (2H, m), 1.78-1.90 (2H, m), 2.21 (6H, s), 2.31 (6H, s), 5.19 (1H, d, J=6 Hz), 6.79 (1H, br d), 7.02 (2H, d, J=8 Hz), 7.16 (1H, t, J=8 Hz), 7.20-7.35 (3H, m), 7.43 (2H, m). Mass Spectrum (Electrospray LC/MS): Found 351 (MH+). $C_{23}H_{30}N_2O$ requires 350. Ret. time 2.0 min. The white solid product was converted to the HCl salt using 1M HCl/diethylether to afford the salt as a white solid on evaporation.

EXAMPLE 13b

Succinate salt of N-[[1-(dimethylamino)cyclopentyl](phenyl)methyl]-2,6-dimethyl benzamide chiral To a mixture of 26.25 g of the free base of the compound of Example 13 and 9.286 g of succinic acid, was added 262 ml of IPA (isopropyl alcohol) under nitrogen and the mixture was stirred at room temperature for 12 hours. Then the mixture was heated at 40° C. for 1 hour, cooled at room temperature and chilled at 0° C. for 1 hour. After further 30 min at room temperature the solid is collected by filtration, dried overnight at 45° C. under vacuum to get 31.92 g of title material as a white solid.

EXAMPLE 13c

Formulation of N-[[1-(dimethylamino)cyclopentyl](phenyl)methyl]-2,6-dimethyl benzamide chiral 10.6 mg of N-[[1-(Dimethylamino)cyclopentyl](phenyl)methyl]-2,6-dimethyl benzamide was dissolved in 7 ml of Miglyol 812N. 217.1 mg of Methocel K4M was added and the suspension was homogenised with a high shear mixer. The resulting concentrations were 1.5 mg ml$^{-1}$ of active ingredient and 30 mg ml$^{-1}$ of Methocel excipient.

EXAMPLE 14

N-[[1-(Dimethylamino)cyclopentyl](phenyl)methyl]-4-fluoro-2,6-dimethylbenzamide chiral

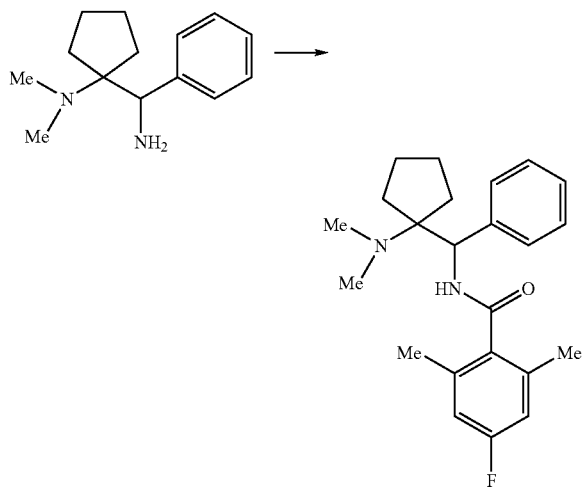

To {1-[amino(phenyl)methyl]cyclopentyl}dimethylamine D3 enantiomer 2 (0.904 g; 4.147 mmol) in DCM (45 ml) under argon at room temperature was added triethylamine (0.573 ml; 4.15 mmol), followed by a solution of 4-fluoro-2,6-dimethylbenzoyl chloride (0.773 g; 4.144 mmol) in DCM (5 ml). After 16 h. the reaction was washed with water, dried with MgSO$_4$ and evaporated. The residue was chromatographed on silica gel eluting with an ethyl acetate-hexane 0 to 100% gradient to give the title compound (1.57 g; 100%). $^1$H NMR (CDCl$_3$) δ: 0.85-1.00 (1H, m), 1.30-1.60 (3H, m), 1.60-1.75 (2H, m), 1.75-1.90 (2H, m), 2.22 (6H, s), 2.31 (6H, m), 5.18 (1H, d, J=6 Hz), 6.73 (2H, d, J=9.6 Hz overlaps 1H, br s), 7.20-7.35 (3H, m), 7.42 (2H, m). Mass Spectrum (Electrospray LC/MS): Found 369 (MH$^+$). C$_{23}$H$_{29}$FN$_2$O requires 368. Ret. time 1.99 min. The free base was dissolved in methanol. 1M HCl/diethylether was added to the stirred solution and stirring continued at room temperature for 5 minutes. The solution was then evaporated under reduced pressure, redissolved in DCM and evaporated at reduced pressure. The resulting foam was dried for 16 hours at reduced pressure. The hydrochloride salt was obtained as a white foam (1.45 g).

EXAMPLE 15

2-(Methyloxy)-N-[2-methyl-1-phenyl-2-(1-pyrrolidinyl)propyl]-4,6-bis(trifluoromethyl)benzamide chiral

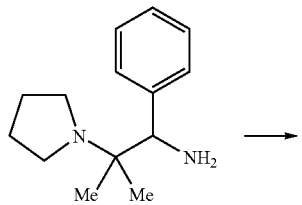

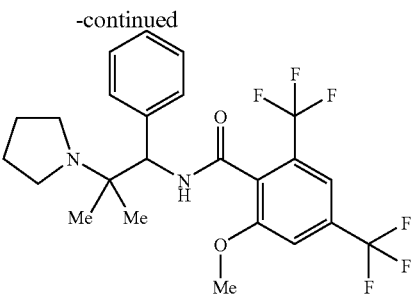

To a solution of diisopropylethylamine (0.915 ml; 5.37 mmol), 2,4-ditrifluoromethyl-6-methoxy-benzoic acid (0.511 g; 1.78 mmol) and (+)-[2-methyl-1-phenyl-2-(1-pyrrolidinyl)propyl]amine D6 (0.501 g; 1.74 mmol) in DMF (50 ml) under argon was added HATU (0.676 g; 1.78 mmol) portionwise. After stirring at room temperature for 3 h., followed by standing for ca. 2 days the reaction mixture was purified using an SCX column and the resulting product partitioned between ethyl acetate and water. The solvent was removed in vacuo to afford the title product. $^1$H NMR (CDCl$_3$) δ: 0.94 (6H, s), 1.60-1.80 (4H, m), 2.55-2.75 (4H, m), 3.89 (3H, s), 4.78 (1H, s), 7.20-7.40 (7H, m), 7.52 (1H, s). Mass Spectrum (Electrospray LC/MS): Found 489 (MH$^+$). C$_{24}$H$_{26}$F$_6$N$_2$O$_2$ requires 488. Ret. time 2.06 min. Conversion of the title product to the corresponding hydrochloride salt afforded an off-white solid (0.893 g; 96%).

EXAMPLE 15b 2-(Methyloxy)-N-[2-methyl-1-phenyl-2-(1-pyrrolidinyl)propyl]-4,6-bis(trifluoromethyl)benzamide hydrochloride chiral alternative method Step 1: (±)[2-Methyl-1-phenyl-2-(1-pyrrolidinyl)propyl]amine (D5)

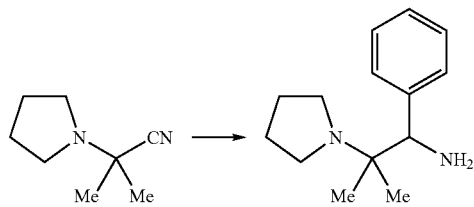

To a solution of 2-methyl-2-(1-pyrrolidinyl)propanenitrile D4 (40 g; 289.85 mmol) in dry THF (0.8 L) under nitrogen, cooled at −78° C., was added dropwise a solution of phenyl lithium in dibutyl ether over 40 minutes (305.1 mL of a 1.9M solution; 579.70 mmol). After 2 h the reaction was allowed to reach room temperature and then stirred overnight at this temperature. The mixture was quenched at 0° C. with a saturated solution of NaHCO$_3$ (0.8 L) and stirred for 15 minutes and diluted with water (ca. 0.6 L). The phases were separated and the aqueous back extracted with diethylether (2×1 L). The collected organics were dried over Na$_2$SO$_4$ and evaporated in vacuo to get 90 g of crude material as a yellow oil that was dissolved in methanol (1 L) at 0° C. and treated portionwise with sodium borohydride (21.93 g; 579.70 mmol). After 1 hour at 0° C. and then overnight at room temperature the mixture was cooled and quenched with water (ca. 0.5 L). Methanol was evaporated in vacuo and the aqueous phase, diluted with water (200 mL), was extracted with DCM (3×800 mL). The collected organics were dried over Na₂SO₄ and evaporated in vacuo to get the title product (51 g) as a yellow solid, used in step 2 without further purification.

Step 2: [2-Methyl-1-phenyl-2-(1-pyrrolidinyl)propyl]amine R(−)α methoxy phenyl acetic acid salt

[2-Methyl-1-phenyl-2-(1-pyrrolidinyl)propyl]amine D5 from step 1 (51 g; 234 mmol) was dissolved in isopropanol (0.765 L, 15 volumes, relative volumes being referred to the quantity of [2-methyl-1-phenyl-2-(1-pyrrolidinyl)propyl] amine). To this stirred solution, heated at 50° C., was added a solution of R(−)α methoxy phenyl acetic acid (38.83 g; 234 mmol) in isopropanol (0.255 L, 5 volumes, relative volumes being referred to the quantity of [2-methyl-1-phenyl-2-(1-pyrrolidinyl)propyl]amine). After 1.5 h the mixture was cooled to room temperature and then left stirring at this temperature overnight. The solid was recovered by filtration and washed with cold isopropanol. This solid (40.5 g) was suspended in isopropanol (0.648 L, 16 volumes, relative volumes being referred to the quantity of solid obtained in the last filtration step), and heated at 60° C. for 2 h, at room temperature overnight and recovered by filtration. This solid (38.5 g) was suspended in isopropanol (0.616 L, 16 volumes, relative volumes being referred to the quantity of solid obtained in the last filtration step), and heated at 60° C. for 2 h and at room temperature overnight, then recovered by filtration. This solid (37.8 g) was suspended in isopropanol (0.756 L, 20 volumes, relative volumes being referred to the quantity of solid obtained in the last filtration step), and heated at 60° C. for 2 h and at room temperature overnight, then recovered by filtration. This solid (36.5 g) was suspended in isopropanol (0.912 L, 25 volumes, relative volumes being referred to the quantity of solid obtained in the last filtration step), and heated at 60° C. for 2 h and then filtered at room temperature. This solid (34 g) was suspended in isopropanol (0.850 L, 25 volumes, relative volumes being referred to the quantity of solid obtained in the last filtration step), and heated at 60° C. for 2 h and filtered at room temperature. This solid (31.5 g) was suspended in isopropanol (0.787 L, 25 volumes, relative volumes being referred to the quantity of solid obtained in the last filtration step), and heated at 60° C. for 2 h, cooled down to 40° C. and then filtered to get the title material (27 g) as a white solid.

Step 3: 2-(Methyloxy)-4,6-bis(trifluoromethyl)benzoyl chloride

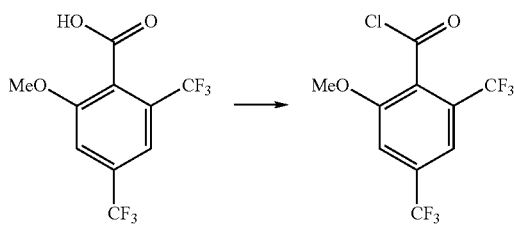

To a solution of 2-(methyloxy)-4,6-bis(trifluoromethyl) benzoic acid (20.2 g; 70.14 mmol) in dry DCM (400 mL), at 0° C., was added dropwise oxalyl chloride (13.4 mL; 154.31 mmol) followed by dry DMF (5 drops). The reaction was allowed to reach room temperature. After overnight stirring the solvent was evaporated in vacuo to get the title product (23.5 g) as a yellow slurry used without further purification.

Step 4: 2-(Methyloxy)-N-[2-methyl-1-phenyl-2-(1-pyrrolidinyl)propyl]-4,6-bis(trifluoromethyl)benzamide chiral (E15)

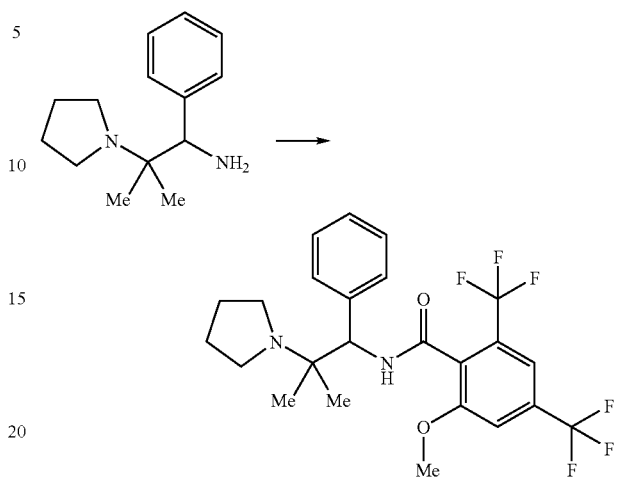

[2-Methyl-1-phenyl-2-(1-pyrrolidinyl)propyl]amine R(−)α methoxy phenyl acetic acid salt from step 2 (22 g; 57.3 mmol) was suspended in DCM at 0° C., treated with 1M NaOH solution (86 mL) and stirred at room temperature for 20 minutes. To the mixture water (250 mL) was added, the phases separated and the aqueous one extracted with DCM (2×300 mL). The collected organics were dried over Na₂SO₄ and evaporated in vacuo to get 12.3 g of white solid that was diluted with dry DCM (200 mL) under nitrogen and cooled at 0° C. To this solution was added triethylamine (23.92 mL; 172 mmol) and a solution of 2-(methyloxy)-4,6-bis(trifluoromethyl)benzoyl chloride from Step 3 in dry DCM (190 ml of a 200 mL solution in DCM of the step 3 material) over 30 minutes. The reaction was left stirring at room temperature for 2 hours and then quenched with a saturated solution of NaHCO₃ (ca. 450 mL). The phases were separated and the organic one washed with water (500 mL), dried over Na₂SO₄ and evaporated in vacuo to get crude material that was purified by silica gel flash chromatography eluting with DCM/ methanol 97/3. Evaporation of the solvent afforded the title material (26 g) as a pale yellow solid.

Step 5: 2-(Methyloxy)-N-[2-methyl-1-phenyl-2-(1-pyrrolidinyl)propyl]-4,6-bis(trifluoromethyl)benzamide hydrochloride chiral 2-(Methyloxy)-N-[2-methyl-1-phenyl-2-(1-pyrrolidinyl) propyl]-4,6-bis(trifluoromethyl)benzamide E15 from step 4 (10 g; 20.47 mmol) was dissolved in dry ethyl ether (200 mL), cooled to 0° C. and treated with 1M solution of HCl in ethyl ether (21.5 mL; 21.49 mmol). After 0.5 h the solid was collected by filtration, washed with diethyl ether and dried at 45° C. overnight to get the title material (9.1 g) as a pale yellow solid.

EXAMPLE 16

2-Bromo-N-[[1-(dimethylamino)cyclopentyl](phenyl)methyl]-6-methylbenzamide chiral

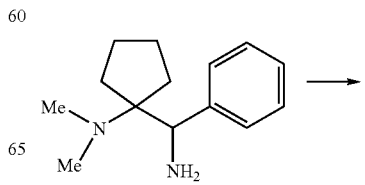

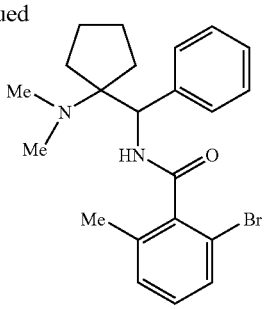

To {1-[amino(phenyl)methyl]cyclopentyl}dimethylamine D3 enantiomer 2 (50 mg, 0.23 mmol) in DCM (5 ml) was added 2-bromo-6-methylbenzoic acid (108 mg; 0.5 mmol), followed by 1-hydroxybenzotriazole (45 mg; 0.3 mmol) and PS-DCC (400 mg of 1.3 mmol/g loading, 0.52 mmol) and the mixture shaken at room temperature for ca. 2 days. The reaction mixture was filtered through a phase-separation cartridge and the filtrate stirred with saturated aqueous sodium bicarbonate for 30 min. The lower layer was removed, passed through another phase-separation cartridge and loaded onto an SCX cartridge which was eluted with 2 column volumes each of DCM, 50% methanol-DCM, methanol and 1M ammonia in methanol. The product containing fractions were evaporated to afford the title product (82 mg; 82%). 1H NMR (CDCl3) δ: 0.95-1.10 (2H, m), 1.40-1.60 (2H, m), 1.60-1.80 (2H, m), 1.80-1.90 (2H, m), 2.23 (6H, s), 2.33 (3H, m), 5.13 (1H, d J=6 Hz), 6.97 (1H, br s), 7.10-7.15 (2H, m), 7.24-7.34 (3H, m), 7.38-7.41 (1H, m), 7.46-7.48 (2H, m). Mass Spectrum (Electrospray LC/MS): Found 415 (MH$^+$). $C_{22}H_{27}{}^{79}BrN_2O$ requires 414. Ret. time 1.93 min.

EXAMPLE 17

4-Chloro-2-methyl-N-[2-methyl-1-phenyl-2-(1-pyrrolidinyl)propyl]-6-(methylthio)benzamide chiral

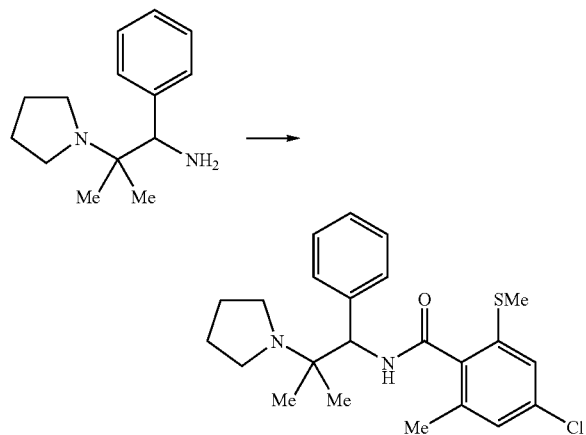

A mixture of (+)-[2-methyl-1-phenyl-2-(1-pyrrolidinyl)propyl]amine D6 (262 mg; 1.2 mmol), 4-chloro-2-methyl-6-(methylthio)benzoic acid (388 mg; 1.8 mmol), 1-hydroxybenzotriazole hydrate (276 mg; 1.8 mmol) and EDC (345 mg; 1.8 mmol) in DCM (16 ml) was stirred for 16 h. The reaction mixture was then partitioned between DCM and saturated aqueous sodium hydrogen carbonate and the organic layer separated, washed with brine, dried and evaporated. The residue was chromatographed on silica gel eluting with an ethyl acetate-hexane 0 to 100% gradient to give the title compound as a colourless oil (332 mg; 66%). $^1$H NMR (CDCl$_3$) δ: 0.90 (3H, s), 0.98 (3H, s), 1.66-1.75 (4H, m), 2.31 (3H, s), 2.44 (3H, s), 2.60-2.65 (2H, m), 2.69-2.74 (2H, m), 4.82 (1H, d J=3 Hz), 7.00 (1H, m), 7.09 (1H, m), 7.11 (1H, br s), 7.23-7.33 (3H, m), 7.41-7.43 (2H, m). Mass Spectrum (Electrospray LC/MS): Found 417 (MH$^+$). $C_{23}H_{29}{}^{35}ClN_2OS$ requires 416. Ret. time 2.08 min. The product was dissolved in methanol and 1M HCl/diethylether solution was added dropwise to the stirred solution. After stirring at room temperature for 5 minutes, the mixture was evaporated at reduced pressure. It was redissolved in DCM and evaporated again at reduced pressure to yield the hydrochloride salt as a white foam (320 mg).

EXAMPLE 18

N-[[1-(Dimethylamino)cyclopentyl](phenyl)methyl]-2-(methyloxy)-4,6-bis(trifluoromethyl)benzamide chiral

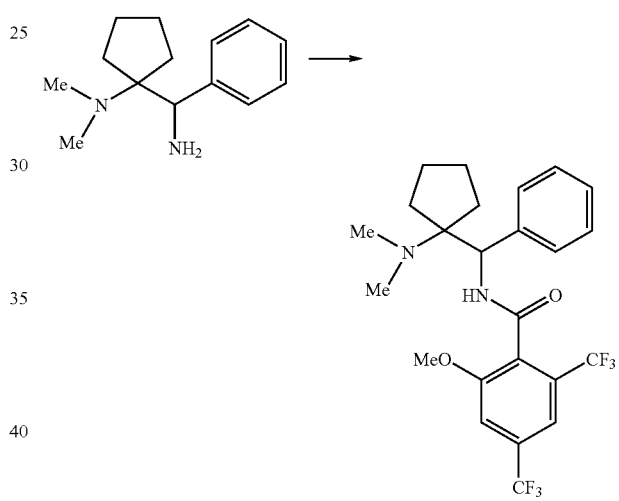

To a stirred solution of {1-[amino(phenyl)methyl]cyclopentyl}dimethylamine D3 enantiomer 2 (0.8 g; 3.67 mmol) and triethylamine (1.02 ml; 7.34 mmol) in DCM (35 ml) was added 2,4-ditrifluoromethyl-6-methoxy-benzoyl chloride (1.12 g; 3.67 mmol) in DCM (5 ml) dropwise over 5 min. The resulting solution was allowed to stand for 66 h at room temperature and then saturated aqueous sodium bicarbonate solution (40 ml) added. After stirring at room temperature for 0.5 h. the reaction mixture was loaded onto a phase separation cartridge and the eluted organic phase evaporated under reduced pressure. The residue was dissolved in a minimum of DCM and chromatographed on silica gel eluting with 0 to 95% ethyl acetate-pentane mixtures. After evaporating the collected fractions under reduced pressure, redissolving in DCM and evaporating under reduced pressure the title compound was obtained as a colourless solid (1.33 g; 74%). $^1$H NMR (CDCl$_3$) δ: 0.90-1.05 (1H, m), 1.25-1.60 (3H, m), 1.60-1.75 (2H, m), 1.80-1.90 (2H, m), 2.20 (6H, s), 3.93 (3H, s), 5.07 (1H, d, J=5 Hz), 7.14 (1H, br s), 7.20-7.35 (4H, m), 7.44 (2H, m), 7.53 (1H, s). Mass Spectrum (Electrospray LC/MS): Found 489 (MH$^+$). $C_{24}H_{26}F_6N_2O_2$ requires 488. Ret. time 2.17 min.

EXAMPLE 19

4-Chloro-N-[[1-(dimethylamino)cyclopentyl](phenyl)methyl]-2-methyl-6-(methylthio)benzamide chiral

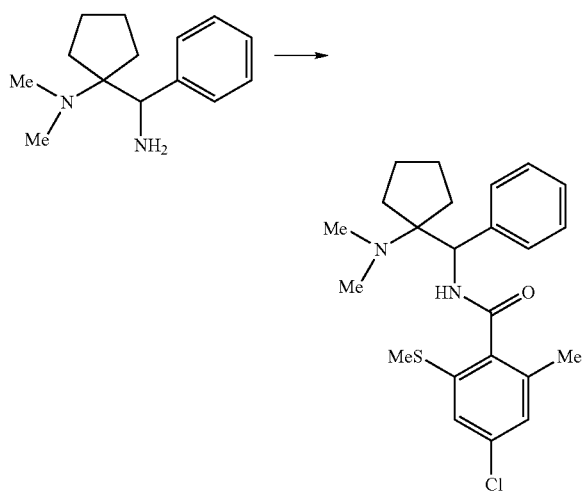

A mixture of {1-[amino(phenyl)methyl]cyclopentyl}dimethylamine D3 enantiomer 2 (203 mg; 0.93 mmol), 4-chloro-2-methyl-6-(methylthio)benzoic acid (obtainable as described in F. P. Doyle, J. H. C. Nayler, H. R. J. Waddington, J. C. Hanson and G. R. Thomas. J. Chem. Soc. 1963, 497) (202 mg; 0.93 mmol), EDC (178 mg; 0.93 mmol) and HOBt (143 mg; 0.93 mmol) in DCM (20 ml) was stirred at room temperature for 4 h and then stood at room temperature for 90 h. The resulting reaction mixture was washed with saturated aqueous sodium bicarbonate (50 ml) and the organic layer separated by passage through a phase separation cartridge. The organic layer was evaporated, the residue dissolved in a minimum of DCM and chromatographed on silica gel, eluting with 0-100% ethyl acetate-pentane. The fractions were combined and evaporated under reduced pressure to afford the title compound (200 mg; 52%). $^1$H NMR (CDCl$_3$) δ: 0.90-1.10 (1H, m), 1.38-1.55 (3H, m), 1.60-1.76 (2H, m), 1.80-1.90 (2H, m), 2.21 (6H, s), 2.26 (3H, s), 2.47 (3H, s), 5.11 (1H, d, J=6 Hz), 6.94 (1H, d, J=5.2 Hz), 7.00 (1H, m), 7.09 (1H, m), 7.20-7.35 (3H, m), 7.40-7.50 (2H, m). Mass spectrum (Electrospray LC/MS), ES$^+$: Found 417 (MH$^+$). C$_{23}$H$_{29}$$^{35}$ClN$_2$OS requires 416. Ret. time 2.03 min. The title product was converted to its corresponding hydrochloride salt (210 mg).

EXAMPLE 20

(±)2-Chloro-N-[2-methyl-2-(2-methyl-1-pyrrolidinyl)-1-phenylpropyl]-3-(trifluoromethyl)benzamide Diastereomers

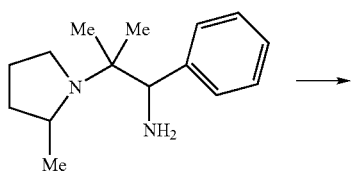

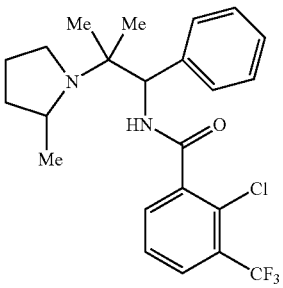

A mixture of [2-methyl-2-(2-methyl-1-pyrrolidinyl)-1-phenylpropyl]amine D26 (0.150 g; 0.647 mmol), 2-chloro-3-(trifluoromethyl)benzoic acid (0.174 g; 0.775 mmol), EDC (0.149 g; 0.777 mmol) and HOBt (0.020 g; 0.148 mmol) in DCM (4 ml) was shaken at room temperature for 66 hours. Saturated sodium hydrogen carbonate (8 ml) was added and shaking continued for 0.5 hours. The organic layer was passed through a phase separation cartridge and applied to a 2 g SCX column. The column was washed with DCM and methanol and the product eluted with 1M ammonia in methanol. The crude product was purified by chromatography on silica gel (20 g) eluting with 0-100% ethyl acetate in pentane gradient to afford the title compound as two pairs of enantiomers.

For the less polar pair of enantiomers (0.170 g; 60%). $^1$H NMR (CDCl$_3$) δ: 0.97 (6H, s), 1.05 (3H, d, J=6 Hz), 1.50 (1H, br m), 1.70-1.85 (3H, br m), 2.76-2.83 (1H, m), 2.90-2.97 (1H, m), 3.15-3.20 (1H, m), 4.73 (1H, d, J=2 Hz), 7.20-7.42 (5H, m), 7.43 (1H, t, J=8 Hz), 7.75-7.79 (2H, m), 7.84 (1H, br s). Mass spectrum (Electrospray LC/MS), ES$^+$: Found 439 (MH$^+$). C$_{23}$H$_{26}$$^{35}$ClF$_3$N$_2$O requires 438. Ret. time 2.17 min. The title product was converted to its corresponding hydrochloride salt.

For the more polar pair of enantiomers (0.100 g; 35%). $^1$H NMR (CDCl$_3$) δ: 0.95-1.10 (9H, m), 1.45 (1H, br m), 1.65-1.82 (3H, br m), 2.60-2.67 (1H, m), 2.85-2.93 (1H, m), 3.35-3.40 (1H, m), 4.76 (1H, d, J=3.2 Hz), 7.20-7.45 (5H, m), 7.60 (1H, br m), 7.70-7.80 (2H, m), 7.84 (1H, m). Mass spectrum (Electrospray LC/MS), ES$^+$: Found 439 (MH$^+$). C$_{23}$H$_{26}$$^{35}$ClF$_3$N$_2$O requires 438. Ret. time 2.17 min. The title product was converted to its corresponding hydrochloride salt.

EXAMPLE 21

(±)-3-Bromo-2-methyl-N-[2-methyl-1-phenyl-2-(1-pyrrolidinyl)propyl]benzamide

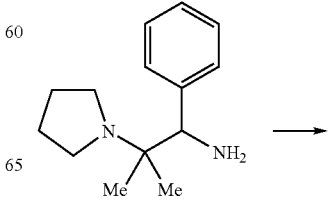

-continued

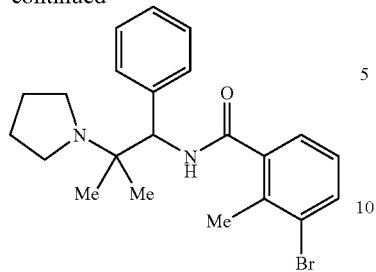

To PS-EDC (0.068 g; 0.1 mmol; 1.42 mmol/g) was added a solution of HOAt (0.01 mmol in 0.8 ml (THF:DCM, 1:1)) followed by the addition of 3-bromo-2-methyl-benzoic acid (0.011 g; 0.05 mmol) in 1:3 NMP:THF (0.25 ml) and then [2-methyl-1-phenyl-2-(1-pyrrolidinyl)propyl]amine D5 (0.011 g 0.05 mmol) in DCM (0.25 ml). The reaction was allowed to mix for 60 h. Following this PS-isocyanate (0.068 g, 0.1 mmol, 1.5 mmol/g) and PS—CO3 (0.068 g, 0.1 mmol, 1.5 mmol/g) were added and allowed to mix for another 24 h. The reaction mixture was filtered and passed through an SCX block (500 mg) (pre-wetted with DCM). The content of the Robbins block was washed with more solvent (DCM:THF, 1:1) and allowed to pass through the SCX which was then washed with DCM (2 ml×2) and methanol (2 ml×2). The SCX was then eluted with 0.5M ammonia in methanol and the product containing eluent evaporated to afford the title product (17.4 mg; 84%). Mass Spectrum (Electrospray LC/MS): Found 414 (MH$^+$). $C_{22}H_{27}{}^{79}BrN_2O$ requires 415; Ret. time 2.64 min*

EXAMPLE 22

(±)-2-Chloro-N-[[1-(methylamino)cyclopentyl](phenyl)methyl]-3-(trifluoromethyl)benzamide

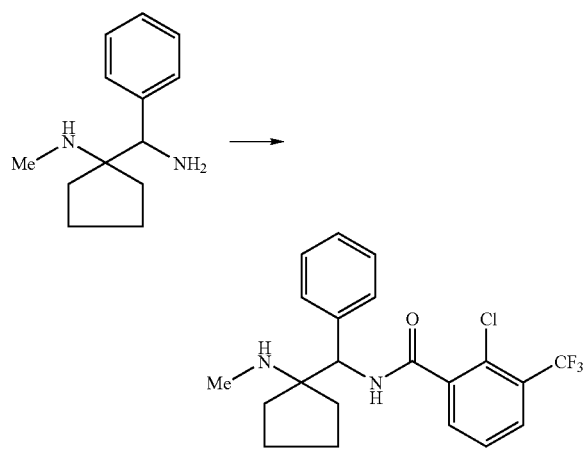

To a solution of 2-chloro-3-(trifluoromethyl)benzoic acid (0.728 g; 3.24 mmol) in DMF (20 ml) and DIPEA (2.5 ml) was added (±)-{[amino(phenyl)methyl]cyclopentyl}methylamine D29 (1.0 g; 3.60 mmol) and HATU (1.23 g; 3.24 mmol). The resulting mixture was allowed to stir at room temperature overnight and then DMF evaporated off in vacuo. Residual material was partitioned between ethyl acetate and water. The organic layer was dried (Na$_2$SO$_4$) and the filtrate evaporated in vacuo. The desired product was isolated by column chromatography on silica gel using 20% diethyl ether to 100% diethyl ether in n-pentane to afford the title compound as a white solid (0.908 g; 61%). $^1$H NMR (CDCl3) δ: 1.47-1.83 (9H, m), 2.21 (3H, s), 5.1 (1H, m), 7.23-7.43 (6H, m), 7.58 (1H, m), 7.65 (1H, m), 7.73 (1H, m); Mass Spectrum (Electrospray LC/MS), API$^+$: Found 411 (MH$^+$). $C_{21}H_{22}{}^{35}ClF_3N_2O$ requires 410. Ret. time 2.04 min.

EXAMPLE 23

(±)-2-Chloro-N-[{1-[(2-hydroxyethyl)(methyl)amino]cyclopentyl}(phenyl)methyl]-3-(trifluoromethyl)benzamide

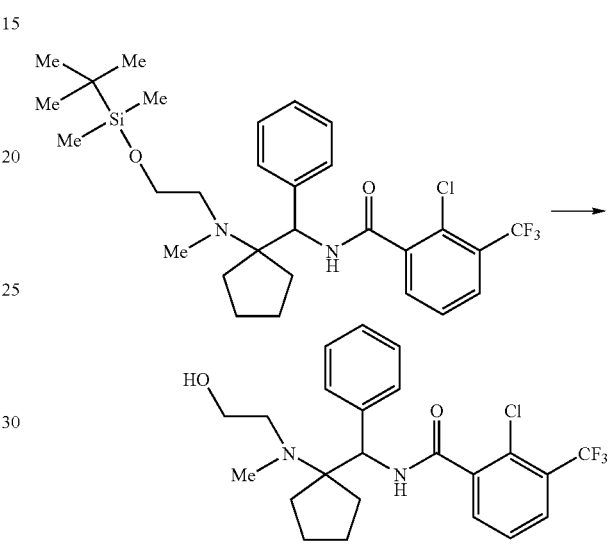

To a solution of (±)-2-chloro-N-[{1-[(2-{[(1,1-dimethylethyl)(dimethyl)silyl]oxy}ethyl)(methyl)amino]cyclopentyl}(phenyl)methyl]-3-(trifluoromethyl)benzamide D30 (0.390 g; 0.685 mmol) in THF (10 ml) was added tetrabutylammonium fluoride (1M solution in THF 1.6 ml; 1.6 mmol). The reaction mixture was allowed to stir at room temperature for 4 h. The desired product was isolated by column chromatography on silica using 20% to 50% ether in n-pentane, the solvent was reduced in volume by evaporation in vacuo and loaded onto an SCX cartridge. Washing with DCM, then methanol followed by elution with 1M ammonia in methanol afforded the title product (170 mg, 73%). Mass Spectrum (Electrospray LC/MS). Found 455 (MH$^+$). $C_{23}H_{26}{}^{35}ClF_3N_2O_2$ requires 454. Ret. time: 2.09 min.

EXAMPLE 24

2,6-Dimethyl-N-[[1-(methylamino)cyclopentyl](phenyl)methyl]benzamide chiral

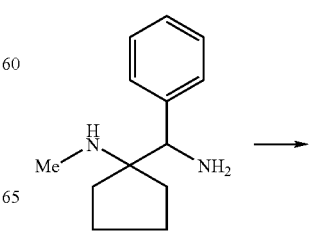

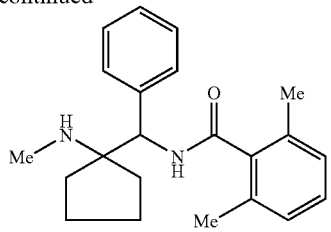

To a solution of 2,6-dimethylbenzoic acid (0.100 g; 0.668 mmol) in DMF (5 ml) and DIPEA (0.12 ml) was added {[amino(phenyl)methyl]cyclopentyl}methylamine D31 enantiomer 2 (0.124 g; 0.608 mmol) and HATU (0.254 g; 0.668 mmol). The resulting mixture was allowed to stir at room temperature for 3 days and then the DMF was evaporated off under reduced pressure. Residual material was partitioned between ethyl acetate and water, washed with water and the organic layer was dried ($Na_2SO_4$) and evaporated. The residual material was dissolved in DCM (2 ml) and loaded onto an SCX cartridge. Washing with DCM, then methanol followed by elution with 1 M ammonia in methanol afforded the title product (155 mg; 76%). $^1$H NMR (CDCl3) δ: 1.3-1.8 (9H, m), 2.21 (3H, s), 2.28 (6H, s), 5.07 (1H, m), 7.0 (2H, m), 7.1-7.4 (7H, m). Mass Spectrum (Electrospray LC/MS). Found 337 (MH$^+$). $C_{22}H_{28}N_2O$ requires 336. Ret. time: 1.86 min.

EXAMPLE 25

(±)-N-[(1-aminocyclopentyl)(phenyl)methyl]-2,6-dimethylbenzamide

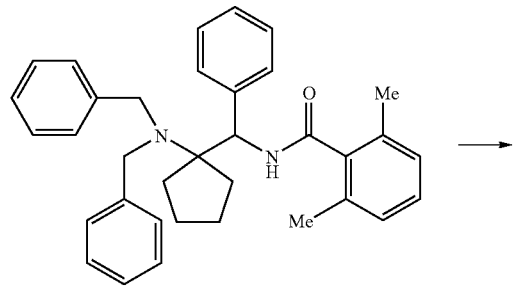

The title compound (1.14 g; 71%) was prepared from the catalytic hydrogenation of (±)-N-[{1-[bis(phenylmethyl)amino]cyclopentyl}(phenyl)methyl]-2,6-dimethylbenzamide D34 (2.51 g; 5 mmol) over 10% Pd/Carbon (0.4 g) in 3 MHCl (8 ml) and ethanol (150 ml) in a similar manner to that described in D29. The ethanol was evaporated off in vacuo and the residual material was partitioned between DCM and sodium bicarbonate solution and dried ($Na_2SO_4$). The filtrate was reduced in volume by evaporation in vacuo and loaded onto an SCX cartridge. Washing with DCM, then methanol followed by elution with 1M ammonia in methanol afforded the title product (90 mg, 88%). $^1$H NMR (CDCl3) δ: 0.98-1.96 (10H, m). 2.23 (6H, s), 4.97 (1H, m), 7.0 (2H, m), 7.16 (1H, m), 7.22-7.41 (6H, m); Mass Spectrum (Electrospray LC/MS). Found 323 (MH$^+$). $C_{21}H_{26}N_2O$ requires 322. Ret. time 1.69 min.

EXAMPLE 26

(±)N-[2-(Dimethylamino)-3-hydroxy-2-methyl-1-phenylpropyl]-2,3-dimethylbenzamide diastereomeric mixture

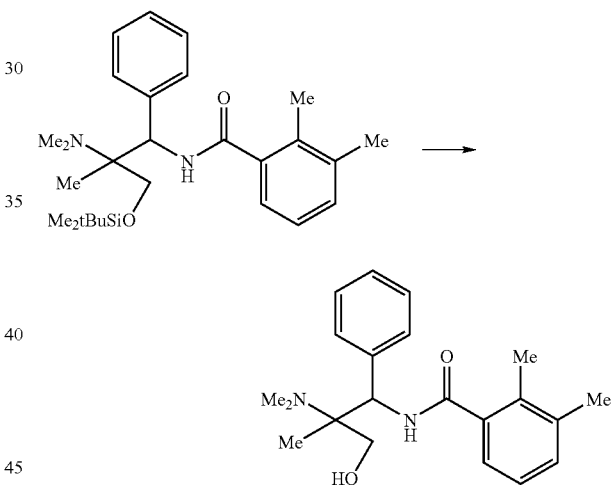

A solution of (±)-N-(2-(dimethylamino)-3-{[(1,1-dimethylethyl)(dimethyl)silyl]oxy}-2-methyl-1-phenylpropyl)-2,3-dimethylbenzamide D49 (56 mg; 0.12 mmol) in THF (5 ml) was treated with a solution of tetrabutylammonium fluoride (1.0M solution in THF; 0.2 ml, 0.2 mmol) and the mixture stirred at room temperature overnight. The mixture was poured directly onto a chromatography column (Flashmaster II; eluent 0-100% ethyl acetate/pentane) to afford the title compound (38 mg; 63%). $^1$H NMR (CDCl$_3$) δ: 0.73 and 1.14 (3H, 2×s), 1.70-2.50 (1H, br s), 2.26 (6H, q), 2.38 and 2.48 (6H, 2×s), 3.17, 3.39, and 3.55 (2H, 3×d), 5.26 and 5.46 (1H, 2×d), 6.83 and 7.89 (1H, 2×br d), 7.07-7.46 (8H, br m). Mass spectrum (Electrospray LC/MS), API$^+$: Found 341 (MH$^+$), $C_{21}H_{28}N_2O_2Si$ requires 340. Ret. time 1.71 and 1.76 min.

The examples in Table 3 were prepared in a manner similar to that described in example E26.

TABLE 3

| Example | Structure | Mass spectrum (Electrospray LC/MS), API+ Ret. time (min) | Name |
| --- | --- | --- | --- |
| 27 | 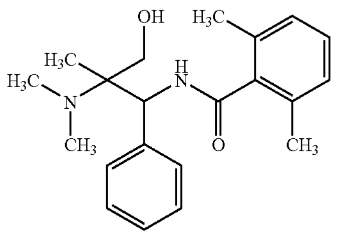 | Found 341 (MH+) $C_{21}H_{28}N_2O_2$ requires 340; 1.78 and 1.83. | (±)-N-[2-(dimethylamino)-3-hydroxy-2-methyl-1-phenylpropyl]-2,6-dimethylbenzamide |
| 28 | 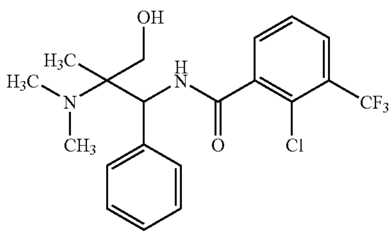 | Found 415 (MH+) $C_{20}H_{22}{}^{35}ClF_3N_2O_2$ requires 414; 1.91 and 1.94. | (±)-2-chloro-N-[2-(dimethylamino)-3-hydroxy-2-methyl-1-phenylpropyl]-3-(trifluoromethyl)benzamide |

EXAMPLE 29

(±)N-[[3-(Dimethylamino)tetrahydro-3-furanyl](phenyl)methyl]-2,6-dimethylbenzamide: Diastereomer 1 and Diastereomer 2

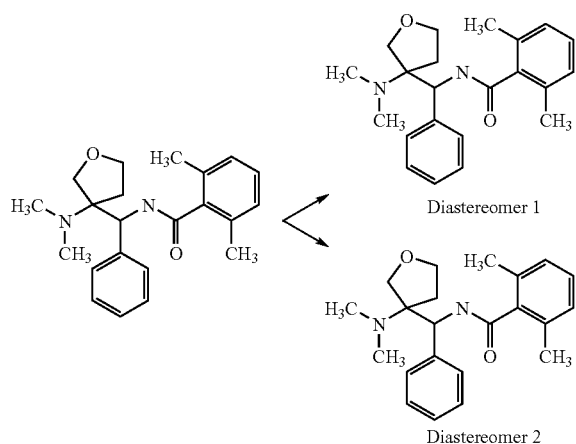

Racemic N-[[3-(dimethylamino)tetrahydro-3-furanyl](phenyl)methyl]-2,6-dimethyl benzamide E204 (40 mg, 0.11 mmol) was separated by preparative chiral HPLC to afford the title product diastereomer 1 (13 mg); Chiral HPLC:>95% de; Mass spectrum (Electrospray LC/MS): Found 353 (MH+). Ret. time 1.67 min. $C_{22}H_{28}N_2O_2$ requires 352 and diastereomer 2 (14 mg); Chiral HPLC:>95% de; Mass spectrum (Electrospray LC/MS): Found 353 (MH+) Ret. time 1.69 min. $C_{22}H_{28}N_2O_2$ requires 352.

Preparative HPLC Conditions:

| Column: | S.F.C. Ethyl Pyridyl 150 mm × 21.1 mm i.d; 6 micron particle size |
| --- | --- |
| Mobile phase: | Carbon Dioxide:Ethanol (95:5) v/v; pump-mixed isocratic |
| Flow rate: | 50 ml/min |
| Pressure: | 100 bar |
| Temperature: | 40° C. |
| UV wavelength range: | 220 nm |
| Elution time: | 10 min |
| Ret. Time: | 6.3 min (Diastereomer 1); 7.1 min (Diastereomer 2) |

Analytical Chromatography Conditions:

| Column: | S.F.C. Ethyl Pyridyl 150 mm × 4.6 mm i.d; 6 micron particle size |
| --- | --- |
| Mobile phase: | Carbon Dioxide:Ethanol (98:2) v/v; pump-mixed isocratic |
| Flow rate: | 2.35 ml/min |
| Pressure: | 100 bar |
| Temperature: | 38° C. |
| UV wavelength range: | 254 nm |
| Elution time: | 15 min |
| Ret. Time: | 12.2 min (Diastereomer 1); 13.4 min (Diastereomer 2) |

EXAMPLE 30

(±)-2-Chloro-N-[{1-[(cyclopropylmethyl)(methyl)amino]cyclopentyl}(phenyl)methyl]-3-(trifluoromethyl)benzamide hydrochloride

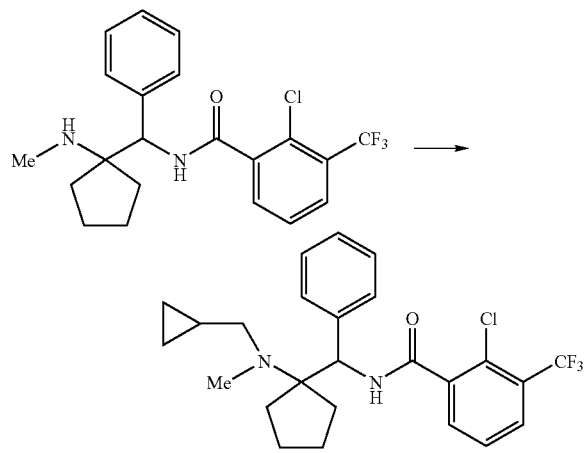

To a solution (±)-2-chloro-N-[[1-(methylamino)cyclopentyl](phenyl)methyl]-3-(trifluoromethyl)benzamide E22 (143 g; 0.35 mmol), cyclopropanecarboxaldehyde (0.026 ml; 0.035 mmol) and acetic acid (3 drops) in 1,2-dichloroethane (10 ml) was added sodium triacetoxyborohydride (303 mg; 1.4 mmol). The resulting mixture was allowed to stir at room temperature under argon overnight. Then the reaction mixture was diluted with DCM (20 ml), washed with saturated potassium carbonate solution and brine, dried ($Na_2SO_4$) and evaporated in vacuo. The mixture was separated by column chromatography on silica gel using 20% ether in n-pentane to 2% methanol in ether. The oil obtained was treated with 1M HCl in ether to give the title product as an off white hydrochloride salt (0.054 g; 33%). Mass Spectrum (Electrospray LC/MS). Found 465 ($MH^+$). $C_{25}H_{28}{}^{35}ClF_3N_2O$ requires 464. Ret. time: 2.30 min.

The compounds in Table 4 below were prepared using similar methods to those described for Example 30 above.

TABLE 4

| Example | Structure | Mass spectrum (Electrospray LC/MS), API+ Ret. time (min) | Name |
|---|---|---|---|
| 31 | 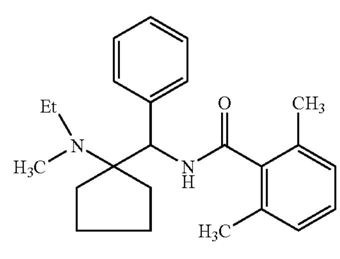 | Found 365 ($MH^+$). $C_{24}H_{32}N_2O$ requires 364; 1.96. | (±)-N-[{1-[ethyl(methyl)amino]cyclopentyl}(phenyl)methyl]-2,6-dimethylbenzamide |
| 32 | 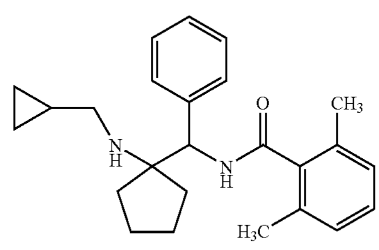 | Found 377 ($MH^+$). $C_{25}H_{32}N_2O$ requires 376; 2.07 | (±)-N-[{1-[(cyclopropylmethyl)amino]cyclopentyl)(phenyl)methyl]-2,6-dimethylbenzamide |
| 33 | 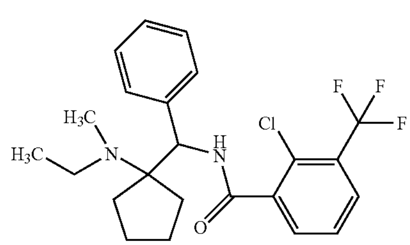 | Found 439 ($MH^+$). $C_{23}H_{26}{}^{35}ClF_3N_2O$ requires 438; 2.23. | (±)-2-Chloro-N-[{1-[ethyl(methyl)amino]cyclopentyl}(phenyl)methyl]-3-(trifluoromethyl)benzamide |

TABLE 4-continued

| Example | Structure | Mass spectrum (Electrospray LC/MS), API+ Ret. time (min) | Name |
|---|---|---|---|
| 34 | 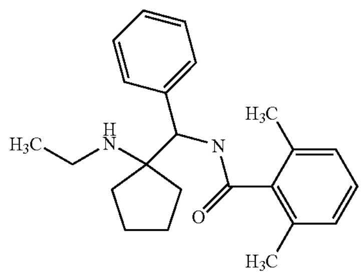 | Found 351 (MH+). C23H30N2O requires 350; 1.82. | N-[[1-(ethylamino)cyclopentyl]-(phenyl)methyl]-2,6-dimethylbenzamide |
| 35 | 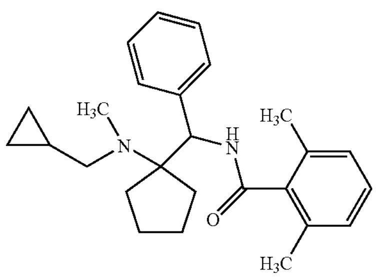 | Found 391 (MH+). C26H34N2O requires 390; 2.19 | (±)-N-[{1-[(cyclopropylmethyl)(methyl)amino]cyclopentyl}(phenyl)methyl]-2,6-dimethylbenzamide |

The compounds in Table 5 below were prepared using similar methods to those described for the Examples above. Coupling method: A=Acid chloride (using method similar to that in Example 13); E=EDC (using method similar to that in Example 17); H=HATU (using method similar to that in Example 15); P=Polymer-supported DCC (using method similar to that in Example 1); PE=Polymer-supported EDC (using method similar to that in Example 21). Work-up and purification was carried out using appropriate methods similar to those described in the examples above.

Benzoic acid starting materials were obtained commercially except for 2,6-dichloro-3-trifluoromethylbenzoic acid used for the examples indicated with a #, which was obtained by the method described in DE1924766. 4-chloro-2-methyl-6-(methylthio)benzoic acid is obtainable as described in F. P. Doyle, J. H. C. Nayler, H. R. J. Waddington, J. C. Hanson and G. R. Thomas. J. Chem. Soc. 1963, 497.

For the example compound names, those denoted by (±)- are derived from the corresponding racemic amine D2, D8, D10, D12, D14, D16, D18, D20, D22, D24, D26, D29, D36, D38, D40, D42, D43, D46, D48 and those without are from the corresponding chiral amines D3 enantiomer 2, D6, D31 enantiomer 2. LCMS retention times were generally measured using analytical LC/MS chromatography conditions method A Compounds annoted with * are compounds prepared using array format described in Example 23 and they were analysed using analytical LC/MS chromatography conditions method B.

TABLE 5

| Ex | Structure | Method | Mass spectrum (Electrospray LC/MS), API+ Ret. time (min) | Name |
|---|---|---|---|---|
| 36 | 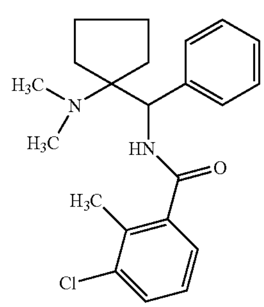 | P | Found 371 (MH+) C22H27 35ClN2O requires 370; 2.08 | 3-chloro-N-[[1-(dimethylamino)cyclopentyl](phenyl)methyl]-2-methylbenzamide chiral |

TABLE 5-continued

| Ex | Structure | Method | Mass spectrum (Electrospray LC/MS), API+ Ret. time (min) | Name |
|---|---|---|---|---|
| 37 | 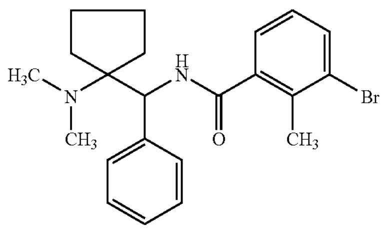 | P | Found 415 (MH+) C22H27^79BrN2O requires 414; 2.09 | 3-bromo-N-[[1-(dimethylamino)cyclopentyl](phenyl)methyl]-2-methylbenzamide chiral |
| 38 | 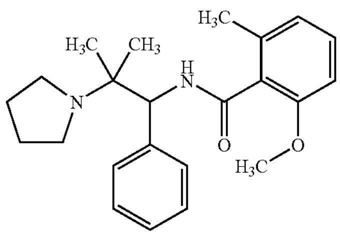 | P | Found 367 (MH+) C23H30N2O2 requires 366; 1.84 | 2-methyl-6-(methyloxy)-N-[2-methyl-1-phenyl-2-(1-pyrrolidinyl)propyl]benzamide chiral |
| 39 | 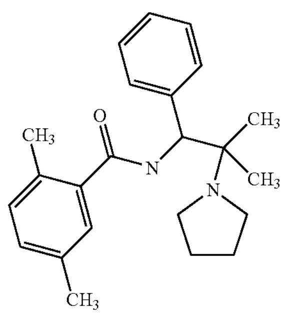 | P | Found 351 (MH+) C23H30N2O requires 350; 2.03 | (±)-2,5-dimethyl-N-[2-methyl-1-phenyl-2-(1-pyrrolidinyl)propyl]benzamide |
| 40 | 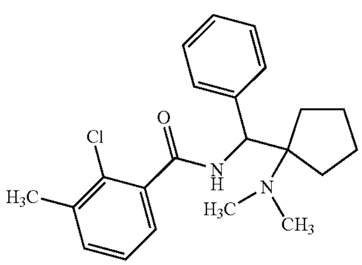 | P | Found 371 (MH+) C22H27^35ClN2O requires 370; 2.01 | 2-chloro-N-[(1-(dimethylamino)cyclopentyl](phenyl)methyl]-3-methylbenzamide chiral |
| 41 | 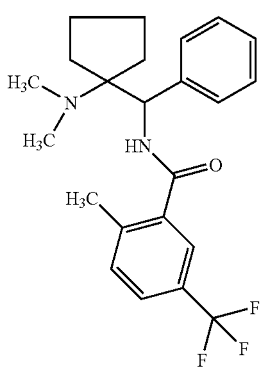 | P | Found 405 (MH+) C23H27F3N2O requires 404; 2.20 | N-[[1-(dimethylamino)cyclopentyl](phenyl)methyl]-2-methyl-5-(trifluoromethyl)benzamide chiral |

TABLE 5-continued

| Ex | Structure | Method | Mass spectrum (Electrospray LC/MS), API+ Ret. time (min) | Name |
|---|---|---|---|---|
| 42 | 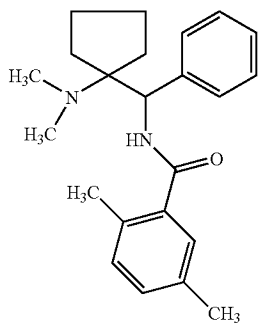 | P | Found 351 (MH+) C$_{23}$H$_{30}$N$_2$O requires 350; 2.04 | N-[[1-(dimethylamino)cyclopentyl](phenyl)methyl]-2,5-dimethylbenzamide chiral |
| 43 | 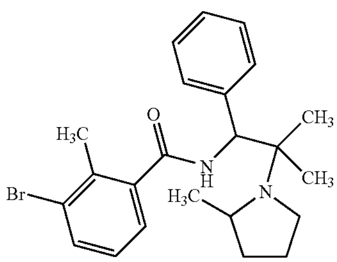 | PE | Found 429 (MH+) C$_{23}$H$_{29}$$^{79}$BrN$_2$O requires 428; 2.68* | (±)-3-bromo-2-methyl-N-[2-methyl-2-(2-methyl-1-pyrrolidinyl)-1-phenylpropyl]benzamide |
| 44 | 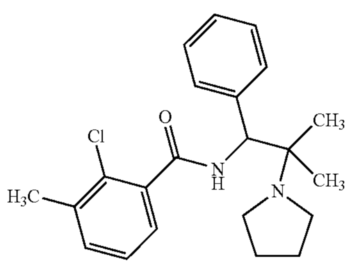 | P | Found 371 (MH+) C$_{22}$H$_{27}$$^{35}$ClN$_2$O requires 370; 1.98 | (±)-2-chloro-3-methyl-N-[2-methyl-1-phenyl-2-(1-pyrrolidinyl)propyl]benzamide |
| 45 | 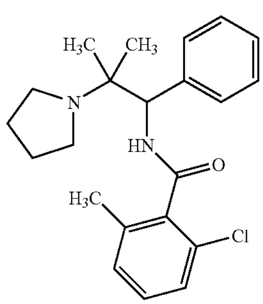 | P | Found 371 (MH+) C$_{22}$H$_{27}$$^{35}$ClN$_2$O requires 370; 1.90 | (±)-2-chloro-6-methyl-N-[2-methyl-1-phenyl-2-(1-pyrrolidinyl)propyl]benzamide |
| 46 | 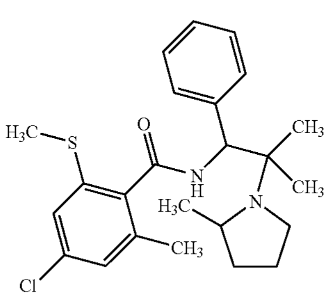 | PE | Found 431 (MH+) C$_{24}$H$_{31}$$^{35}$ClN$_2$OS requires 430; 2.57* | (±)-4-chloro-2-methyl-N-[2-methyl-2-(2-methyl-1-pyrrolidinyl)-1-phenylpropyl]-6-(methylthio)benzamide |

TABLE 5-continued

| Ex | Structure | Method | Mass spectrum (Electrospray LC/MS), API+ Ret. time (min) | Name |
|---|---|---|---|---|
| 47 | 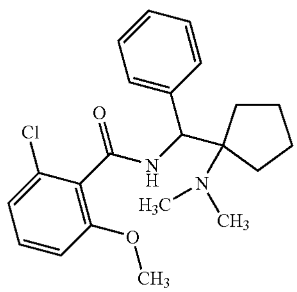 | P | Found 387 (MH+) C$_{22}$H$_{27}$$^{35}$ClN$_2$O$_2$ requires 386; 1.88 | 2-chloro-N-[[1-(dimethylamino)cyclopentyl](phenyl)methyl]-6-(methyloxy)benzamide chiral |
| 48 | 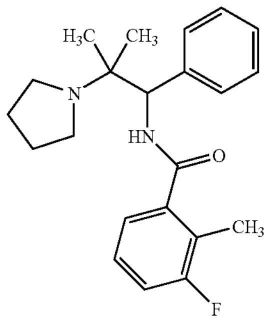 | P | Found 355 (MH+) C$_{22}$H$_{27}$FN$_2$O requires 354; 1.96 | (±)-3-fluoro-2-methyl-N-[2-methyl-1-phenyl-2-(1-pyrrolidinyl)propyl]benzamide |
| 49 | 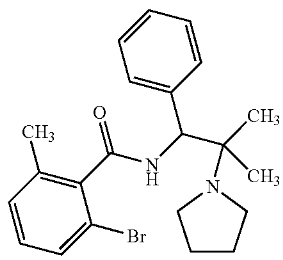 | P | Found 415 (MH+) C$_{22}$H$_{27}$$^{79}$BrN$_2$O requires 414; 1.92 | (±)-2-bromo-6-methyl-N-[2-methyl-1-phenyl-2-(1-pyrrolidinyl)propyl]benzamide |
| 50 | 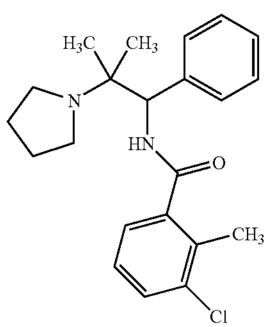 | P | Found 371 (MH+) C$_{22}$H$_{27}$$^{35}$ClN$_2$O requires 370; 2.08 | (±)-3-chloro-2-methyl-N-[2-methyl-1-phenyl-2-(1-pyrrolidinyl)propyl]benzamide |
| 51 | 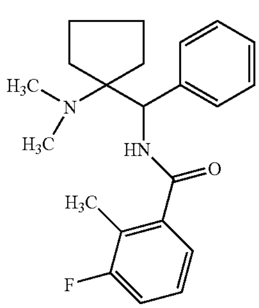 | P | Found 355 (MH+) C$_{22}$H$_{27}$FN$_2$O requires 354; 1.97 | N-[[1-(dimethylamino)cyclopentyl](phenyl)methyl]-3-fluoro-2-methylbenzamide chiral |

TABLE 5-continued

| Ex | Structure | Method | Mass spectrum (Electrospray LC/MS), API+ Ret. time (min) | Name |
| --- | --- | --- | --- | --- |
| 52 | 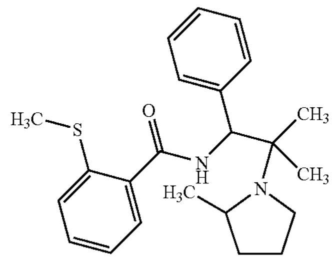 | PE | Found 383 (MH+) $C_{23}H_{30}N_2OS$ requires 382; 2.62* | (±)-N-[2-methyl-2-(2-methyl-1-pyrrolidinyl)-1-phenylpropyl]-2-(methylthio)benzamide |
| 53 | 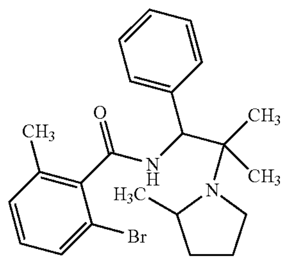 | PE | Found 429 (MH+) $C_{23}H_{29}^{79}BrN_2O$ requires 428; 2.44* | (±)-2-bromo-6-methyl-N-[2-methyl-2-(2-methyl-1-pyrrolidinyl)-1-phenylpropyl]benzamide |
| 54 | 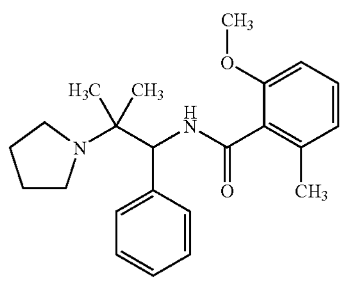 | P | Found 367 (MH+) $C_{23}H_{30}N_2O_2$ requires 366; 1.84 | (±)-2-methyl-6-(methyloxy)-N-[2-methyl-1-phenyl-2-(1-pyrrolidinyl)propyl]benzamide |
| 55 | 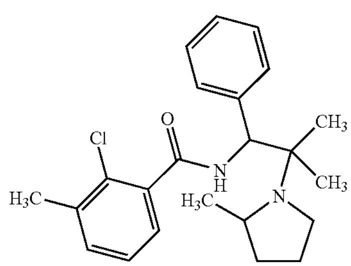 | PE | Found 385 (MH+) $C_{23}H_{29}^{35}ClN_2O$ requires 384; 2.65* | (±)-2-chloro-3-methyl-N-[2-methyl-2-(2-methyl-1-pyrrolidinyl)-1-phenylpropyl]benzamide |
| 56 | 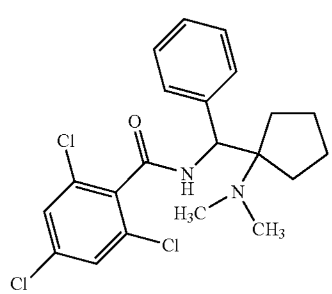 | P | Found 425 (MH+) $C_{21}H_{23}^{35}Cl_3N_2O$ requires 424; 2.08 | 2,4,6-trichloro-N-[[1-(dimethylamino)cyclopentyl](phenyl)methyl]benzamide chiral |

TABLE 5-continued

| Ex | Structure | Method | Mass spectrum (Electrospray LC/MS), API+ Ret. time (min) | Name |
|---|---|---|---|---|
| 57 | 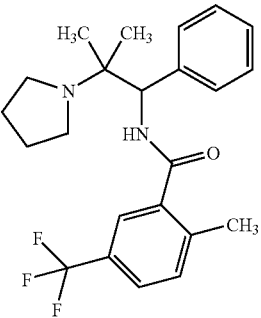 | P | Found 405 (MH+) C23H27F3N2O requires 404; 2.18 | (±)-2-methyl-N-[2-methyl-1-phenyl-2-(1-pyrrolidinyl)propyl]-5-(trifluoromethyl)benzamide |
| 58 | 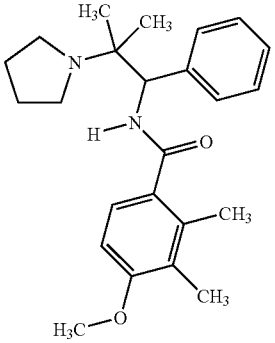 | P | Found 381 (MH+) C24H32N2O2 requires 380; 2.10 | 2,3-Dimethyl-4-(methyloxy)-N-[2-methyl-1-phenyl-2-(1-pyrrolidinyl)propyl]benzamide chiral |
| 59 | 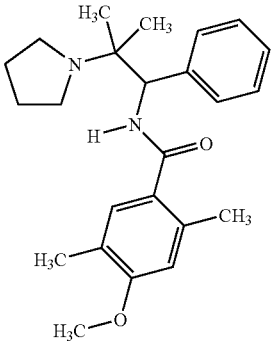 | P | Found 381 (MH+) C24H32N2O2 requires 380; 2.14 | 2,5-Dimethyl-4-(methyloxy)-N-[2-methyl-1-phenyl-2-(1-pyrrolidinyl)propyl]benzamide chiral |
| 60 | 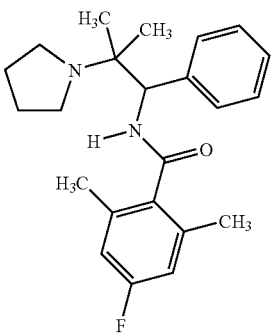 | A | Found 369 (MH+) C23H29FN2O requires 368; 2.00 | 4-Fluoro-2,6-dimethyl-N-[2-methyl-1-phenyl-2-(1-pyrrolidinyl)propyl]benzamide chiral |

TABLE 5-continued

| Ex | Structure | Method | Mass spectrum (Electrospray LC/MS), API+ Ret. time (min) | Name |
|---|---|---|---|---|
| 61 | 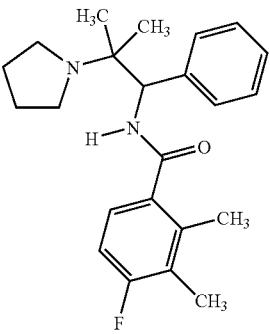 | P | Found 369 (MH+) $C_{23}H_{29}FN_2O$ requires 368; 2.02 | 4-Fluoro-2,3-dimethyl-N-[2-methyl-1-phenyl-2-(1-pyrrolidinyl)propyl]benzamide chiral |
| 62 | 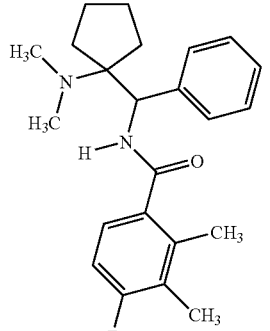 | P | Found 369 (MH+) $C_{23}H_{29}FN_2O$ requires 368; 2.05 | N-[[1-(Dimethylamino)cyclopentyl](phenyl)methyl]-4-fluoro-2,3-dimethylbenzamide chiral |
| 63 | 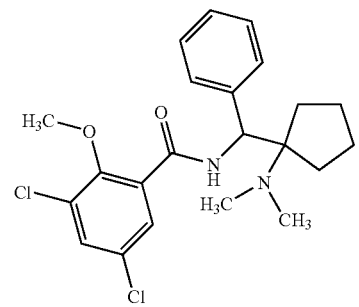 | PE | Found 421 (MH+) $C_{22}H_{26}{}^{35}Cl_2N_2O_2$ requires 420; 2.55* | 3,5-dichloro-N-[[1-(dimethylamino)cyclopentyl](phenyl)methyl]-2-(methyloxy)benzamide chiral |
| 64 | 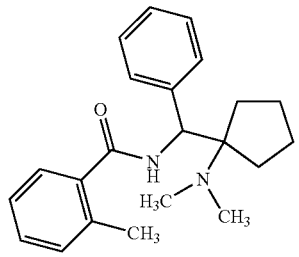 | PE | Found 337 (MH+) $C_{22}H_{28}N_2O$ requires 336; 2.34* | N-[[1-(dimethylamino)cyclopentyl](phenyl)methyl]-2-methylbenzamide chiral |

TABLE 5-continued

| Ex | Structure | Method | Mass spectrum (Electrospray LC/MS), API+ Ret. time (min) | Name |
|---|---|---|---|---|
| 65 | 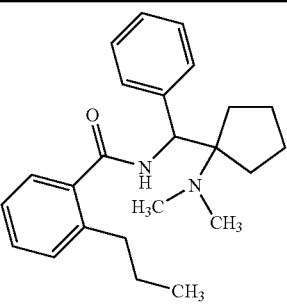 | PE | Found 365 (MH+) $C_{24}H_{32}N_2O$ requires 364; 2.48* | N-[[1-(dimethylamino)cyclopentyl](phenyl)methyl]-2-propylbenzamide chiral |
| 66 | 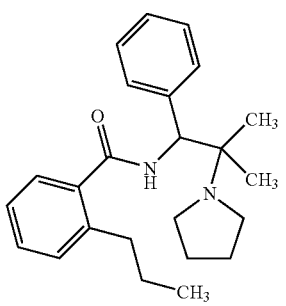 | PE | Found 365 (MH+) $C_{24}H_{32}N_2O$ requires 364; 2.45* | (±)-N-[2-methyl-1-phenyl-2-(1-pyrrolidinyl)propyl]-2-propylbenzamide |
| 67 | 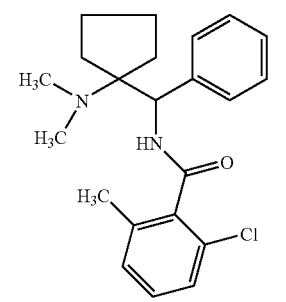 | P | Found 371 (MH+) $C_{22}H_{27}{}^{35}ClN_2O$ requires 370; 1.93 | 2-chloro-N-[[1-(dimethylamino)cyclopentyl](phenyl)methyl]-6-methylbenzamide chiral |
| 68 | 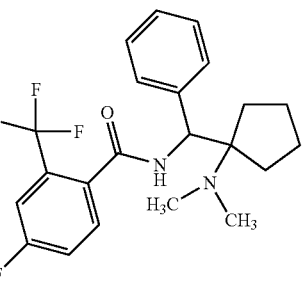 | PE | Found 409 (MH+) $C_{22}H_{24}F_4N_2O$ requires 408; 2.44* | N-[[1-(dimethylamino)cyclopentyl](phenyl)methyl]-4-fluoro-2-(trifluoromethyl)benzamide chiral |
| 69 | 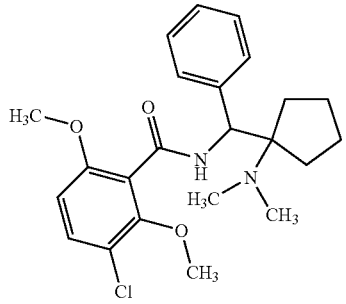 | PE | Found 417 (MH+) $C_{23}H_{29}{}^{35}ClN_2O_3$ requires 416; 2.43* | 3-chloro-N-[[1-(dimethylamino)cyclopentyl](phenyl)methyl]-2,6-bis(methyloxy)benzamide chiral |

TABLE 5-continued

| Ex | Structure | Method | Mass spectrum (Electrospray LC/MS), API+ Ret. time (min) | Name |
|---|---|---|---|---|
| 70 | 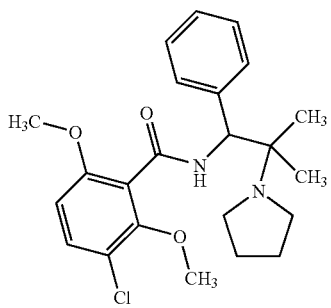 | PE | Found 417 (MH+) $C_{23}H_{29}{}^{35}ClN_2O_3$ requires 416; 2.4* | (±)-3-chloro-2,6-bis(methyloxy)-N-[2-methyl-1-phenyl-2-(1-pyrrolidinyl)propyl]benzamide |
| 71 | 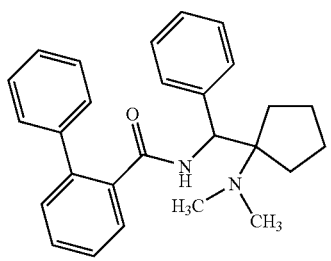 | PE | Found 399 (MH+) $C_{27}H_{30}N_2O$ requires 398; 2.51* | N-[[1-(dimethylamino)cyclopentyl](phenyl)methyl]-2-biphenylcarboxamide chiral |
| 72 | 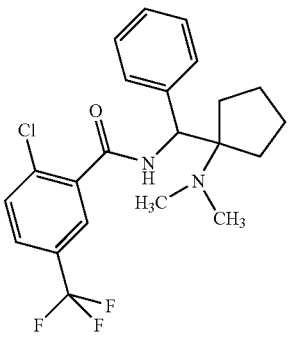 | PE | Found 425 (MH+) $C_{22}H_{24}{}^{35}ClF_3N_2O$ requires 424; 2.48* | 2-chloro-N-[[1-(dimethylamino)cyclopentyl](phenyl)methyl]-5-(trifluoromethyl)benzamide chiral |
| 73 | 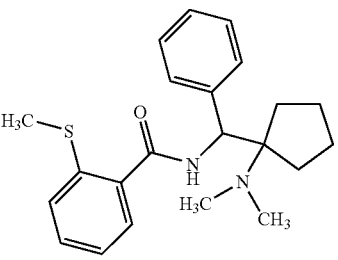 | PE | Found 369 (MH+) $C_{22}H_{28}N_2OS$ requires 368; 2.58* | N-[[1-(dimethylamino)cyclopentyl](phenyl)methyl]-2-(methylthio)benzamide chiral |
| 74 | 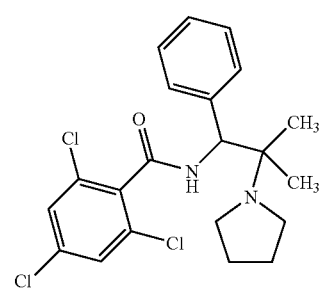 | PE | Found 425 (MH+) $C_{21}H_{23}{}^{35}Cl_3N_2O$ requires 424; 2.93* | (±)-2,4,6-trichloro-N-[2-methyl-1-phenyl-2-(1-pyrrolidinyl)propyl]benzamide |

TABLE 5-continued

| Ex | Structure | Method | Mass spectrum (Electrospray LC/MS), API+ Ret. time (min) | Name |
|---|---|---|---|---|
| 75 | 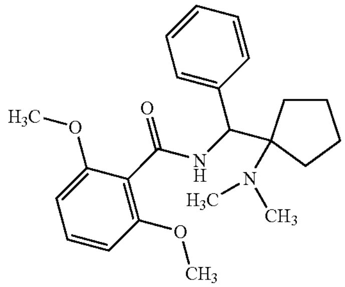 | PE | Found 383 (MH+) $C_{23}H_{30}N_2O_3$ requires 382; 2.88* | N-[[1-(dimethylamino)cyclopentyl](phenyl)methyl]-2,6-bis(methyloxy)benzamide chiral |
| 76 | 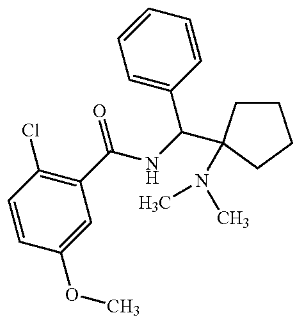 | PE | Found 387 (MH+) $C_{22}H_{27}{}^{35}ClN_2O_2$ requires 386; 2.56* | 2-chloro-N-[[1-(dimethylamino)cyclopentyl](phenyl)methyl]-5-(methyloxy)benzamide chiral |
| 77 | 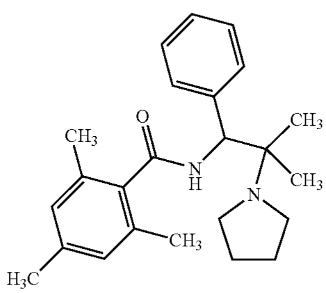 | PE | Found 365 (MH+) $C_{24}H_{32}N_2O$ requires 364; 2.46* | (±)-2,4,6-trimethyl-N-[2-methyl-1-phenyl-2-(1-pyrrolidinyl)propyl]benzamide |
| 78 | 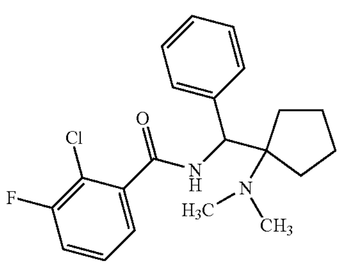 | PE | Found 375 (MH+) $C_{21}H_{24}{}^{35}ClFN_2O$ requires 374; 2.99* | 2-chloro-N-[[1-(dimethylamino)cyclopentyl](phenyl)methyl]-3-fluorobenzamide chiral |
| 79 | 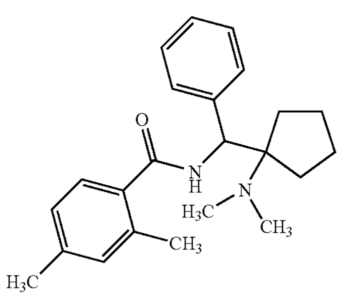 | PE | Found 351 (MH+) $C_{23}H_{30}N_2O$ requires 350; 2.96* | N-[[1-(dimethylamino)cyclopentyl](phenyl)methyl]-2,4-dimethylbenzamide chiral |

TABLE 5-continued

| Ex | Structure | Method | Mass spectrum (Electrospray LC/MS), API+ Ret. time (min) | Name |
|---|---|---|---|---|
| 80 | 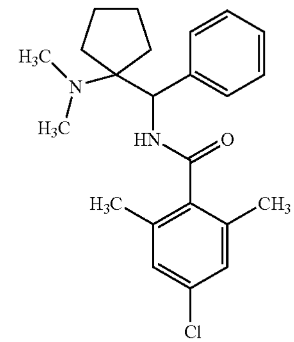 | E | Found 385 (MH+) C₂₃H₂₉³⁵ClN₂O requires 384; 2.19 | 4-chloro-N-[[1-(dimethylamino)cyclopentyl](phenyl)methyl]-2,6-dimethylbenzamide chiral |
| 81 | 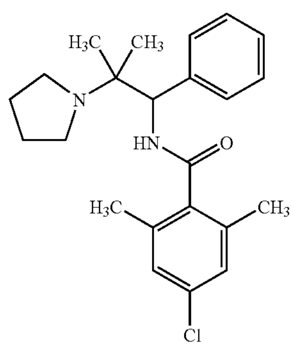 | E | Found 385 (MH+) C₂₃H₂₉³⁵ClN₂O requires 384; 2.07 | 4-chloro-2,6-dimethyl-N-[2-methyl-1-phenyl-2-(1-pyrrolidinyl)propyl]benzamide chiral |
| 82 | 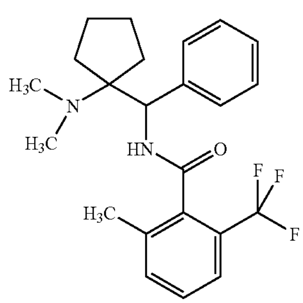 | E | Found 405 (MH+) C₂₃H₂₇F₃N₂O requires 404; 1.91 | N-[[1-(dimethylamino)cyclopentyl](phenyl)methyl]-2-methyl-6-(trifluoromethyl)benzamide chiral |
| 83 | 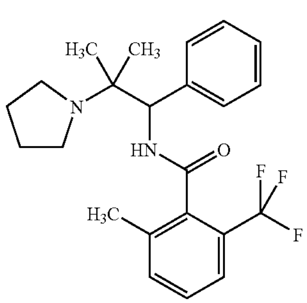 | E | Found 405 (MH+) C₂₃H₂₇F₃N₂O requires 404; 1.91 | 2-methyl-N-[2-methyl-1-phenyl-2-(1-pyrrolidinyl)propyl]-6-(trifluoromethyl)benzamide chiral |

TABLE 5-continued

| Ex | Structure | Method | Mass spectrum (Electrospray LC/MS), API+ Ret. time (min) | Name |
|---|---|---|---|---|
| 84 | 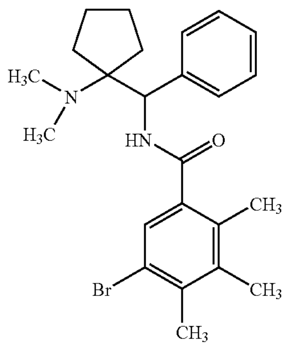 | A | Found 443 (MH+) C$_{24}$H$_{31}$$^{79}$BrN$_2$O requires 442; 2.27 | 5-bromo-N-[[1-(dimethylamino)cyclopentyl](phenyl)methyl]-2,3,4-trimethylbenzamide chiral |
| 85 | 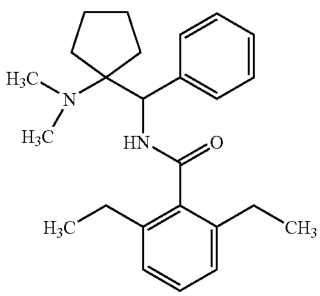 | E | Found 379 (MH+) C$_{25}$H$_{34}$N$_2$O requires 378; 2.07 | N-[[1-(dimethylamino)cyclopentyl](phenyl)methyl]-2,6-diethylbenzamide chiral |
| 86 | 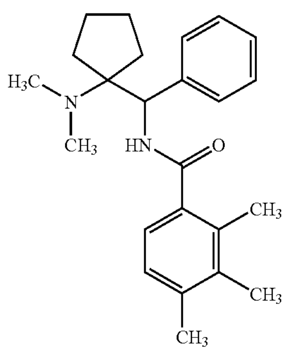 | E | Found 365 (MH+) C$_{24}$H$_{32}$N$_2$O requires 364; 2.06 | N-[[1-(dimethylamino)cyclopentyl](phenyl)methyl]-2,3,4-trimethylbenzamide chiral |
| 87 | 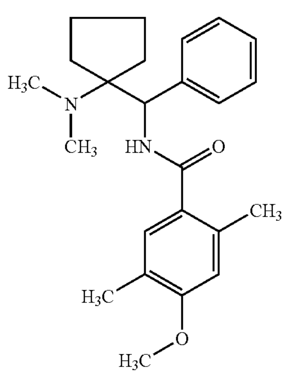 | E | Found 381 (MH+) C$_{24}$H$_{32}$N$_2$O$_2$ requires 380; 2.00 | N-[[1-(dimethylamino)cyclopentyl](phenyl)methyl]-2,5-dimethyl-4-(methyloxy)benzamide chiral |

TABLE 5-continued

| Ex | Structure | Method | Mass spectrum (Electrospray LC/MS), API+ Ret. time (min) | Name |
|---|---|---|---|---|
| 88 | 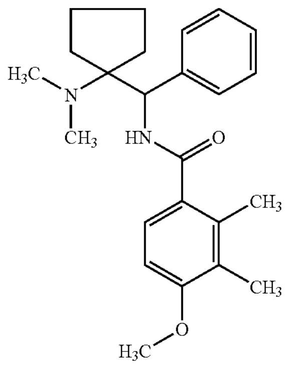 | E | Found 381 (MH+) $C_{24}H_{32}N_2O_2$ requires 380; 1.96 | N-[[1-(dimethylamino)cyclopentyl](phenyl)methyl]-2,3-dimethyl-4-(methyloxy)benzamide chiral |
| 89 | 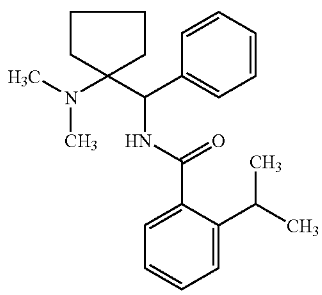 | E | Found 365 (MH+) $C_{24}H_{32}N_2O$ requires 364; 2.02 | N-[[1-(dimethylamino)cyclopentyl](phenyl)methyl]-2-(1-methylethyl)benzamide chiral |
| 90 | 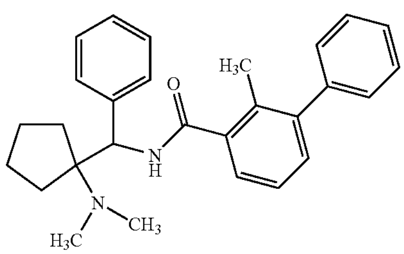 | P | Found 413 (MH+) $C_{28}H_{32}N_2O$ requires 412; | (±)-N-[[1-(dimethylamino)cyclopentyl](phenyl)methyl]-2-methyl-3-biphenylcarboxamide |
| 91 | 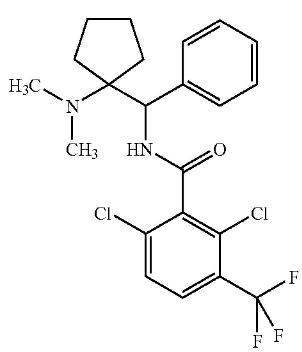 | P# | Found 459 (MH+) $C_{22}H_{23}{}^{35}Cl_2F_3N_2O$ requires 458; 2.11 | 2,6-dichloro-N-[[1-(dimethylamino)cyclopentyl](phenyl)methyl]-3-(trifluoromethyl)benzamide chiral |

TABLE 5-continued

| Ex | Structure | Method | Mass spectrum (Electrospray LC/MS), API+ Ret. time (min) | Name |
|---|---|---|---|---|
| 92 | 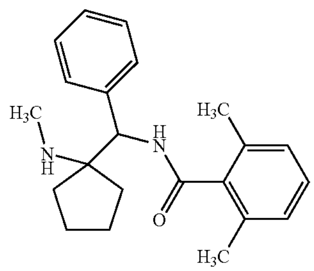 | H | Found 337 (MH+) $C_{22}H_{28}N_2O$ requires 336; 1.88 | (±)-2,6-dimethyl-N-[[1-(methylamino)cyclopentyl](phenyl)methyl]benzamide |
| 93 | 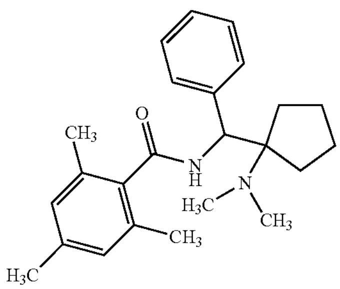 | P | Found 365 (MH+) $C_{24}H_{32}N_2O$ requires 364; 1.97 | N-[[1-(dimethylamino)cyclopentyl](phenyl)methyl]-2,4,6-trimethylbenzamide chiral |
| 94 | 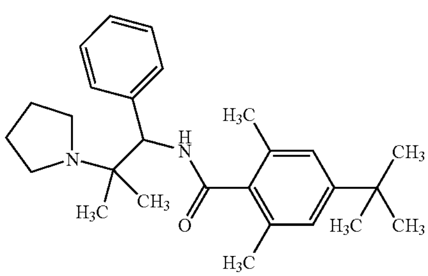 | P | Found 407 (MH+) $C_{27}H_{38}N_2O$ requires 406; 2.34 | (±)-4-(1,1-dimethylethyl)-2,6-dimethyl-N-[2-methyl-1-phenyl-2-(1-pyrrolidinyl)propyl]benzamide |
| 95 | 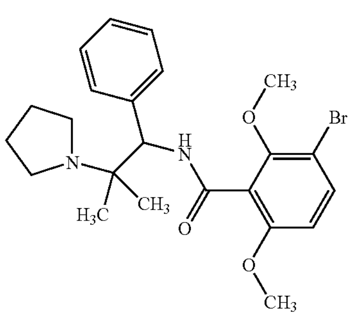 | P | Found 461 (MH+) $C_{23}H_{29}{}^{79}BrN_2O_3$ requires 460; 1.98 | (±)-3-bromo-2,6-bis(methyloxy)-N-[2-methyl-1-phenyl-2-(1-pyrrolidinyl)propyl]benzamide |
| 96 | 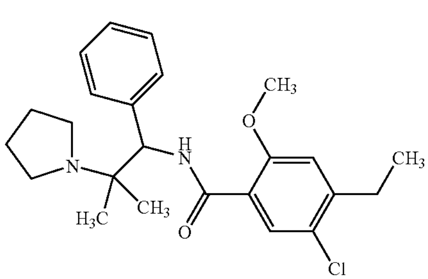 | P | Found 415 (MH+) $C_{24}H_{31}{}^{35}ClN_2O_2$ requires 414; 2.36 | (±)-5-chloro-4-ethyl-2-(methyloxy)-N-[2-methyl-1-phenyl-2-(1-pyrrolidinyl)propyl]benzamide |

TABLE 5-continued

| Ex | Structure | Method | Mass spectrum (Electrospray LC/MS), API+ Ret. time (min) | Name |
|---|---|---|---|---|
| 97 | 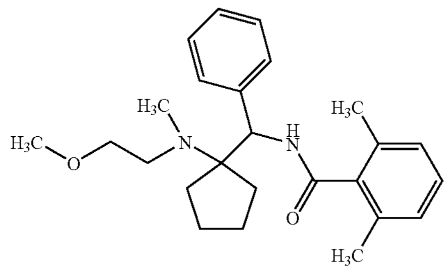 | A | Found 395 (MH+) C25H34N2O2 requires 394; 2.14 | (±)-2,6-dimethyl-N-[(1-{methyl[2-(methyloxy)ethyl]amino}cyclopentyl)(phenyl)methyl]benzamide |
| 98 | 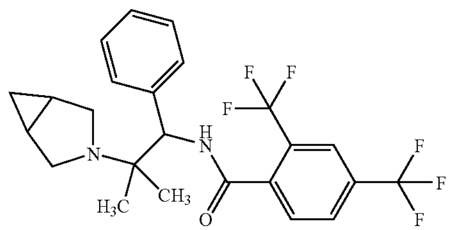 | A | Found 471 (MH+) C24H24F6N2O requires 470; 2.29 | (±)-N-[2-(3-azabicyclo[3.1.0]hex-3-yl)-2-methyl-1-phenylpropyl]-2,4-bis(trifluoromethyl)benzamide |
| 99 | 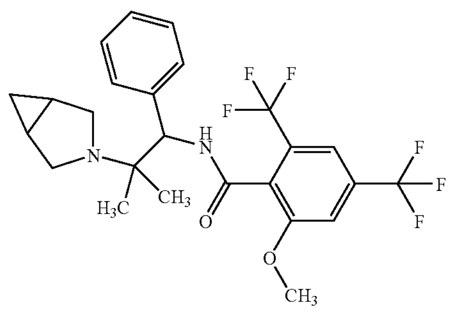 | H | Found 501 (MH+) C25H26F6N2O2 requires 500; 2.30 | (±)-N-[2-(3-azabicyclo[3.1.0]hex-3-yl)-2-methyl-1-phenylpropyl]-2-(methyloxy)-4,6-bis(trifluoromethyl)benzamide |
| 100 | 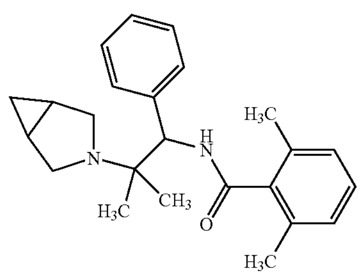 | A | Found 363 (MH+) C24H30N2O requires 362; 1.94 | (±)-N-[2-(3-azabicyclo[3.1.0]hex-3-yl)-2-methyl-1-phenylpropyl]-2,6-dimethylbenzamide |
| 101 | 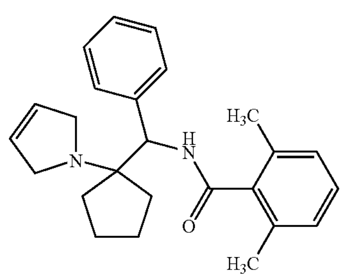 | H | Found 375 (MH+) C25H30N2O requires 374; 1.94 | (±)-N-[[1-(2,5-dihydro-1H-pyrrol-1-yl)cyclopentyl](phenyl)methyl]-2,6-dimethylbenzamide |

TABLE 5-continued

| Ex | Structure | Method | Mass spectrum (Electrospray LC/MS), API+ Ret. time (min) | Name |
|---|---|---|---|---|
| 102 | 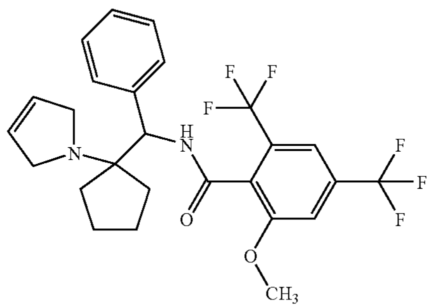 | H | Found 513 (MH+) C$_{26}$H$_{26}$F$_6$N$_2$O$_2$ requires 512; 2.35 | (±)-N-[[1-(2,5-dihydro-1H-pyrrol-1-yl)cyclopentyl](phenyl)methyl]-2-(methyloxy)-4,6-bis(trifluoromethyl)benzamide |
| 103 | 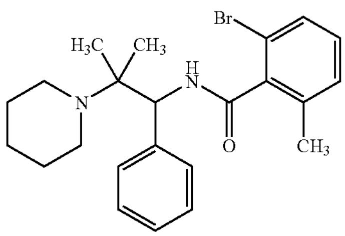 | H | Found 429 (MH+) C$_{23}$H$_{29}$$^{79}$BrN$_2$O requires 428; 2.02 | (±)-2-bromo-6-methyl-N-[2-methyl-1-phenyl-2-(1-piperidinyl)propyl]benzamide |
| 104 | 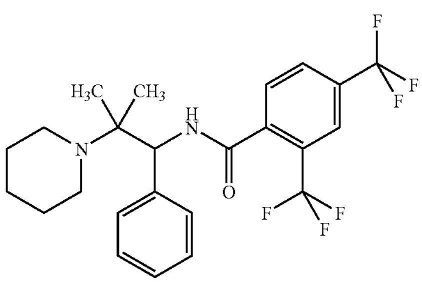 | H | Found 473 (MH+) C$_{24}$H$_{26}$F$_6$N$_2$O requires 472; 2.18 | (±)-N-[2-methyl-1-phenyl-2-(1-piperidinyl)propyl]-2,4-bis(trifluoromethyl)benzamide |
| 105 | 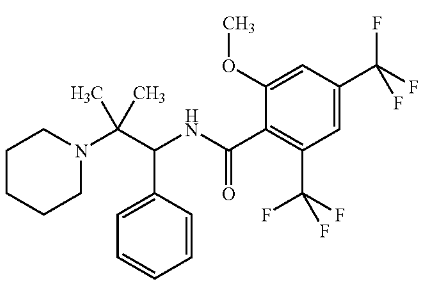 | H | Found 503 (MH+) C$_{25}$H$_{28}$F$_6$N$_2$O$_2$ requires 502; 2.28 | (±)-2-(methyloxy)-N-[2-methyl-1-phenyl-2-(1-piperidinyl)propyl]-4,6-bis(trifluoromethyl)benzamide |
| 106 | 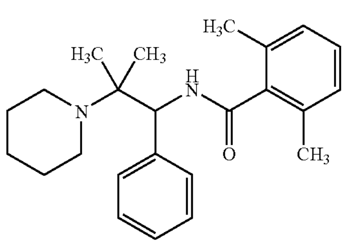 | H | Found 365 (MH+) C$_{24}$H$_{32}$N$_2$O requires 364; 1.88 | (±)-2,6-dimethyl-N-[2-methyl-1-phenyl-2-(1-piperidinyl)propyl]benzamide |

TABLE 5-continued

| Ex | Structure | Method | Mass spectrum (Electrospray LC/MS), API+ Ret. time (min) | Name |
|---|---|---|---|---|
| 107 | 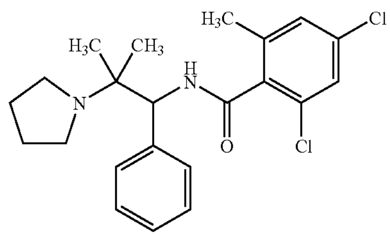 | H | Found 405 (MH+) C$_{22}$H$_{26}$$^{35}$Cl$_2$N$_2$O requires 404; 2.10 | 2,4-dichloro-6-methyl-N-[2-methyl-1-phenyl-2-(1-pyrrolidinyl)propyl]benzamide chiral |
| 108 | 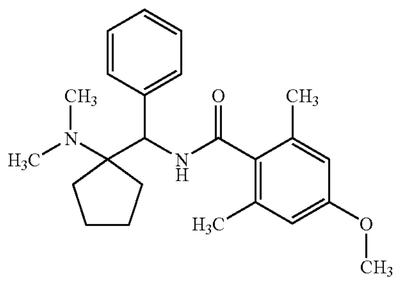 | H | Found 381 (MH+) C$_{24}$H$_{32}$N$_2$O$_2$ requires 380; 1.89 | N-[[1-(dimethylamino)cyclopentyl](phenyl)methyl]-2,6-dimethyl-4-(methyloxy)benzamide chiral |
| 109 | 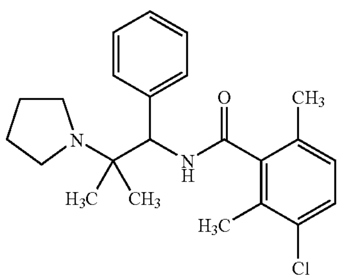 | P | Found 385 (MH+) C$_{23}$H$_{29}$$^{35}$ClN$_2$O requires 384; 2.11 | 3-chloro-2,6-dimethyl-N-[2-methyl-1-phenyl-2-(1-pyrrolidinyl)propyl]benzamide chiral |
| 110 | 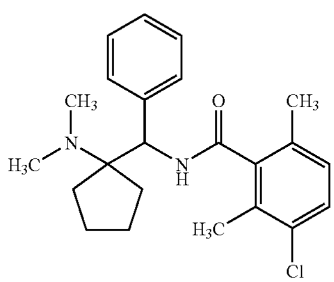 | P | Found 385 (MH+) C$_{23}$H$_{29}$$^{35}$ClN$_2$O requires 384; 2.12 | 3-chloro-N-[[1-(dimethylamino)cyclopentyl](phenyl)methyl]-2,6-dimethylbenzamide chiral |
| 111 | 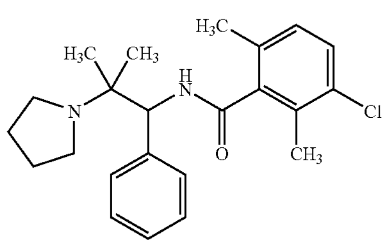 | H | Found 385 (MH+) C$_{23}$H$_{29}$$^{35}$ClN$_2$O requires 384; 2.02 | (±)-3-chloro-2,6-dimethyl-N-[2-methyl-1-phenyl-2-(1-pyrrolidinyl)propyl]benzamide |

TABLE 5-continued

| Ex | Structure | Method | Mass spectrum (Electrospray LC/MS), API+ Ret. time (min) | Name |
|---|---|---|---|---|
| 112 | 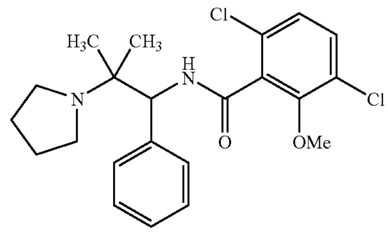 | H | Found 421 (MH+) $C_{22}H_{26}{}^{35}Cl_2N_2O_2$ requires 420; 2.02 | (±)-3,6-dichloro-2-(methyloxy)-N-[2-methyl-1-phenyl-2-(1-pyrrolidinyl)propyl]benzamide |
| 113 | 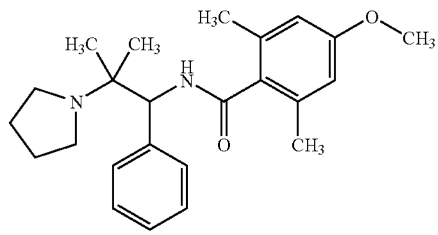 | H | Found 381 (MH+) $C_{24}H_{32}N_2O_2$ requires 380; 1.86 | (±)-2,6-dimethyl-4-(methyloxy)-N-[2-methyl-1-phenyl-2-(1-pyrrolidinyl)propyl]benzamide |
| 114 | 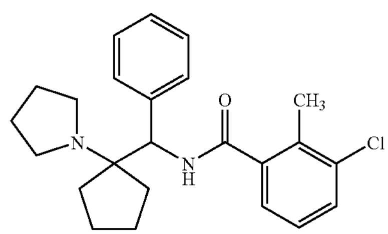 | H | Found 397 (MH+) $C_{24}H_{29}{}^{35}ClN_2O$ requires 396; 2.13 | (±)-3-chloro-2-methyl-N-{phenyl[1-(1-pyrrolidinyl)cyclopentyl]methyl}benzamide |
| 115 | 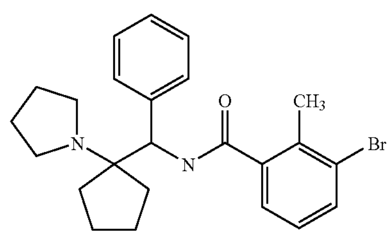 | H | Found 441 (MH+) $C_{24}H_{29}{}^{79}BrN_2O$ requires 440; 2.15 | (±)-3-bromo-2-methyl-N-{phenyl[1-(1-pyrrolidinyl)cyclopentyl]methyl}benzamide |
| 116 | 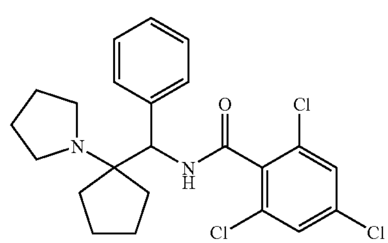 | H | Found 451 (MH+) $C_{23}H_{25}{}^{35}Cl_3N_2O$ requires 450; 2.14 | (±)-2,4,6-trichloro-N-{phenyl[1-(1-pyrrolidinyl)cyclopentyl]methyl}benzamide |
| 117 | 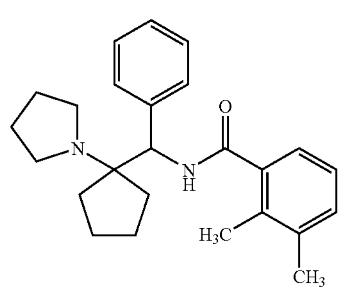 | H | Found 377 (MH+) $C_{25}H_{32}N_2O$ requires 376; 2.02 | (±)-2,3-dimethyl-N-{phenyl[1-(1-pyrrolidinyl)cyclopentyl]methyl}benzamide |

TABLE 5-continued

| Ex | Structure | Method | Mass spectrum (Electrospray LC/MS), API+ Ret. time (min) | Name |
|---|---|---|---|---|
| 118 | 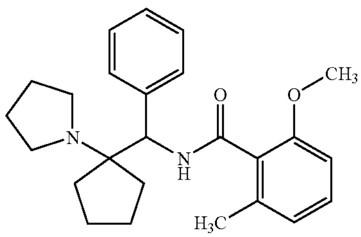 | H | Found 393 (MH+) $C_{25}H_{32}N_2O_2$ requires 392; 1.95 | (±)-2-methyl-6-(methyloxy)-N-{phenyl[1-(1-pyrrolidinyl)cyclopentyl]methyl}benzamide |
| 119 | 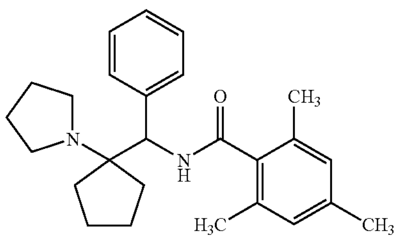 | H | Found 391 (MH+) $C_{26}H_{34}N_2O$ requires 390; 2.08 | (±)-2,4,6-trimethyl-N-{phenyl[1-(1-pyrrolidinyl)cyclopentyl]methyl}benzamide |
| 120 | 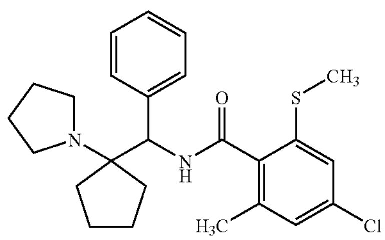 | H | Found 443 (MH+) $C_{25}H_{31}{}^{35}ClN_2OS$ requires 442; 2.18 | (±)-4-chloro-2-methyl-6-(methylthio)-N-{phenyl[1-(1-pyrrolidinyl)cyclopentyl]methyl}benzamide |
| 121 | 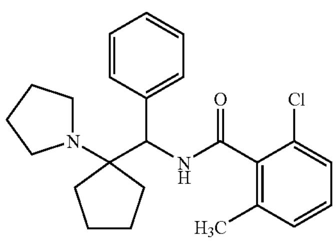 | H | Found 397 (MH+) $C_{24}H_{29}{}^{35}ClN_2O$ requires 396; 2.08 | (±)-2-chloro-6-methyl-N-{phenyl[1-(1-pyrrolidinyl)cyclopentyl]methyl}benzamide |
| 122 | 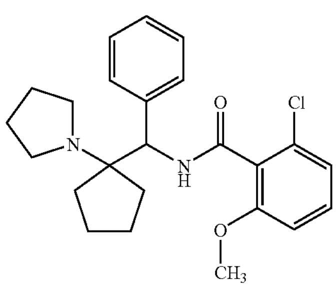 | H | Found 413 (MH+) $C_{24}H_{29}{}^{35}ClN_2O_2$ requires 412; 1.92 | (±)-2-chloro-6-(methyloxy)-N-{phenyl[1-(1-pyrrolidinyl)cyclopentyl]methyl}benzamide |
| 123 | 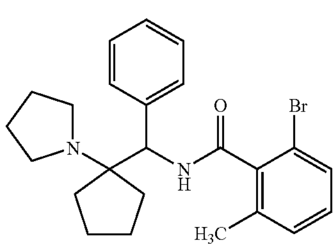 | H | Found 441 (MH+) $C_{24}H_{29}{}^{79}BrN_2O$ requires 440; 1.97 | (±)-2-bromo-6-methyl-N-{phenyl[1-(1-pyrrolidinyl)cyclopentyl]methyl}benzamide |

TABLE 5-continued

| Ex | Structure | Method | Mass spectrum (Electrospray LC/MS), API+ Ret. time (min) | Name |
|---|---|---|---|---|
| 124 | 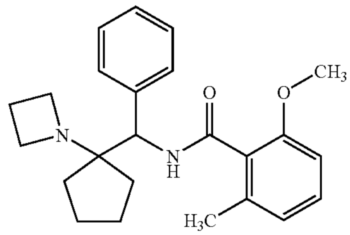 | H | Found 379 (MH+) C24H30N2O2 requires 378; 1.97 | (±)-N-[[1-(1-azetidinyl)cyclopentyl](phenyl)methyl]-2-methyl-6-(methyloxy)benzamide |
| 125 | 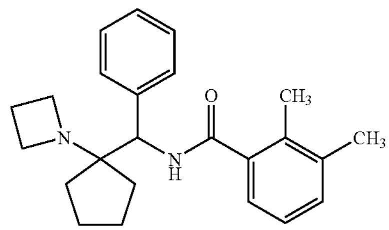 | A | Found 363 (MH+) C24H30N2O requires 362; 1.99 | (±)-N-[[1-(1-azetidinyl)cyclopentyl](phenyl)methyl]-2,3-dimethylbenzamide |
| 126 | 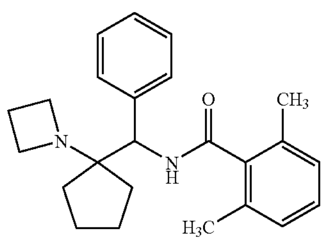 | A | Found 363 (MH+) C24H30N2O requires 362; 1.90 | (±)-N-[[1-(1-azetidinyl)cyclopentyl](phenyl)methyl]-2,6-dimethylbenzamide |
| 127 | 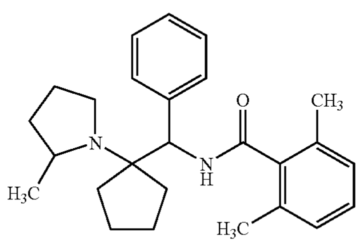 | A | Found 391 (MH+) C26H34N2O requires 390; 2.06 | (±)-2,6-dimethyl-N-[[1-(2-methyl-1-pyrrolidinyl)cyclopentyl](phenyl)methyl]benzamide |
| 128 | 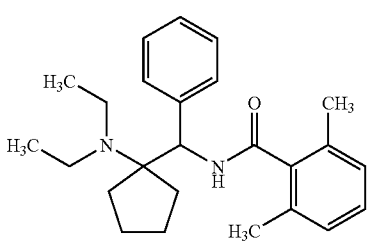 | A | Found 379 (MH+) C25H34N2O requires 378; 2.04 | (±)-N-[[1-(diethylamino)cyclopentyl](phenyl)methyl]-2,6-dimethylbenzamide |
| 129 | 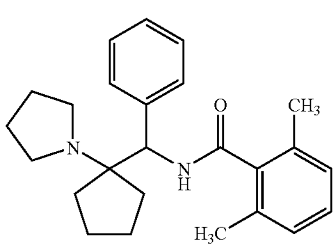 | A | Found 377 (MH+) C25H32N2O requires 376; 1.90 | (±)-2,6-dimethyl-N-{phenyl[1-(1-pyrrolidinyl)cyclopentyl]methyl}benzamide |

TABLE 5-continued

| Ex | Structure | Method | Mass spectrum (Electrospray LC/MS), API+ Ret. time (min) | Name |
|----|-----------|--------|---------|------|
| 130 | 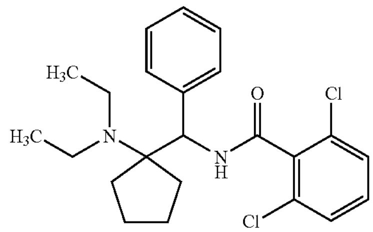 | H | Found 419 (MH+) $C_{23}H_{28}{}^{35}Cl_2N_2O$ requires 418; 2.15 | (±)-2,6-dichloro-N-[[1-(diethylamino)cyclopentyl](phenyl)methyl]benzamide |
| 131 | 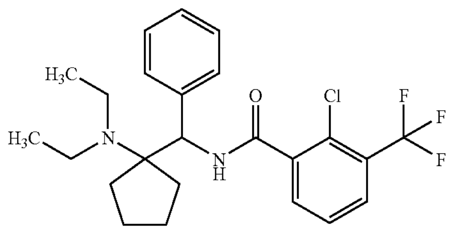 | H | Found 453 (MH+) $C_{24}H_{28}{}^{35}ClF_3N_2O$ requires 452; 2.25 | (±)-2-chloro-N-[[1-(diethylamino)cyclopentyl](phenyl)methyl]-3-(trifluoromethyl)benzamide |
| 132 | 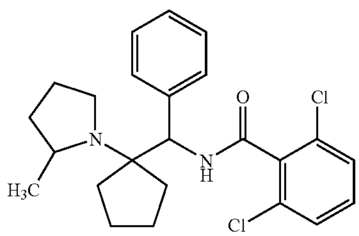 | H | Found 431 (MH+) $C_{24}H_{28}{}^{35}Cl_2N_2O$ requires 430; 1.93 | (±)-2,6-dichloro-N-[[1-(2-methyl-1-pyrrolidinyl)cyclopentyl](phenyl)methyl]benzamide |
| 133 | 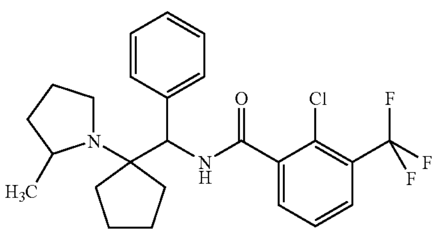 | H | Found 465 (MH+) $C_{25}H_{28}{}^{35}ClF_3N_2O$ requires 464; 2.15 | (±)-2-chloro-N-[[1-(2-methyl-1-pyrrolidinyl)cyclopentyl](phenyl)methyl]-3-(trifluoromethyl)benzamide |
| 134 | 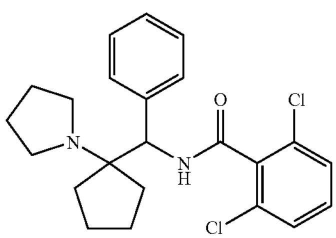 | H | Found 417 (MH+) $C_{23}H_{26}{}^{35}Cl_2N_2O$ requires 416; 1.99 | (±)-2,6-dichloro-N-{phenyl[1-(1-pyrrolidinyl)cyclopentyl]methyl}benzamide |
| 135 | 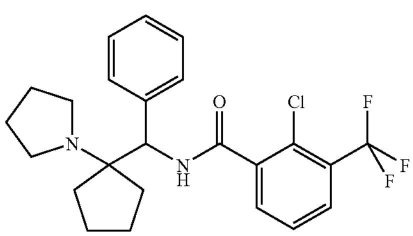 | H | Found 451 (MH+) $C_{24}H_{26}{}^{35}ClF_3N_2O$ requires 450 | (±)-2-chloro-N-{phenyl[1-(1-pyrrolidinyl)cyclopentyl]methyl}-3-(trifluoromethyl)benzamide |

TABLE 5-continued

| Ex | Structure | Method | Mass spectrum (Electrospray LC/MS), API+ Ret. time (min) | Name |
|---|---|---|---|---|
| 136 | 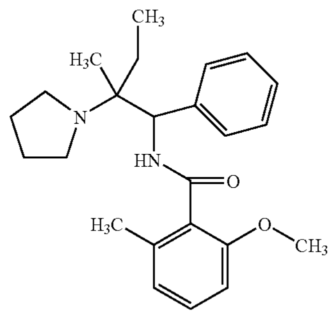 | E | Found 381 (MH+) $C_{24}H_{32}N_2O_2$ requires 380; 1.83 & 1.87 | (±)-2-methyl-6-(methyloxy)-N-[2-methyl-1-phenyl-2-(1-pyrrolidinyl)butyl]benzamide |
| 137 | 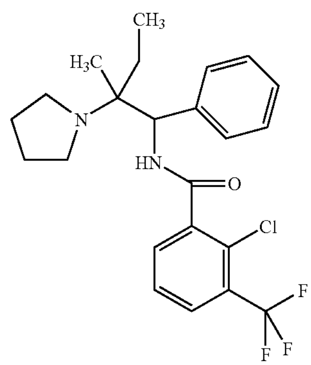 | A | Found 439 (MH+) $C_{23}H_{26}{}^{35}ClF_3N_2O$ requires 438; 2.11 & 2.17. | (±)-2-chloro-N-[2-methyl-1-phenyl-2-(1-pyrrolidinyl)butyl]-3-(trifluoromethyl)benzamide |
| 138 | 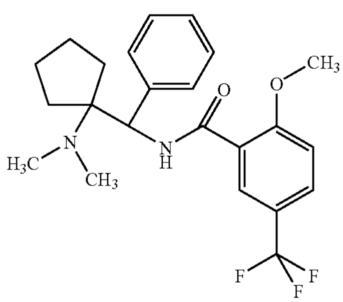 | P | Found 421 (MH+) $C_{23}H_{27}F_3N_2O_2$ requires 420; 2.19. | (±)-N-[[1-(dimethylamino)cyclopentyl](phenyl)methyl]-2-(methyloxy)-5-(trifluoromethyl)benzamide |
| 139 | 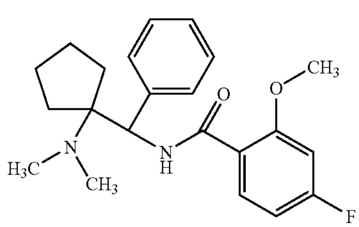 | P | Found 371 (MH+) $C_{22}H_{27}FN_2O_2$ requires 370; 1.99. | (±)-N-[[1-(dimethylamino)cyclopentyl](phenyl)methyl]-4-fluoro-2-(methyloxy)benzamide |

TABLE 5-continued

| Ex | Structure | Method | Mass spectrum (Electrospray LC/MS), API+ Ret. time (min) | Name |
| --- | --- | --- | --- | --- |
| 140 | 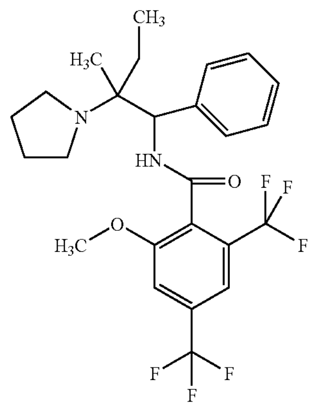 | E | Found 503 (MH+) $C_{25}H_{28}F_6N_2O_2$ requires 502; 2.23 & 2.27. | (±)-2-(methyloxy)-N-[2-methyl-1-phenyl-2-(1-pyrrolidinyl)butyl]-4,6-bis(trifluoromethyl)benzamide |
| 141 | 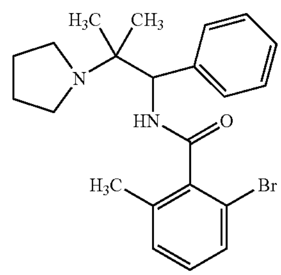 | E | Found 415 (MH+) $C_{22}H_{27}{}^{79}BrN_2O$ requires 414; 1.84. | 2-bromo-6-methyl-N-[2-methyl-1-phenyl-2-(1-pyrrolidinyl)propyl]benzamide chiral |
| 142 | 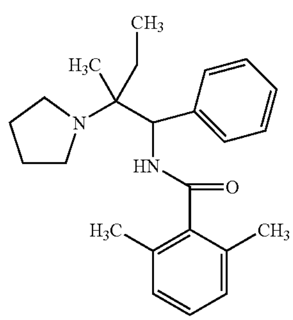 | A | Found 365 (MH+) $C_{24}H_{32}N_2O$ requires 364; 1.86 & 1.94. | (±)-2,6-dimethyl-N-[2-methyl-1-phenyl-2-(1-pyrrolidinyl)butyl]benzamide |
| 143 | 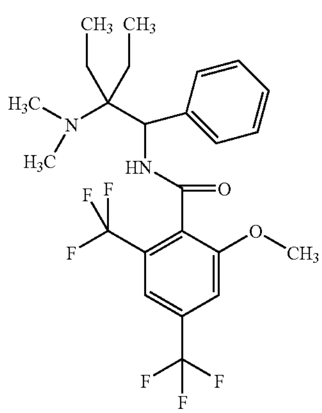 | E | Found 491 (MH+) $C_{24}H_{28}F_6N_2O_2$ requires 490; 2.26. | (±)-N-[2-(dimethylamino)-2-ethyl-1-phenylbutyl]-2-(methyloxy)-4,6-bis(trifluoromethyl)benzamide |

TABLE 5-continued

| Ex | Structure | Method | Mass spectrum (Electrospray LC/MS), API+ Ret. time (min) | Name |
|---|---|---|---|---|
| 144 | 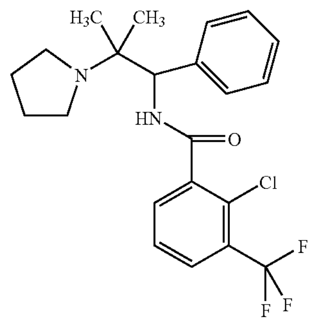 | P | Found 425 (MH+) $C_{22}H_{24}{}^{35}ClF_3N_2O$ requires 424; 2.0. | (±)-2-chloro-N-[2-methyl-1-phenyl-2-(1-pyrrolidinyl)propyl]-3-(trifluoromethyl)benzamide |
| 145 | 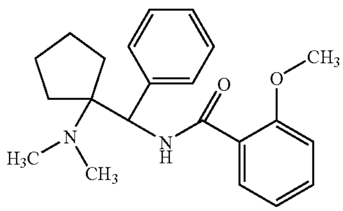 | P | Found 353 (MH+) $C_{22}H_{28}N_2O_2$ requires 352; 1.93. | (±)-N-[[1-(dimethylamino)cyclopentyl](phenyl)methyl]-2-(methyloxy)benzamide |
| 146 | 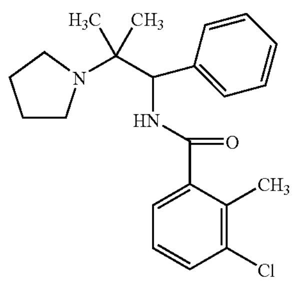 | E | Found 371 (MH+) $C_{22}H_{27}{}^{35}ClN_2O$ requires 370; 1.98. | 3-chloro-2-methyl-N-[2-methyl-1-phenyl-2-(1-pyrrolidinyl)propyl]benzamide chiral |
| 147 | 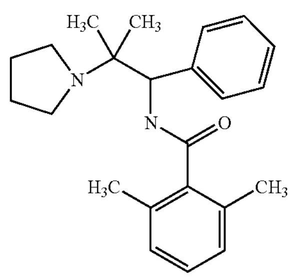 | E | Found 351 (MH+) $C_{23}H_{30}N_2O$ requires 350; 1.89. | 2,6-dimethyl-N-[2-methyl-1-phenyl-2-(1-pyrrolidinyl)propyl]benzamide chiral |
| 148 | 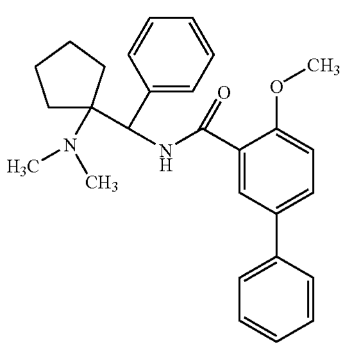 | P | Found 429 (MH+) $C_{28}H_{32}N_2O_2$ requires 428; 2.32. | (±)-N-[[1-(dimethylamino)cyclopentyl](phenyl)methyl]-4-(methyloxy)-3-biphenylcarboxamide |

TABLE 5-continued

| Ex | Structure | Method | Mass spectrum (Electrospray LC/MS), API+ Ret. time (min) | Name |
|---|---|---|---|---|
| 149 | 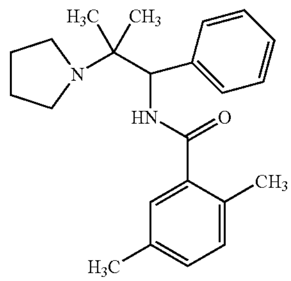 | E | Found 351 (MH+) $C_{23}H_{30}N_2O$ requires 350; 1.94. | 2,5-dimethyl-N-[2-methyl-1-phenyl-2-(1-pyrrolidinyl)propyl]benzamide chiral |
| 150 | 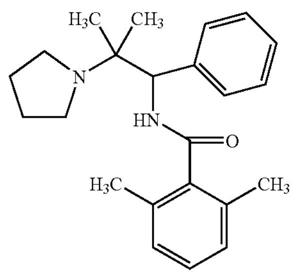 | P | Found 351 (MH+) $C_{23}H_{30}N_2O$ requires 350 1.80. | (±)-2,6-dimethyl-N-[2-methyl-1-phenyl-2-(1-pyrrolidinyl)propyl]benzamide |
| 151 | 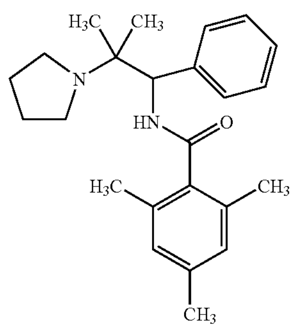 | E | Found 365 (MH+) $C_{24}H_{32}N_2O$ requires 364; 1.88. | 2,4,6-trimethyl-N-[2-methyl-1-phenyl-2-(1-pyrrolidinyl)propyl]benzamide chiral |
| 152 | 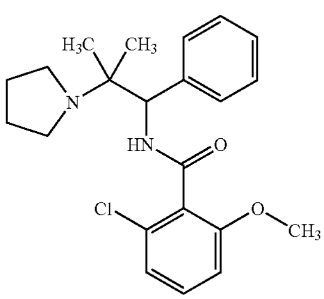 | E | Found 387 (MH+) $C_{22}H_{27}{}^{35}ClN_2O_2$ requires 386; 1.84. | 2-chloro-6-(methyloxy)-N-[2-methyl-1-phenyl-2-(1-pyrrolidinyl)propyl]benzamide chiral |
| 153 | 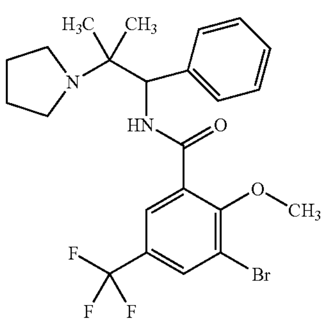 | E | Found 499 (MH+) $C_{23}H_{26}{}^{79}BrF_3N_2O_2$ requires 498; 2.28. | 3-bromo-2-(methyloxy)-N-[2-methyl-1-phenyl-2-(1-pyrrolidinyl)propyl]-5-(trifluoromethyl)benzamide chiral |

TABLE 5-continued

| Ex | Structure | Method | Mass spectrum (Electrospray LC/MS), API+ Ret. time (min) | Name |
|---|---|---|---|---|
| 154 | 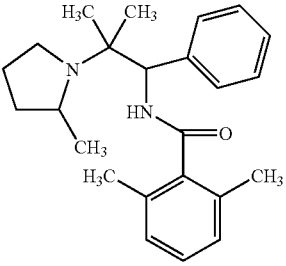 | E | Found 365 (MH+) C24H32N2O2 requires 364; 2.00. | (±)-2,6-dimethyl-N-[2-methyl-(2-methyl-1-pyrrolidinyl)-1-phenylpropyl]benzamide |
| 155 | 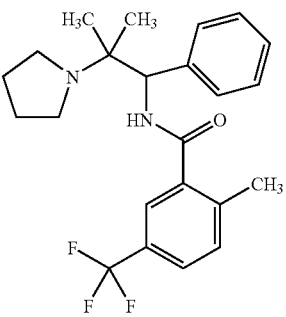 | E | Found 405 (MH+) C23H27F3N2O requires 404; 2.19. | 2-methyl-N-[2-methyl-1-phenyl-2-(1-pyrrolidinyl)propyl]-5-(trifluoromethyl)benzamide chiral |
| 156 | 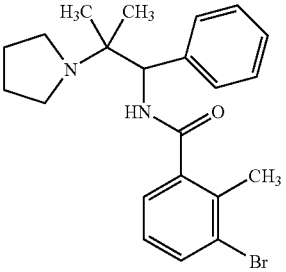 | E | Found 415 (MH+) C22H27·79BrN2O requires 414; 2.12 | 3-bromo-2-methyl-N-[2-methyl-1-phenyl-2-(1-pyrrolidinyl)propyl]benzamide chiral |
| 157 | 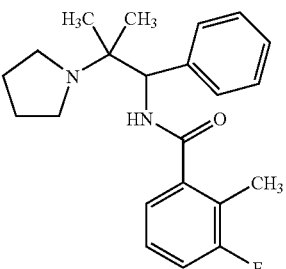 | E | Found 355 (MH+) C22H27FN2O requires 354; 1.96. | 3-fluoro-2-methyl-N-[2-methyl-1-phenyl-2-(1-pyrrolidinyl)propyl]benzamide chiral |
| 158 | 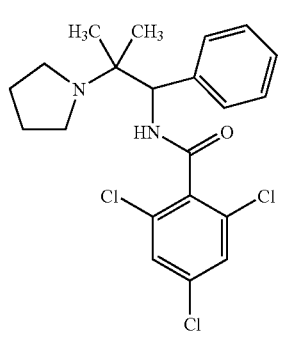 | E | Found 425 (MH+) C21H23·35Cl3N2O requires 424; 2.11. | 2,4,6-trichloro-N-[2-methyl-1-phenyl-2-(1-pyrrolidinyl)propyl]benzamide chiral |

TABLE 5-continued

| Ex | Structure | Method | Mass spectrum (Electrospray LC/MS), API+ Ret. time (min) | Name |
|---|---|---|---|---|
| 159 | 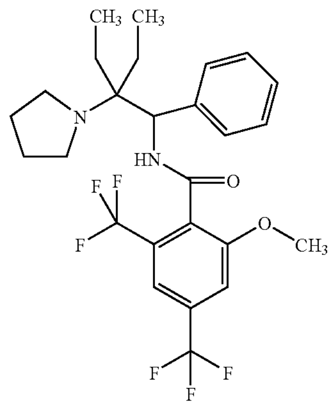 | E | Found 517 (MH+) C26H30F6N2O2 requires 516; 2.32. | (±)-N-[2-ethyl-1-phenyl-2-(1-pyrrolidinyl)butyl]-2-(methyloxy)-4,6-bis(trifluoromethyl)benzamide |
| 160 | 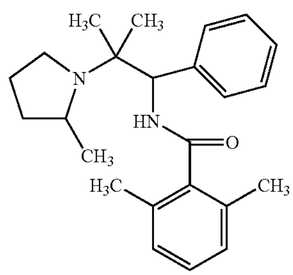 | E | Found 365 (MH+) C24H32N2O requires 364; 1.96. | (±)-2,6-dimethyl-N-[2-methyl-2-(2-methyl-1-pyrrolidinyl)-1-phenylpropyl]benzamide |
| 161 | 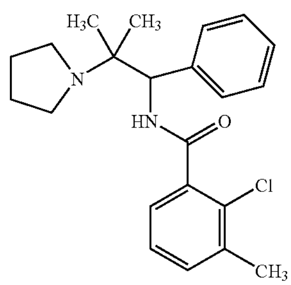 | E | Found 371 (MH+) C22H27<sup>35</sup>ClN2O requires 370; 1.89. | 2-chloro-3-methyl-N-[2-methyl-1-phenyl-2-(1-pyrrolidinyl)propyl]benzamide chiral |
| 162 | 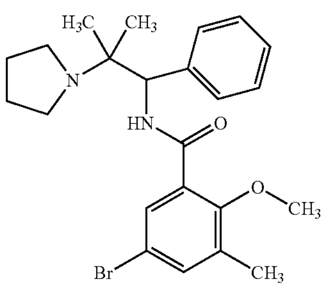 | E | Found 445 (MH+) C23H29<sup>79</sup>BrN2O2 requires 444; 2.15 | 5-bromo-3-methyl-2-(methyloxy)-N-[2-methyl-1-phenyl-2-(1-pyrrolidinyl)propyl]benzamide chiral |
| 163 | 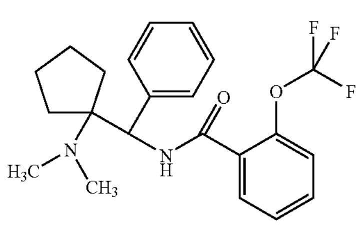 | P | Found 407 (MH+) C22H25F3N2O2 requires 406; 2.05. | (±)-N-[[1-(dimethylamino)cyclopentyl](phenyl)methyl]-2-[(trifluoromethyl)oxy]benzamide |

TABLE 5-continued

| Ex | Structure | Method | Mass spectrum (Electrospray LC/MS), API+ Ret. time (min) | Name |
|---|---|---|---|---|
| 164 | 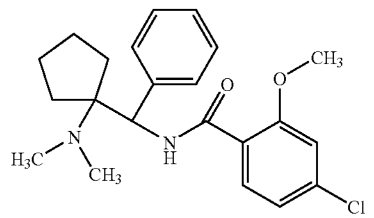 | P | Found 387 (MH+) $C_{22}H_{27}{}^{35}ClN_2O_2$ requires 386; 2.10. | (±)-4-chloro-N-[[1-(dimethylamino)cyclopentyl](phenyl)methyl]-2-(methyloxy)benzamide |
| 165 | 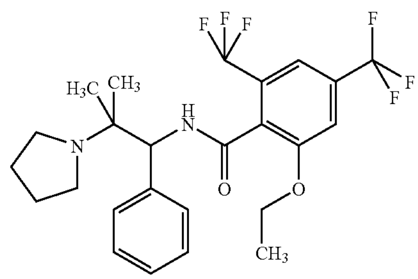 | E | Found 503 (MH+) $C_{25}H_{28}F_6N_2O_2$ requires 502; 2.21. | 2-(ethyloxy)-N-[2-methyl-1-phenyl-2-(1-pyrrolidinyl)propyl]-4,6-bis(trifluoromethyl)benzamide chiral |
| 166 | 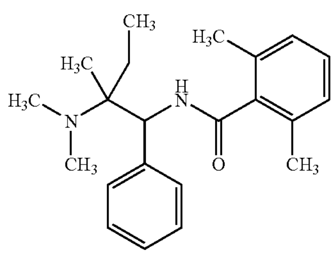 | A | Found 339 (MH+) $C_{22}H_{30}N_2O$ requires 338; 1.75. | (±)-N-[2-(dimethylamino)-2-methyl-1-phenylbutyl]-2,6-dimethylbenzamide |
| 167 | 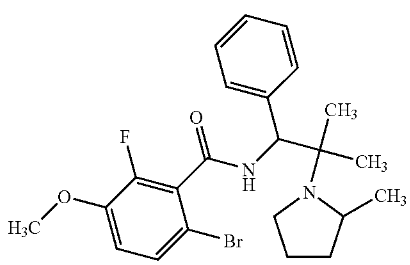 | PE | Found 463 (MH+) $C_{23}H_{28}{}^{79}BrFN_2O_2$ requires 462; 2.44*. | (±)-6-bromo-2-fluoro-N-[2-methyl-2-(2-methyl-1-pyrrolidinyl)-1-phenylpropyl]-3-(methyloxy)benzamide |
| 168 | 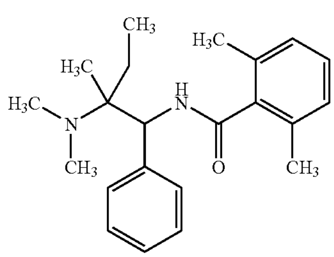 | P | Found 339 (MH+) $C_{22}H_{30}N_2O$ requires 338; 1.71 & 1.76. | (±)-N-[2-(dimethylamino)-2-methyl-1-phenylbutyl]-2,6-dimethylbenzamide |
| 169 | 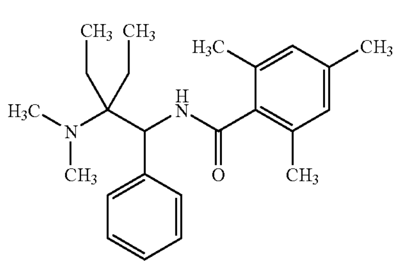 | E | Found 367 (MH+) $C_{24}H_{34}N_2O$ requires 366; 1.87. | (±)-N-[2-(dimethylamino)-2-ethyl-1-phenylbutyl]-2,4,6-trimethylbenzamide |

TABLE 5-continued

| Ex | Structure | Method | Mass spectrum (Electrospray LC/MS), API+ Ret. time (min) | Name |
|---|---|---|---|---|
| 170 | 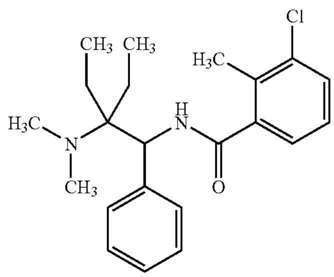 | E | Found 373 (MH+) $C_{22}H_{29}{}^{35}ClN_2O$ requires 372; 1.85. | (±)-3-chloro-N-[2-(dimethylamino)-2-ethyl-1-phenylbutyl]-2-methylbenzamide |
| 171 | 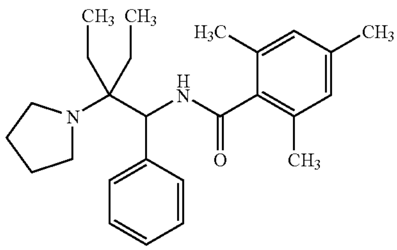 | E | Found 393 (MH+) $C_{26}H_{36}N_2O$ requires 392; 2.02. | (±)-N-[2-ethyl-1-phenyl-2-(1-pyrrolidinyl)butyl]-2,4,6-trimethylbenzamide |
| 172 | 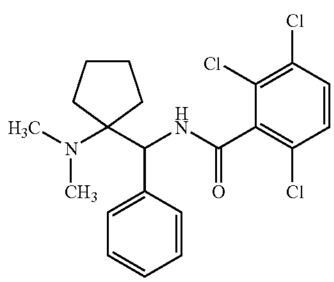 | E | Found 425 (MH+) $C_{21}H_{23}{}^{35}Cl_3N_2O$ requires 424; 2.25. | (±)-2,3,6-trichloro-N-[[1-(dimethylamino)cyclopentyl](phenyl)methyl]benzamide |
| 173 | 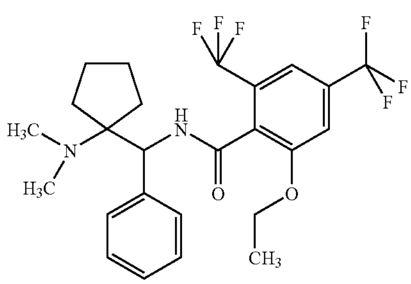 | E | Found 503 (MH+) $C_{25}H_{28}F_6N_2O_2$ requires 502; 2.18. | N-[[1-(dimethylamino)cyclopentyl](phenyl)methyl]-2-(ethyloxy)-4,6-bis(trifluoromethyl)benzamide chiral |
| 174 | 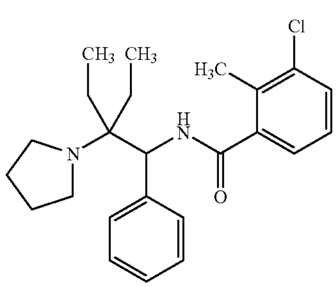 | E | Found 399 (MH+) $C_{24}H_{31}{}^{35}ClN_2O$ requires 398; 2.12. | (±)-3-chloro-N-[2-ethyl-1-phenyl-2-(1-pyrrolidinyl)butyl]-2-methylbenzamide |

TABLE 5-continued

| Ex | Structure | Method | Mass spectrum (Electrospray LC/MS), API+ Ret. time (min) | Name |
|---|---|---|---|---|
| 175 | 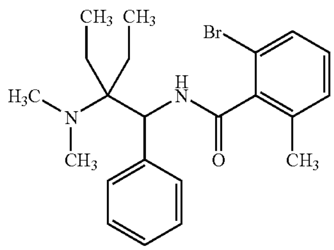 | E | Found 417 (MH+) C$_{22}$H$_{29}$$^{79}$BrN$_2$O requires 416; 1.81. | (±)-2-bromo-N-[2-(dimethylamino)-2-ethyl-1-phenylbutyl]-6-methylbenzamide |
| 176 | 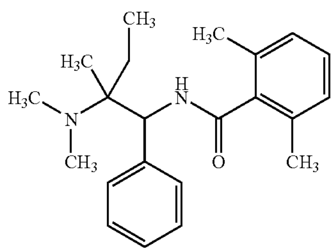 | A | Found 339 (MH+) C$_{22}$H$_{30}$N$_2$O requires 338; 1.63. | (±)-N-[2-(dimethylamino)-2-methyl-1-phenylbutyl]-2,6-dimethylbenzamide |
| 177 | 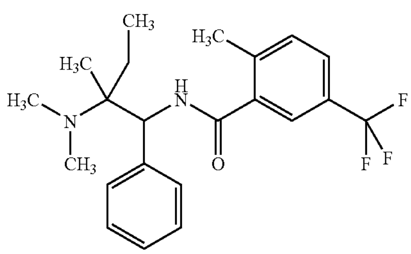 | P | Found 393 (MH+) C$_{22}$H$_{27}$F$_3$N$_2$O requires 392; 1.95 & 2.03. | (±)-N-[2-(dimethylamino)-2-methyl-1-phenylbutyl]-2-methyl-5-(trifluoromethyl)benzamide |
| 178 | 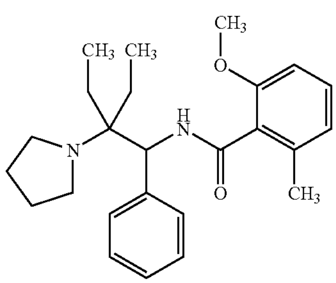 | E | Found 395 (MH+) C$_{25}$H$_{34}$N$_2$O$_2$ requires 394; 1.86. | (±)-N-[2-ethyl-1-phenyl-2-(1-pyrrolidinyl)butyl]-2-methyl-6-(methyloxy)benzamide |
| 179 | 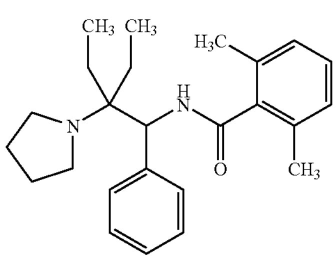 | A | Found 379 (MH+) C$_{25}$H$_{34}$N$_2$O requires 378; 1.89. | (±)-N-[2-ethyl-1-phenyl-2-(1-pyrrolidinyl)butyl]-2,6-dimethylbenzamide |

TABLE 5-continued

| Ex | Structure | Method | Mass spectrum (Electrospray LC/MS), API+ Ret. time (min) | Name |
|---|---|---|---|---|
| 180 | 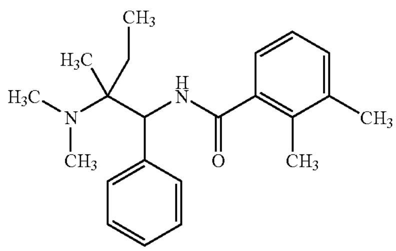 | P | Found 339 (MH+) $C_{22}H_{30}N_2O$ requires 388; 1.90. | N-[2-(dimethylamino)-2-methyl-1-phenylbutyl]-2,3-dimethylbenzamide chiral |
| 181 | 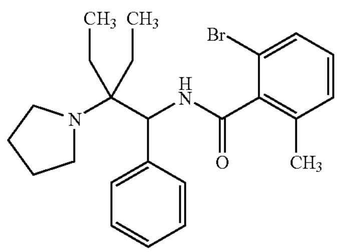 | E | Found 443 (MH+) $C_{24}H_{31}{}^{79}BrN_2O$ requires 442; 2.00. | (±)-2-bromo-N-[2-ethyl-1-phenyl-2-(1-pyrrolidinyl)butyl]-6-methylbenzamide |
| 182 | 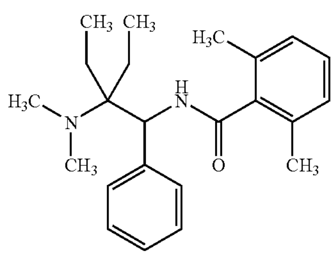 | A | Found 353 (MH+) $C_{23}H_{32}N_2O$ requires 352; 1.82. | (±)-N-[2-(dimethylamino)-2-ethyl-1-phenylbutyl]-2,6-dimethylbenzamide |
| 183 | 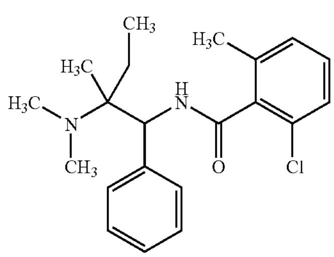 | P | Found 359 (MH+) $C_{21}H_{27}{}^{35}ClN_2O$ requires 358; 1.88 & 1.91. | (±)-2-chloro-N-[2-(dimethylamino)-2-methyl-1-phenylbutyl]-6-methylbenzamide |
| 184 | 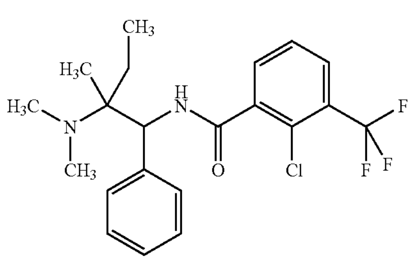 | P | Found 413 (MH+) $C_{21}H_{24}{}^{35}ClF_3N_2O$ requires 412; 2.09 & 2.21. | (±)-2-chloro-N-[2-(dimethylamino)-2-methyl-1-phenylbutyl]-3-(trifluoromethyl)benzamide |
| 185 | 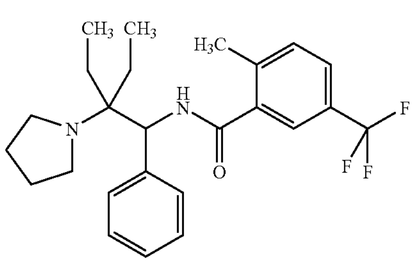 | E | Found 433 (MH+) $C_{25}H_{31}F_3N_2O$ requires 432; 2.20. | (±)-N-[2-ethyl-1-phenyl-2-(1-pyrrolidinyl)butyl]-2-methyl-5-(trifluoromethyl)benzamide |

TABLE 5-continued

| Ex | Structure | Method | Mass spectrum (Electrospray LC/MS), API+ Ret. time (min) | Name |
|---|---|---|---|---|
| 186 | 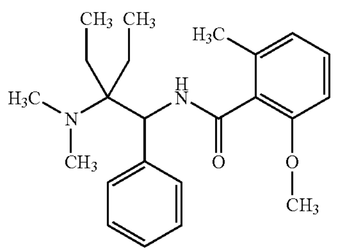 | E | Found 369 (MH+) $C_{23}H_{32}N_2O_2$ requires 368; 1.74. | (±)-N-[2-(dimethylamino)-2-ethyl-1-phenylbutyl]-2-methyl-6-(methyloxy)benzamide |
| 187 | 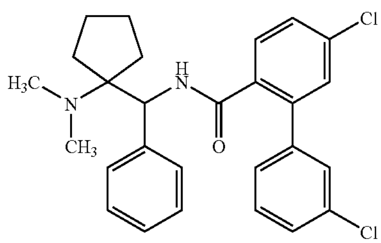 | P | Found 467 (MH+) $C_{27}H_{28}{}^{35}Cl_2N_2O$ requires 466; 2.3 | (±)-3',5-dichloro-N-[[1-(dimethylamino)cyclopentyl](phenyl)methyl]-2-biphenylcarboxamide |
| 188 | 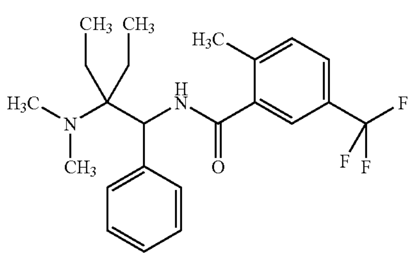 | E | Found 407 (MH+) $C_{23}H_{29}F_3N_2O$ requires 406; 2.08. | (±)-N-[2-(dimethylamino)-2-ethyl-1-phenylbutyl]-2-methyl-5-(trifluoromethyl)benzamide |
| 189 | 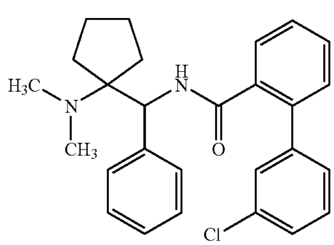 | P | Found 433 (MH+) $C_{27}H_{29}{}^{35}ClN_2O$ requires 432; 2.0 | (±)-3'-chloro-N-[[1-(dimethylamino)cyclopentyl](phenyl)methyl]-2-biphenylcarboxamide |
| 190 | 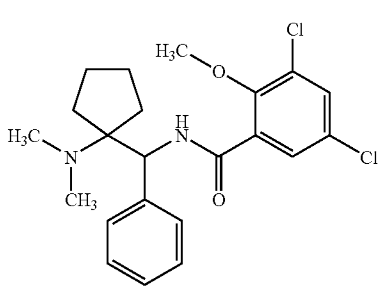 | P | Found 421 (MH+) $C_{22}H_{26}{}^{35}Cl_2N_2O_2$ requires 420; 2.12 | (±)-3,5-dichloro-N-[[1-(dimethylamino)cyclopentyl](phenyl)methyl]-2-(methyloxy)benzamide |

TABLE 5-continued

| Ex | Structure | Method | Mass spectrum (Electrospray LC/MS), API+ Ret. time (min) | Name |
|---|---|---|---|---|
| 191 | 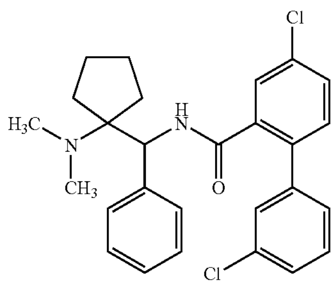 | P | Found 468 (MH+) $C_{27}H_{28}{}^{35}Cl_2N_2O$ requires 467; 2.3 | (±)-3',4-dichloro-N-[[1-(dimethylamino)cyclopentyl](phenyl)methyl]-2-biphenylcarboxamide |
| 192 | 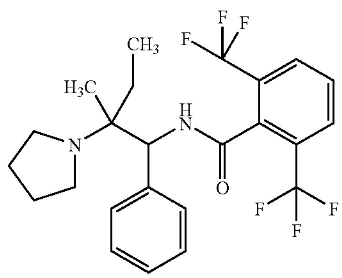 | A | Found 473 (MH+) $C_{24}H_{26}F_6N_2O$ requires 472; 1.97. | (±)-N-[2-methyl-1-phenyl-2-(1-pyrrolidinyl)butyl]-2,6-bis(trifluoromethyl)benzamide |
| 193 | 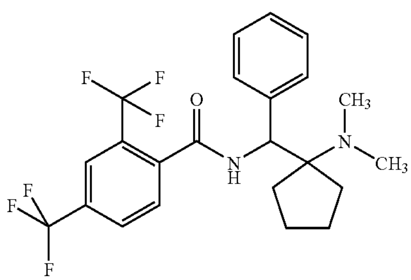 | A | Found 459 (MH+) $C_{23}H_{24}F_6N_2O$ Requires 458; 2.20 | N-[[1-(dimethylamino)cyclopentyl](phenyl)methyl]-2,4-bis(trifluoromethyl)benzamide chiral |
| 194 | 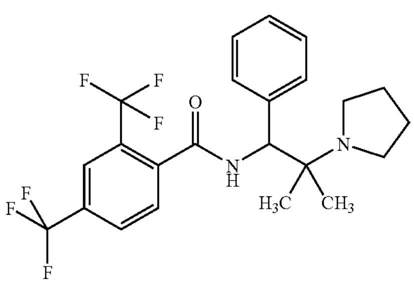 | A | Found 459 (MH+) $C_{23}H_{24}F_6N_2O$ Requires 458; 2.21 | N-[2-methyl-1-phenyl-2-(1-pyrrolidinyl)propyl]-2,4-bis(trifluoromethyl)benzamide chiral |
| 195 | 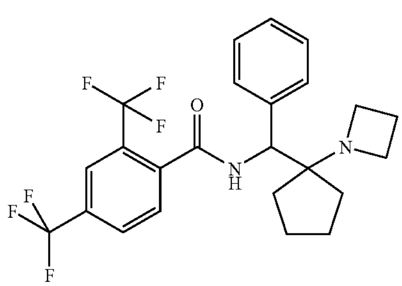 | A | Found 471 (MH+) $C_{24}H_{24}F_6N_2O$ Requires 470; 2.24 | (±)-N-[[1-(1-azetidinyl)cyclopentyl](phenyl)methyl]-2,4-bis(trifluoromethyl)benzamide |

… TABLE 5-continued

| Ex | Structure | Method | Mass spectrum (Electrospray LC/MS), API+ Ret. time (min) | Name |
|---|---|---|---|---|
| 196 | 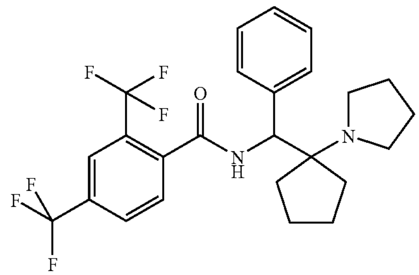 | A | Found 485 (MH+) C25H26F6N2O Requires 484; 2.28 | (±)-N-{phenyl[1-(1-pyrrolidinyl)cyclopentyl]methyl}-2,4-bis(trifluoromethyl)benzamide |
| 197 | 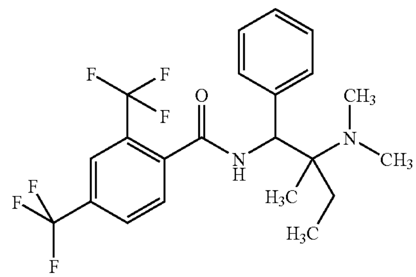 | A | Found 447 (MH+) C22H24F6N2O Requires 446; 2.16 | (±)-N-[2-(dimethylamino)-2-methyl-1-phenylbutyl]-2,4-bis(trifluoromethyl)benzamide |
| 198 | 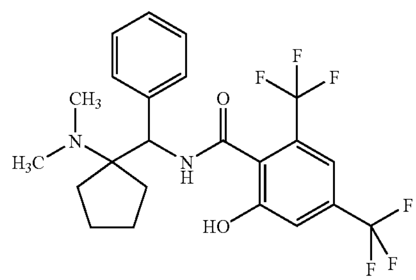 | A | Found 475 (MH+) C23H24F6N2O2 Requires 475; 1.97 | N-[[1-(dimethylamino)cyclopentyl](phenyl)methyl]-2-hydroxy-4,6-bis(trifluoromethyl)benzamide chiral |
| 199 | 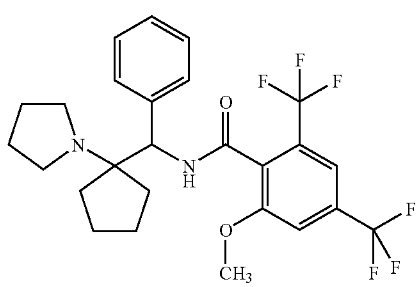 | P | Found 515 (MH+) C26H28F6N2O2 Requires 514; 2.33 | (±)-2-(methyloxy)-N-{phenyl[1-(1-pyrrolidinyl)cyclopentyl]methyl}-4,6-bis(trifluoromethyl)benzamide |
| 200 | 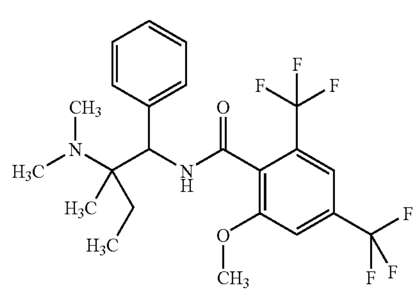 | P | Found 477 (MH+) C23H26F6N2O2 Requires 476; 2.21 | (±)-N-[2-(dimethylamino)-2-methyl-1-phenylbutyl]-2-(methyloxy)-4,6-bis(trifluoromethyl)benzamide |

TABLE 5-continued

| Ex | Structure | Method | Mass spectrum (Electrospray LC/MS), API+ Ret. time (min) | Name |
|---|---|---|---|---|
| 201 | 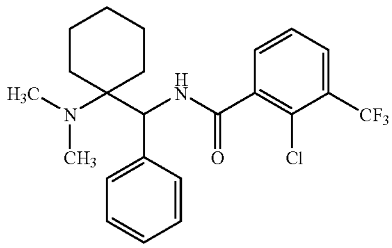 | P | Found 439 (MH+) C₂₃H₂₆³⁵ClF₃N₂O requires 438; 2.16. | (±)-2-chloro-N-[[1-(dimethylamino)cyclohexyl](phenyl)methyl]-3-(trifluoromethyl)benzamide |
| 202 | 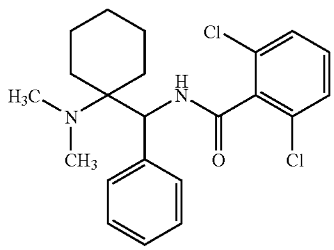 | P | Found 405 (MH+) C₂₂H₂₆³⁵Cl₂N₂O requires 404; 1.90. | (±)-2,6-dichloro-N-[[1-(dimethylamino)cyclohexyl](phenyl)methyl]benzamide |
| 203 | 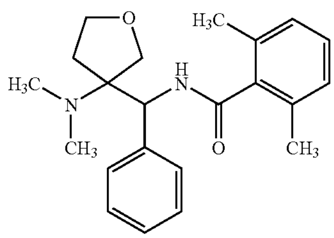 | P | Found 353 (MH+) C₂₂H₂₈N₂O₂ requires 352; 1.70 and 1.72. | (±)-N-[[3-(dimethylamino)tetrahydro-3-furanyl](phenyl)methyl]-2,6-dimethylbenzamide |
| 204 | 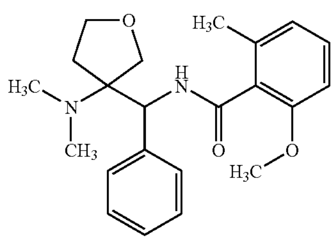 | P | Found 369 (MH+) C₂₂H₂₈N₂O₃ requires 368; 1.75 and 1.77. | (±)-N-[[3-(dimethylamino)tetrahydro-3-furanyl](phenyl)methyl]-2-methyl-6-(methyloxy)benzamide |
| 205 | 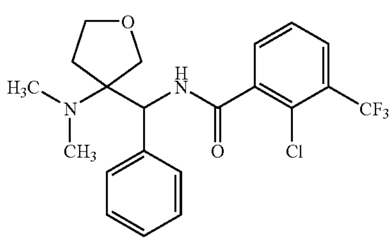 | P | Found 427 (MH+) C₂₁H₂₂³⁵ClF₃N₂O₂ requires 426; 1.94 and 1.96. | (±)-2-chloro-N-[[3-(dimethylamino)tetrahydro-3-furanyl](phenyl)methyl]-3-(trifluoromethyl)benzamide |
| 206 | 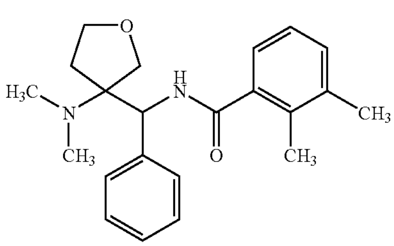 | P | Found 353 (MH+) C₂₂H₂₈N₂O₂ requires 352; 1.74 and 1.76. | (±)-N-[[3-(dimethylamino)tetrahydro-3-furanyl](phenyl)methyl]-2,3-dimethylbenzamide |

TABLE 5-continued

| Ex | Structure | Method | Mass spectrum (Electrospray LC/MS), API+ Ret. time (min) | Name |
|---|---|---|---|---|
| 207 | 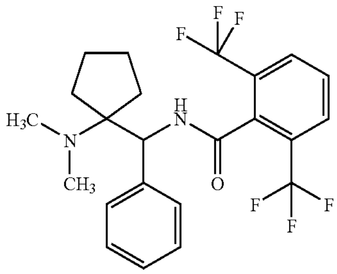 | A | Found 459 (MH+) C₂₃H₂₄F₆N₂O requires 458; 1.97. | N-[[1-(dimethylamino)cyclopentyl] (phenyl)methyl]-2,6-bis(trifluoromethyl)benzamide chiral |
| 208 | 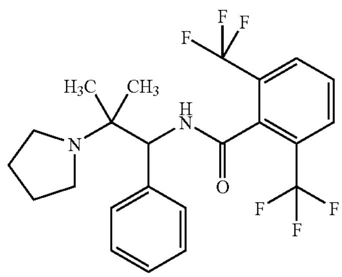 | A | Found 459 (MH+) C₂₃H₂₄F₆N₂O requires 458; 1.92. | N-[2-methyl-1-phenyl-2-(1-pyrrolidinyl)propyl]-2,6-bis(trifluoromethyl)benzamide chiral |
| 209 | 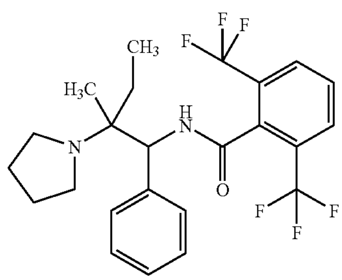 | A | Found 473 (MH+) C₂₄H₂₆F₆N₂O requires 472; 2.05 & 2.09. | (±)-N-[2-methyl-1-phenyl-2-(1-pyrrolidinyl)butyl]-2,6-bis(trifluoromethyl)benzamide |
| 210 | 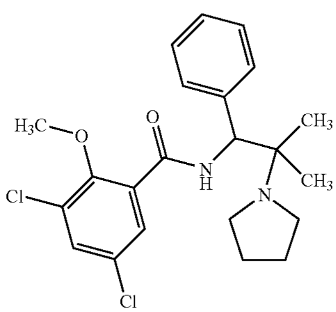 | PE | Found 421 (MH+) C₂₂H₂₆³⁵Cl₂N₂O₂ requires 420; 2.53*. | (±)-3,5-dichloro-2-(methyloxy)-N-[2-methyl-1-phenyl-2-(1-pyrrolidinyl)propyl]benzamide |
| 211 | 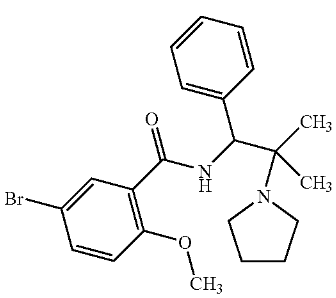 | PE | Found 431 (MH+) C₂₂H₂₇⁷⁹BrN₂O₂ requires 430; 2.57*. | (±)-5-bromo-2-(methyloxy)-N-[2-methyl-1-phenyl-2-(1-pyrrolidinyl)propyl]benzamide |

TABLE 5-continued

| Ex | Structure | Method | Mass spectrum (Electrospray LC/MS), API+ Ret. time (min) | Name |
| --- | --- | --- | --- | --- |
| 212 | 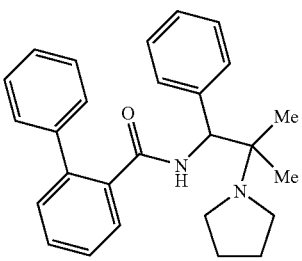 | PE | Found 399 (MH+) $C_{27}H_{30}N_2O$ requires 398; 2.47*. | (±)-N-[2-methyl-1-phenyl-2-(1-pyrrolidinyl)propyl]-2-biphenylcarboxamide |
| 213 | 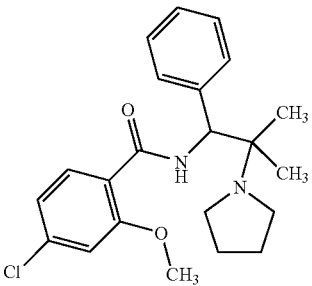 | PE | Found 387 (MH+) $C_{22}H_{27}{}^{35}ClN_2O_2$ requires 386; 2.49*. | (±)-4-chloro-2-(methyloxy)-N-[2-methyl-1-phenyl-2-(1-pyrrolidinyl)propyl]benzamide |
| 214 | 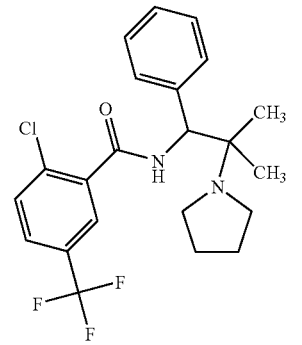 | PE | Found 425 (MH+) $C_{22}H_{24}{}^{35}ClF_3N_2O$ requires 424; 2.45*. | (±)-2-chloro-N-[2-methyl-1-phenyl-2-(1-pyrrolidinyl)propyl]-5-(trifluoromethyl)benzamide |
| 215 | 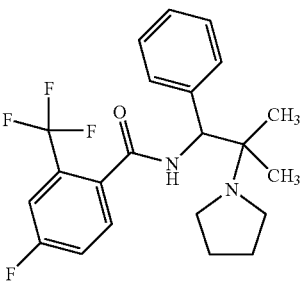 | PE | Found 409 (MH+) $C_{22}H_{24}F_4N_2O$ requires 408; 2.39*. | (±)-4-fluoro-N-[2-methyl-1-phenyl-2-(1-pyrrolidinyl)propyl]-2-(trifluoromethyl)benzamide |
| 216 | 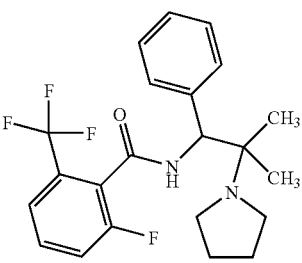 | PE | Found 409 (MH+) $C_{22}H_{24}F_4N_2O$ requires 408; 2.56*. | (±)-2-fluoro-N-[2-methyl-1-phenyl-2-(1-pyrrolidinyl)propyl]-6-(trifluoromethyl)benzamide |

TABLE 5-continued

| Ex | Structure | Method | Mass spectrum (Electrospray LC/MS), API+ Ret. time (min) | Name |
|---|---|---|---|---|
| 217 | 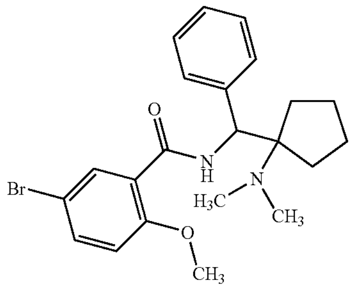 | PE | Found 431 (MH+) C$_{22}$H$_{27}$$^{79}$BrN$_2$O$_2$ requires 430; 2.54*. | 5-bromo-N-[[1-(dimethylamino)cyclopentyl](phenyl)methyl]-2-(methyloxy)benzamide chiral |
| 218 | 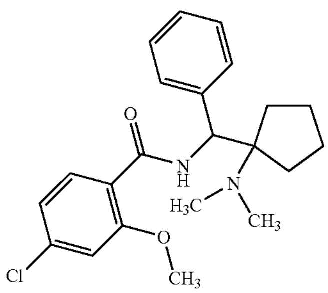 | PE | Found 387 (MH+) C$_{22}$H$_{27}$$^{35}$ClN$_2$O$_2$ requires 386; 2.54*. | 4-chloro-N-[[1-(dimethylamino)cyclopentyl](phenyl)methyl]-2-(methyloxy)benzamide chiral |
| 219 | 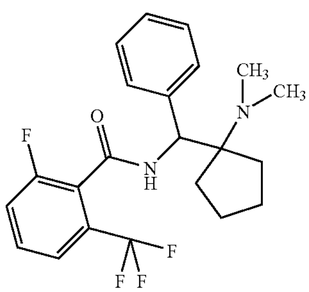 | PE | Found 409 (MH+) C$_{22}$H$_{24}$F$_4$N$_2$O requires 408; 2.47*. | N-[[1-(dimethylamino)cyclopentyl](phenyl)methyl]-2-fluoro-6-(trifluoromethyl)benzamide chiral |
| 220 | 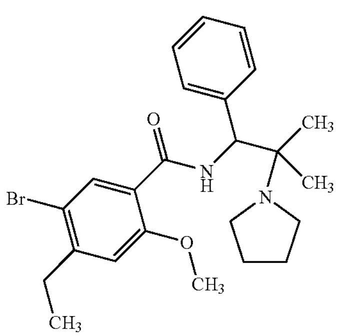 | PE | Found 459 (MH+) C$_{24}$H$_{31}$$^{79}$BrN$_2$O$_2$ requires 458; 2.81*. | (±)-5-bromo-4-ethyl-2-(methyloxy)-N-[2-methyl-1-phenyl-2-(1-pyrrolidinyl)propyl]benzamide |

TABLE 5-continued

| Ex | Structure | Method | Mass spectrum (Electrospray LC/MS), API⁺ Ret. time (min) | Name |
|---|---|---|---|---|
| 221 | 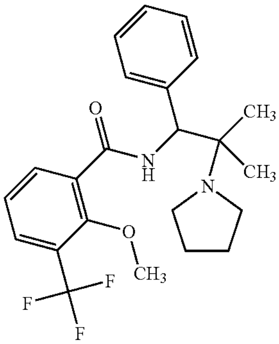 | PE | Found 421 (MH⁺) $C_{23}H_{27}F_3N_2O_2$ requires 420; 2.63*. | (±)-2-(methyloxy)-N-[2-methyl-1-phenyl-2-(1-pyrrolidinyl)propyl]-3-(trifluoromethyl)benzamide |
| 222 | 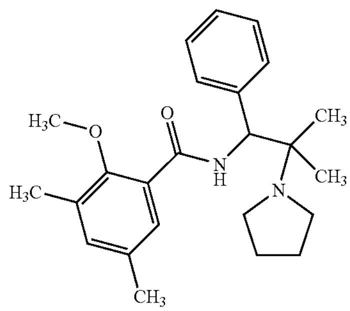 | PE | Found 381 (MH⁺) $C_{24}H_{32}N_2O_2$ requires 380; 2.52*. | (±)-3,5-dimethyl-2-(methyloxy)-N-[2-methyl-1-phenyl-2-(1-pyrrolidinyl)propyl]benzamide |
| 223 | 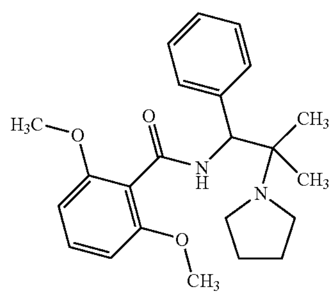 | PE | Found 383 (MH⁺) $C_{23}H_{30}N_2O_3$ requires 382; 2.77*. | (±)-2,6-bis(methyloxy)-N-[2-methyl-1-phenyl-2-(1-pyrrolidinyl)propyl]benzamide |
| 224 | 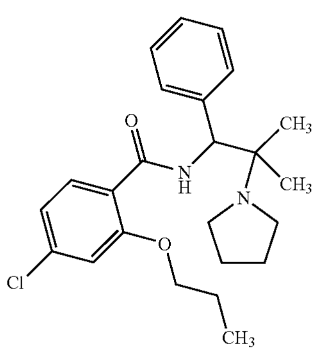 | PE | Found 415 (MH⁺) $C_{24}H_{31}{}^{35}ClN_2O_2$ requires 414; 3.05*. | (±)-4-chloro-N-[2-methyl-1-phenyl-2-(1-pyrrolidinyl)propyl]-2-(propyloxy)benzamide |

TABLE 5-continued

| Ex | Structure | Method | Mass spectrum (Electrospray LC/MS), API+ Ret. time (min) | Name |
|---|---|---|---|---|
| 225 | 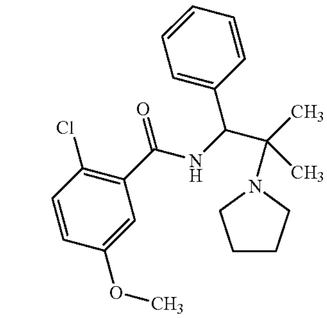 | PE | Found 387 (MH+) $C_{22}H_{27}{}^{35}ClN_2O_2$ requires 386; 2.53*. | (±)-2-chloro-5-(methyloxy)-N-[2-methyl-1-phenyl-2-(1-pyrrolidinyl)propyl]benzamide |
| 226 | 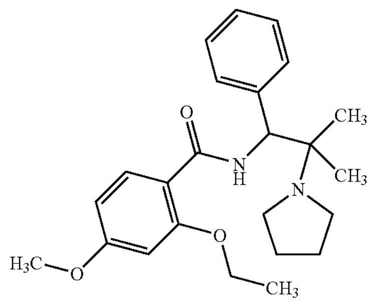 | PE | Found 397 (MH+) $C_{24}H_{32}N_2O_3$ requires 396; 2.58*. | (±)-2-(ethyloxy)-4-(methyloxy)-N-[2-methyl-1-phenyl-2-(1-pyrrolidinyl)propyl]benzamide |
| 227 | 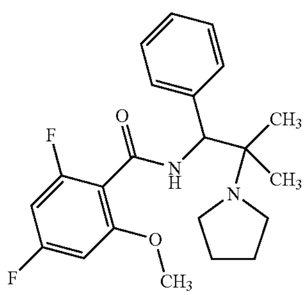 | PE | Found 389 (MH+) $C_{22}H_{26}F_2N_2O_2$ requires 388; 2.47*. | (±)-2,4-difluoro-6-(methyloxy)-N-[2-methyl-1-phenyl-2-(1-pyrrolidinyl)propyl]benzamide |
| 228 | 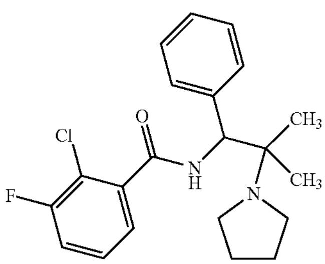 | PE | Found 375 (MH+) $C_{21}H_{24}{}^{35}ClFN_2O$ requires 374; 2.86*. | (±)-2-chloro-3-fluoro-N-[2-methyl-1-phenyl-2-(1-pyrrolidinyl)propyl]benzamide |
| 229 | 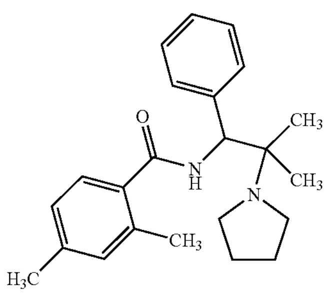 | PE | Found 351 (MH+) $C_{23}H_{30}N_2O$ requires 350; 2.84*. | (±)-2,4-dimethyl-N-[2-methyl-1-phenyl-2-(1-pyrrolidinyl)propyl]benzamide |

TABLE 5-continued

| Ex | Structure | Method | Mass spectrum (Electrospray LC/MS), API+ Ret. time (min) | Name |
|---|---|---|---|---|
| 230 | 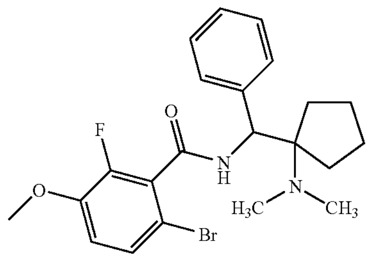 | PE | Found 449 (MH+) C$_{22}$H$_{26}$$^{79}$BrFN$_2$O$_2$ requires 448; 2.45*. | 6-bromo-N-[[1-(dimethylamino)cyclopentyl](phenyl)methyl]-2-fluoro-3-(methyloxy)benzamide chiral |
| 231 | 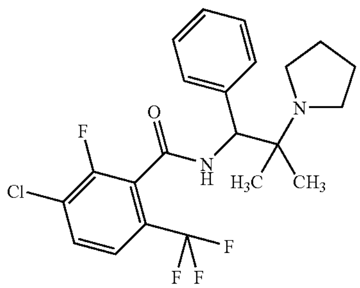 | PE | Found 443 (MH+) C$_{22}$H$_{23}$$^{35}$ClF$_4$N$_2$O requires 442; 2.94*. | (±)-3-chloro-2-fluoro-N-[2-methyl-1-phenyl-2-(1-pyrrolidinyl)propyl]-6-(trifluoromethyl)benzamide |
| 232 | 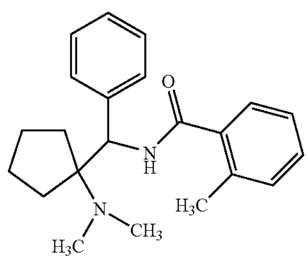 | P | Found 337 (MH+) C$_{22}$H$_{28}$N$_2$O requires 336; 1.86. | (±)-N-[[1-(dimethylamino)cyclopentyl](phenyl)methyl]-2-methylbenzamide |
| 233 | 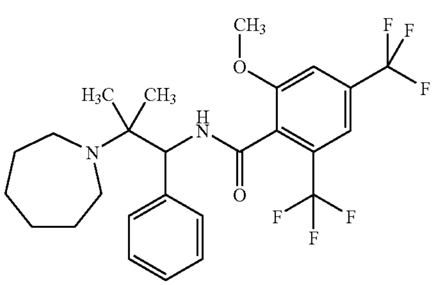 | A | Found 517 (MH+) C$_{26}$H$_{30}$F$_6$N$_2$O$_2$ requires 516; 2.32. | (±)-N-[2-(hexahydro-1H-azepin-1-yl)-2-methyl-1-phenylpropyl]-2-(methyloxy)-4,6-bis(trifluoromethyl)benzamide |
| 234 | 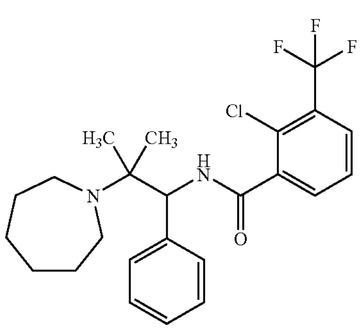 | A | Found 453 (MH+) C$_{24}$H$_{28}$$^{35}$ClF$_3$N$_2$O requires 452; 2.21. | (±)-2-chloro-N-[2-(hexahydro-1H-azepin-1-yl)-2-methyl-1-phenylpropyl]-3-(trifluoromethyl)benzamide |

TABLE 5-continued

| Ex | Structure | Method | Mass spectrum (Electrospray LC/MS), API+ Ret. time (min) | Name |
|---|---|---|---|---|
| 235 | 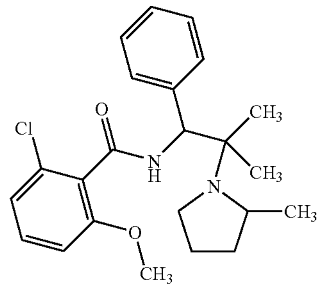 | PE | Found 401 (MH+) $C_{23}H_{29}^{35}ClN_2O_2$ requires 400; 2.48*. | (±)-2-chloro-N-[2-methyl-2-(2-methyl-1-pyrrolidinyl)-1-phenylpropyl]-6-(methyloxy)benzamide |
| 236 | 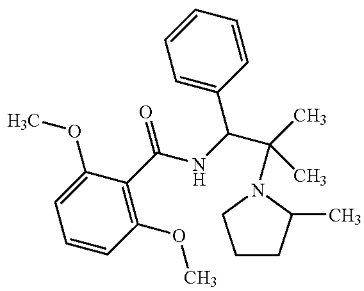 | PE | Found 397 (MH+) $C_{24}H_{32}N_2O_3$ requires 396; 2.79*. | (±)-N-[2-methyl-2-(2-methyl-1-pyrrolidinyl)-1-phenylpropyl]-2,6-bis(methyloxy)benzamide |
| 237 | 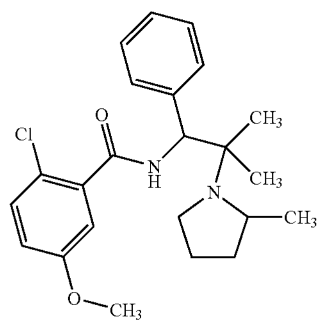 | PE | Found 401 (MH+) $C_{23}H_{29}^{35}ClN_2O_2$ requires 400; 2.53*. | (±)-2-chloro-N-[2-methyl-2-(2-methyl-1-pyrrolidinyl)-1-phenylpropyl]-5-(methyloxy)benzamide |
| 238 | 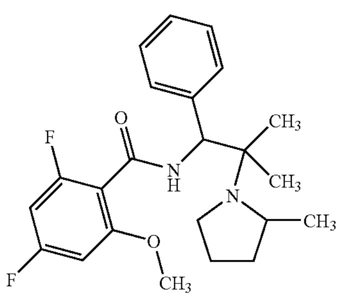 | PE | Found 403 (MH+) $C_{23}H_{28}F_2N_2O_2$ requires 402; 2.52*. | (±)-2,4-difluoro-N-[2-methyl-2-(2-methyl-1-pyrrolidinyl)-1-phenylpropyl]-6-(methyloxy)benzamide |
| 239 | 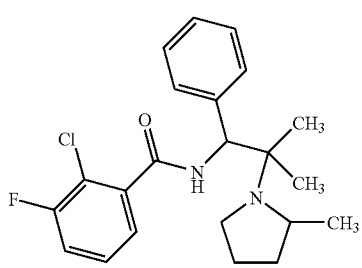 | PE | Found 389 (MH+) $C_{22}H_{26}^{35}ClFN_2O$ requires 388; 2.89*. | (±)-2-chloro-3-fluoro-N-[2-methyl-2-(2-methyl-1-pyrrolidinyl)-1-phenylpropyl]benzamide |

TABLE 5-continued

| Ex | Structure | Method | Mass spectrum (Electrospray LC/MS), API+ Ret. time (min) | Name |
|---|---|---|---|---|
| 240 | 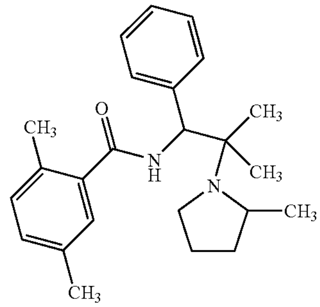 | PE | Found 365 (MH+) $C_{24}H_{32}N_2O$ requires 364; 2.66*. | (±)-2,5-dimethyl-N-[2-methyl-2-(2-methyl-1-pyrrolidinyl)-1-phenylpropyl]benzamide |
| 241 | 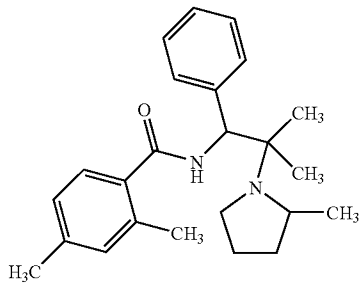 | PE | Found 365 (MH+) $C_{24}H_{32}N_2O$ requires 364; 2.94*. | (±)-2,4-dimethyl-N-[2-methyl-2-(2-methyl-1-pyrrolidinyl)-1-phenylpropyl]benzamide |
| 242 | 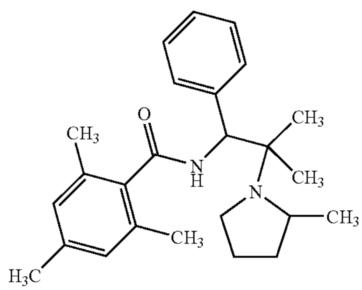 | PE | Found 379 (MH+) $C_{25}H_{34}N_2O$ requires 378; 2.5*. | (±)-2,4,6-trimethyl-N-[2-methyl-2-(2-methyl-1-pyrrolidinyl)-1-phenylpropyl]benzamide |
| 243 | 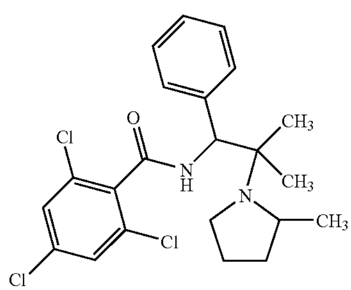 | PE | Found 439 (MH+) $C_{22}H_{25}{}^{35}Cl_3N_2O$ requires 438; 2.91*. | (±)-2,4,6-trichloro-N-[2-methyl-2-(2-methyl-1-pyrrolidinyl)-1-phenylpropyl]benzamide |
| 244 | 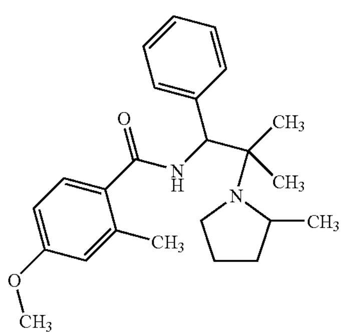 | PE | Found 381 (MH+) $C_{24}H_{32}N_2O_2$ requires 380; 2.84*. | (±)-2-methyl-N-[2-methyl-2-(2-methyl-1-pyrrolidinyl)-1-phenylpropyl]-4-(methyloxy)benzamide |

TABLE 5-continued

| Ex | Structure | Method | Mass spectrum (Electrospray LC/MS), API+ Ret. time (min) | Name |
|---|---|---|---|---|
| 245 | 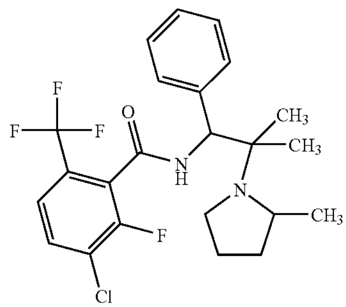 | PE | Found 457 (MH+) $C_{23}H_{25}{}^{35}ClF_4N_2O$ requires 456; 2.97*. | (±)-3-chloro-2-fluoro-N-[2-methyl-2-(2-methyl-1-pyrrolidinyl)-1-phenylpropyl]-6-(trifluoromethyl)benzamide |
| 246 | 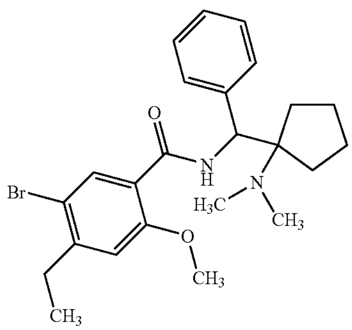 | PE | Found 459 (MH+) $C_{24}H_{31}{}^{79}BrN_2O_2$ requires 458; 2.84*. | 5-bromo-N-[[1-(dimethylamino)cyclopentyl](phenyl)methyl]-4-ethyl-2-(methyloxy)benzamide chiral |
| 247 | 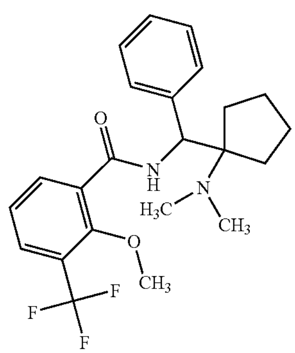 | PE | Found 421 (MH+) $C_{23}H_{27}F_3N_2O_2$ requires 420; 2.67*. | N-[[1-(dimethylamino)cyclopentyl](phenyl)methyl]-2-(methyloxy)-3-(trifluoromethyl)benzamide chiral |
| 248 | 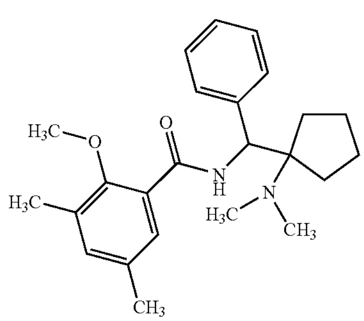 | PE | Found 381 (MH+) $C_{24}H_{32}N_2O_2$ requires 380; 2.54*. | N-[[1-(dimethylamino)cyclopentyl](phenyl)methyl]-3,5-dimethyl-2-(methyloxy)benzamide chiral |

TABLE 5-continued

| Ex | Structure | Method | Mass spectrum (Electrospray LC/MS), API+ Ret. time (min) | Name |
|---|---|---|---|---|
| 249 | 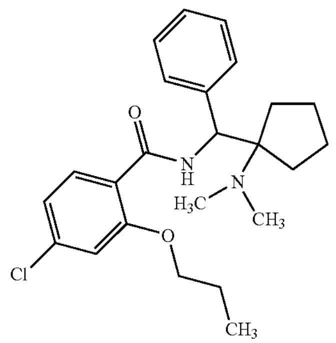 | PE | Found 415 (MH+) $C_{24}H_{31}{}^{35}ClN_2O_2$ requires 414; 3.21*. | 4-chloro-N-[[1-(dimethylamino)cyclopentyl](phenyl)methyl]-2-(propyloxy)benzamide chiral |
| 250 | 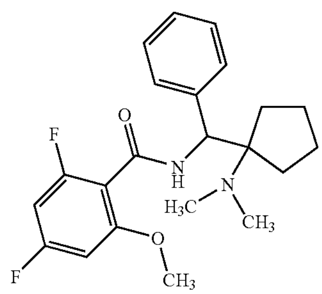 | PE | Found 389 (MH+) $C_{22}H_{26}F_2N_2O_2$ requires 388; 2.51*. | N-[[1-(dimethylamino)cyclopentyl](phenyl)methyl]-2,4-difluoro-6-(methyloxy)benzamide chiral |
| 251 | 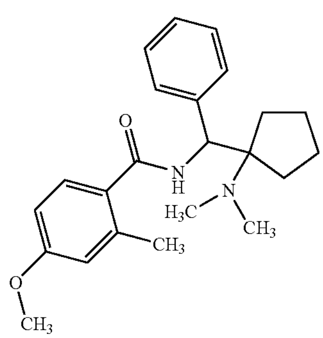 | PE | Found 367 (MH+) $C_{23}H_{30}N_2O_2$ requires 366; 2.98*. | N-[[1-(dimethylamino)cyclopentyl](phenyl)methyl]-2-methyl-4-(methyloxy)benzamide chiral |
| 252 | 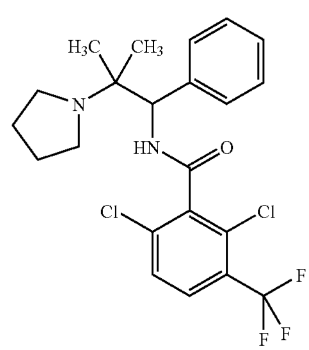 | P# | Found 459 (MH+) $C_{22}H_{23}{}^{35}Cl_2F_3N_2O$ requires 458; 2.07 | 2,6-dichloro-N-[2-methyl-1-phenyl-2-(1-pyrrolidinyl)propyl]-3-(trifluoromethyl)benzamide chiral |

TABLE 5-continued

| Ex | Structure | Method | Mass spectrum (Electrospray LC/MS), API+ Ret. time (min) | Name |
|----|-----------|--------|-----------|------|
| 253 | 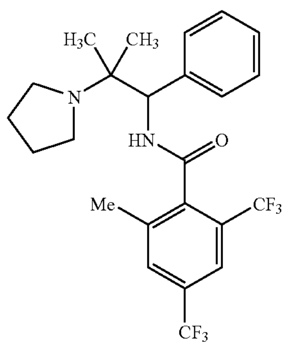 | A | Found 473 (MH+) C24H26F6N2O requires 472; 2.22. | 2-methyl-N-[2-methyl-1-phenyl-2-(1-pyrrolidinyl)propyl]-4,6-bis-(trifluoromethyl)benzamide chiral |

EXAMPLE 253

2-Methyl-N-[2-methyl-1-phenyl-2-(1-pyrrolidinyl)propyl]-4,6-bis(trifluoromethyl)benzamide Chiral—Alternative Method

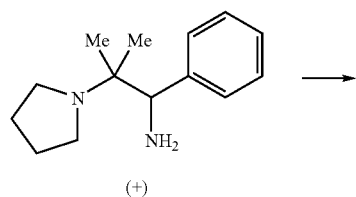

A mixture of 2-methyl-4,6-bis(trifluoromethyl)benzoyl chloride and methyl 2,4-bis(trifluoromethyl)benzoate (approximately 0.5 mmol) prepared as described in D53 was dissolved in dry DCM (3 ml) and treated with (+)-[2-methyl-1-phenyl-2-(1-pyrrolidinyl)propyl]amine D6 (109 mg, 0.50 mmol) and triethylamine (140 ul, 1.00 mmol) and left overnight at room temperature. The volatile components were removed under reduced pressure and the residue chromatographed on silica gel. Elution with 0-80% ethyl acetate in pentane gave the title product as an gum (127 mg, ca.54%). $^1$H NMR (CDCl$_3$) δ: 0.90 (3H, s), 1.01 (3H, s), 1.70 (4H, overlapping m), 2.47 (3H, s), 2.63 (4H, overlapping m), 4.84 (1H, d, J=2.8 Hz), 7.16 (1H, br s), 7.26-7.38 (5H, overlapping m) 7.67 (1H, s), 7.77 (1H, s). Mass Spectrum (Electrospray LC/MS): Found 473 (MH+) C24H26F6N2O requires 472. Ret time 2.24 min.

This was converted to the hydrochloride salt (white solid, 140 mg) by addition of excess 1M HCl in ether to a chloroform solution of the amine and removal of the solvent under reduced pressure.

EXAMPLE 254

4-Chloro-N-[[1-(dimethylamino)cyclopentyl](phenyl)methyl]-2-methylbenzamide Chiral

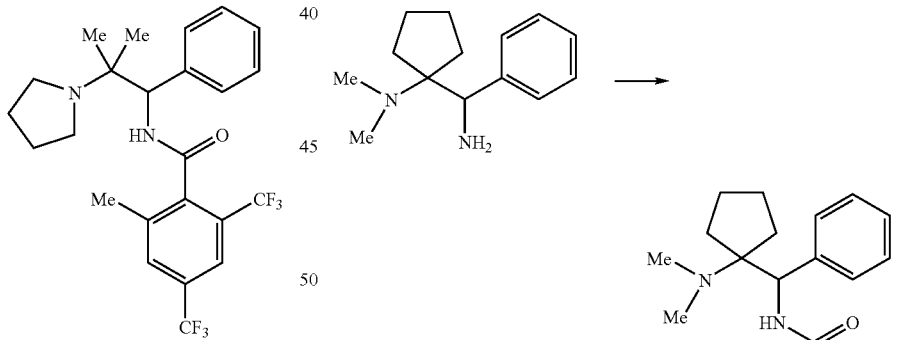

A mixture of {1-[amino(phenyl)methyl]cyclopentyl}dimethylamine D3 enantiomer 2 (80 mg, 0.37 mmol), 4-chloro-2-methylbenzoic acid (68 mg; 0.40 mmol), HOBt (61 mg; 0.40 mmol) and PS-DCC (310 mg of 1.3 mmol/g loading, 0.40 mmol) in DCM (4 ml) was shaken overnight. Saturated aqueous sodium bicarbonate was added and the mixture separated with a phase-sep cartridge and the organics applied directly to SCX resin. Elution with DCM, methanol and then 1M ammonia in methanol, followed by chromatography eluting with 12-100% ethyl acetate-pentane (SP4 Biotage) afforded the title product (64 mg; 43%). $^1$H NMR (CDCl$_3$) δ: 0.9-1.0 (1H, m), 1.25-1.40 (1H, m), 1.4-1.6 (2H, m), 1.6-1.75 (2H, m), 1.8-1.9 (2H, m), 2.22 (6H, s), 2.41 (3H, s), 5.09 (1H, d, J=5 Hz), 7.07 (1H, d, J=5 Hz), 7.2-7.4 (8H, m). Mass Spectrum (Electrospray LC/MS): Found 371 (MH$^+$). $C_{22}H_{27}{}^{35}ClN_2O$ requires 370. Ret. time 2.26 min. The title product was converted to the corresponding hydrochloride salt.

EXAMPLE 255

2,4-Dichloro-N-[[1-(dimethylamino)cyclopentyl](phenyl)methyl]-6-(methyloxy)benzamide Chiral

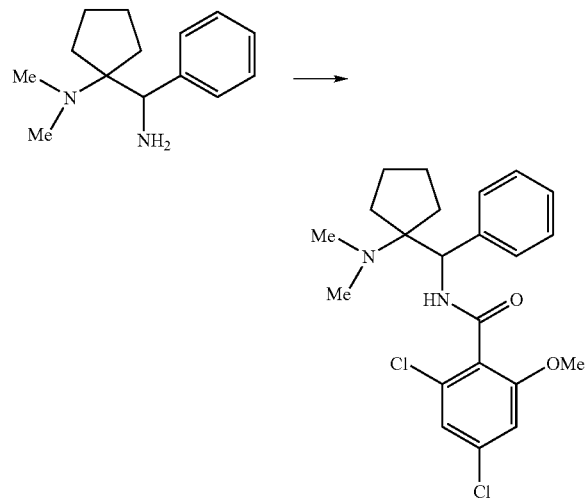

A mixture of {1-[amino(phenyl)methyl]cyclopentyl}dimethylamine D3 enantiomer 2 (80 mg, 0.37 mmol), 2,4-dichloro-6-(methyloxy)benzoic acid (88 mg; 0.40 mmol), HOBt (61 mg; 0.40 mmol) and PS-DCC (310 mg of 1.3 mmol/g loading, 0.40 mmol) in DCM (4 ml) was shaken overnight. Saturated aqueous sodium bicarbonate was added and the mixture separated with a phase-sep cartridge and the organics applied directly to SCX resin. Elution with DCM, methanol and then 1M ammonia in methanol, followed by chromatography eluting with 12-100% ethyl acetate-pentane (SP4 Biotage) afforded the title product (133 mg; 79%). $^1$H NMR (CDCl$_3$) δ: 0.95-1.10 (1H, m), 1.25-1.35 (1H, m), 1.40-1.60 (2H, m), 1.60-1.75 (2H, m), 1.80-1.90 (2H, m), 2.22 (6H, s), 3.82 (3H, s), 5.08 (1H, d, J=5 Hz), 6.82 (1H, d, J=2 Hz), 7.02 (1H, d, J=2 Hz), 7.07 (1H, m), 7.22-7.33 (3H, m), 7.44-7.46 (2H, m). Mass Spectrum (Electrospray LC/MS): Found 421 (MH$^+$). $C_{22}H_{26}{}^{35}Cl_2N_2O_2$ requires 420. Ret. time 2.34 min. The title product was converted to the corresponding hydrochloride salt. 2,4-Dichloro-6-(methyloxy)benzoic acid can be prepared as described by G. E. Stokker, A. W. Alberts, P. S. Anderson, E. J. Cragoe Jr., A. A. Deana, J. L. Gilfillan, J. Hirshfield, W. J. Holtz, W. F. Hoffman, J. W. Huff, T. J. Lee, F. C. Novello, J. D. Prugh, C. S. Rooney, R. L. Smith, A. K. Willard J Med Chem, 1986, 29(2), 170.

EXAMPLE 256

2,4-Dichloro-6-(methyloxy)-N-[2-methyl-1-phenyl-2-(1-pyrrolidinyl)propyl]benzamide Chiral

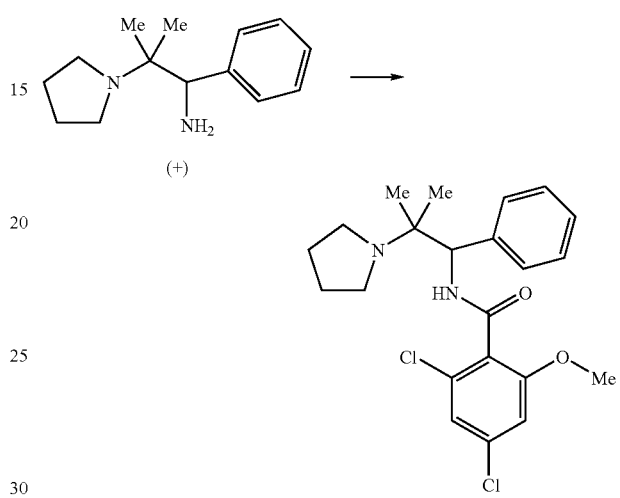

To a solution of (+)-[2-methyl-1-phenyl-2-(1-pyrrolidinyl)propyl]amine D6 (0.10 g; 0.459 mmol) and triethylamine (0.15 ml; 1 mmol) in DCM (3 ml) was added a solution of 2,4-dichloro-6-methyloxybenzoyl chloride (0.13 g; 0.540 mmol) in DCM (2 ml). After 1 h. saturated aqueous sodium hydrogen carbonate (8 ml) was added and the mixture shaken for 2 minutes. The organic layer was passed through a phase separation cartridge and the solvent removed under reduced pressure. The residue was dissolved in the minimum of DCM and applied to a 10 g silica gel column. Elution with 0-100% ethyl acetate in pentane gradient and removal of solvent under reduced pressure afforded the title compound as a colourless gum (0.14 g: 72%). $^1$H NMR (CDCl$_3$) δ: 0.91 (3H, s), 0.96 (3H, s), 1.60-1.80 (4H, m), 2.55-2.75 (4H, m), 3.82 (3H, s), 4.76 (1H, d, J=2.4 Hz), 6.81 (1H, d, J=1.6 Hz), 7.02 (1H, d, J=1.6 Hz), 7.20-7.50 (6H, m). Mass spectrum (Electrospray LC/MS). Found 421 (MH$^+$). $C_{22}H_{26}{}^{35}Cl_2N_2O_2$ requires 420. Ret. Time: 1.97 min.

EXAMPLES 257

(±)-2-(Methyloxy)-N-[2-methyl-1-phenyl-2-(1-pyrrolidinyl)butyl]-4,6-bis(trifluoromethyl)benzamide Diastereoisomer Pair 1 and Diastereoisomer Pair 2

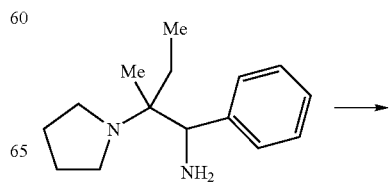

-continued

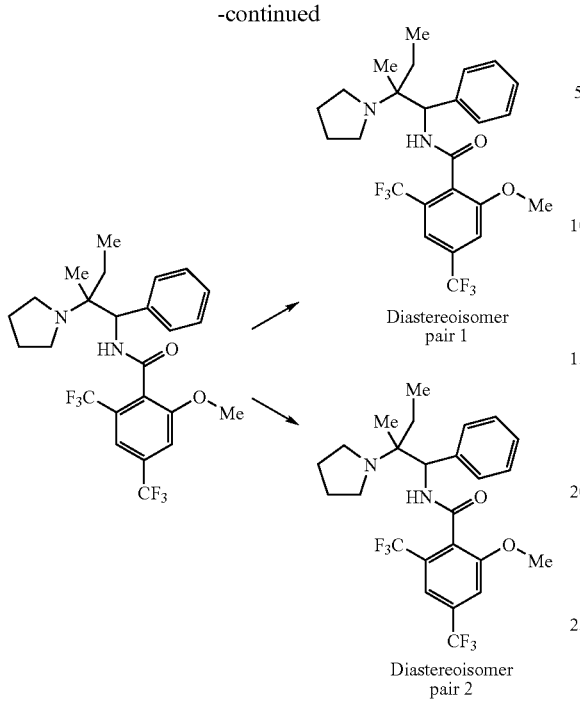

To a stirred solution of (±)-[2-methyl-1-phenyl-2-(1-pyrrolidinyl)butyl]amine D22 (2.32 g; 10 mmol) and triethylamine (2.78 ml; 20 mmol) in DCM (75 ml) at room temperature was added a solution of 2-(methyloxy)-4,6-bis(trifluoromethyl)benzoyl chloride (3.10 g; 10 mmol) in DCM (25 ml) dropwise over 10 minutes. After 20 h. saturated aqueous sodium hydrogen carbonate (100 ml) was added and stirring continued for 0.5 h. The layers were separated and the aqueous layer extracted with DCM (150 ml). The combined organics were dried (Na$_2$SO$_4$), filtered and the solvent removed under reduced pressure to afford a pale orange foam (4.8 g). The sample was dissolved in the minimum of DCM and one half of the solution applied to a 40M silica column. Elution with 2% MeOH in DCM (2.5 L) then 3% MeOH in DCM (2.4 L) afforded the title compound diastereoisomer pair 1 (0.16 g) $^1$H NMR (CDCl$_3$) δ: 0.97 (3H, s), 1.01 (3H, t, J=7.6 Hz), 1.25-1.35 (2H, q, J=8 Hz), 1.55-1.75 (4H, m), 2.55-2.70 (4H, m), 3.93 (3H, s), 4.84 (1H, d, J=0.9 Hz), 7.20-7.45 (7H, m), 7.54 (1H, s). Mass spectrum (Electrospray LC/MS). Found 503 (MH$^+$). C$_{25}$H$_{28}$F$_6$N$_2$O$_2$ requires 502. Ret. Time: 2.27 min.

Further elution with 5% MeOH in DCM afforded the title compound diastereoisomer pair 2 (0.36 g). $^1$H NMR (CDCl$_3$) δ: 0.75-0.85 (3H, t), 1.03 (3H, s), 1.35-1.55 (1H, m), 1.60-1.72 (4H, m), 1.72-1.90 (1H, m), 2.70-2.85 (4H, m), 3.92 (3H, s), 4.83 (1H, d, J=3.6 Hz) 7.20-7.40 (7H, m), 7.53 (1H, s). Mass spectrum (Electrospray LC/MS). Found 503 (MH$^+$). C$_{25}$H$_{28}$F$_6$N$_2$O$_2$ requires 502. Ret. Time: 2.30 min.

EXAMPLE 258

N-[2-Methyl-1-phenyl-2-(1-pyrrolidinyl)propyl]-2-(methylthio)-4,6-bis(trifluoromethyl)benzamide
Chiral

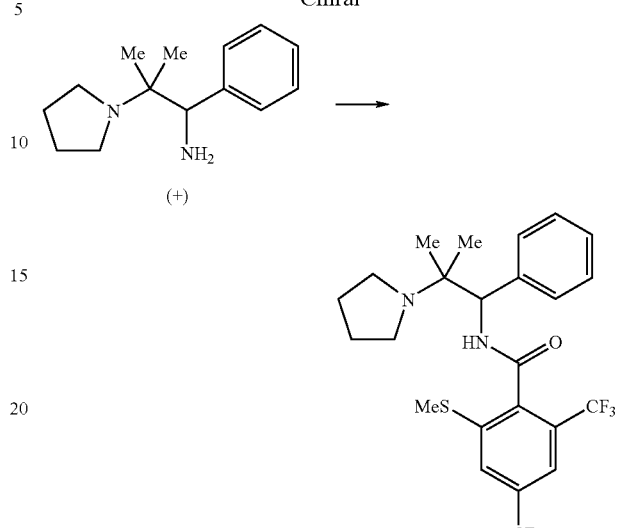

A solution of 2-(methylthio)-4,6-bis(trifluoromethyl)benzoyl chloride D55 (60 mg; 0.19 mmol) in dry DCM (1 ml) was treated with (+)-[2-methyl-1-phenyl-2-(1-pyrrolidinyl)propyl]amine D6 (60 mg, 0.27 mmol) followed by triethylamine (5drops) and left overnight at room temperature. The volatile components were removed under reduced pressure and the residue chromatographed on silica gel. Elution with 0-80% ethyl acetate in pentane gave the title product as an oil (80 mg, 85%). $^1$H NMR (CDCl$_3$) δ: 0.94 (3H, s), 1.00 (3H, s), 1.69 (4H, overlapping m), 2.54 (3H, s), 2.62 (2H, m), 2.72 (2H, m), 4.78 (1H, s), 7.25-7.45 (6H, overlapping m), 7.68 (1H, s), 7.72 (1H, s). Mass Spectrum (Electrospray LC/MS): Found 505 (MH$^+$) C$_{24}$H$_{26}$F$_6$N$_2$OS requires 504. Ret time 2.24 min.

The title product was converted to the hydrochloride salt (85 mg) by addition of excess 1M HCl in ether to a DCM solution of the amine and removal of the solvent under reduced pressure.

EXAMPLE 259

N-[[1-(Dimethylamino)cyclopentyl](phenyl)methyl]-2-(methylthio-4,6-bis(trifluoromethyl)benzamide
Chiral

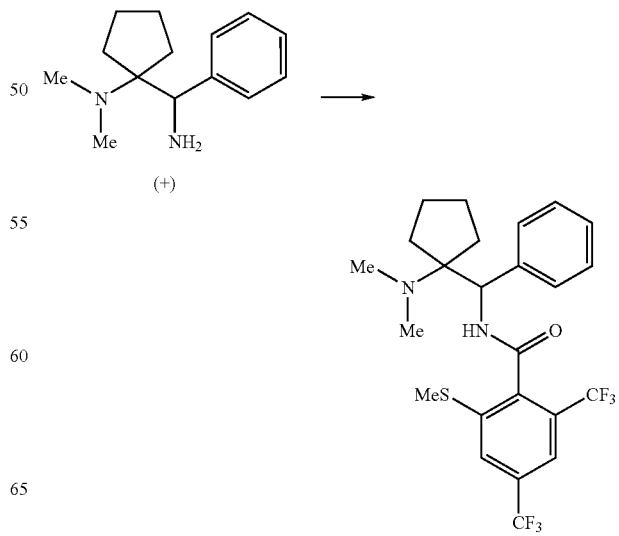

A mixture of 2-(methylthio)-4,6-bis(trifluoromethyl)benzoyl chloride and methyl 2,4-bis(trifluoromethyl)benzoate (112 mg) prepared as described in D55 was dissolved in dry DCM (2 ml) and treated with (+)-{1-[amino(phenyl)methyl]cyclopentyl}dimethylamine D3 enantiomer 2 (33 mg; 0.15 mmol) and triethylamine (42 ul, 0.30 mmol) and left overnight at room temperature. The volatile components were removed under reduced pressure and the residue chromatographed on silica gel. Elution with 0-80% ethyl acetate in pentane gave the title product as a crisp foam (60 mg; 86%). $^1$H NMR (CDCl$_3$) δ: 0.90 (1H, m), 1.4-1.9 (7H, overlapping m), 2.22 (6H, s), 2.52 (3H, s), 5.05 (1H, d, J=4.4 Hz), 7.22-7.5 (6H, overlapping m), 7.68 (1H, s), 7.71 (1H, s). Mass Spectrum (Electrospray LC/MS): Found 505 (MH$^+$) C$_{24}$H$_{26}$F$_6$N$_2$OS requires 504. Ret time 2.35 min.

The title product was converted to the hydrochloride salt (60 mg) by addition of excess 1M HCl in ether to a DCM solution of the amine and removal of the solvent under reduced pressure.

EXAMPLE 260

N-[[1-(Dimethylamino)cyclopentyl](phenyl)methyl]-2-methyl-4,6-bis(trifluoromethyl)benzamide Chiral

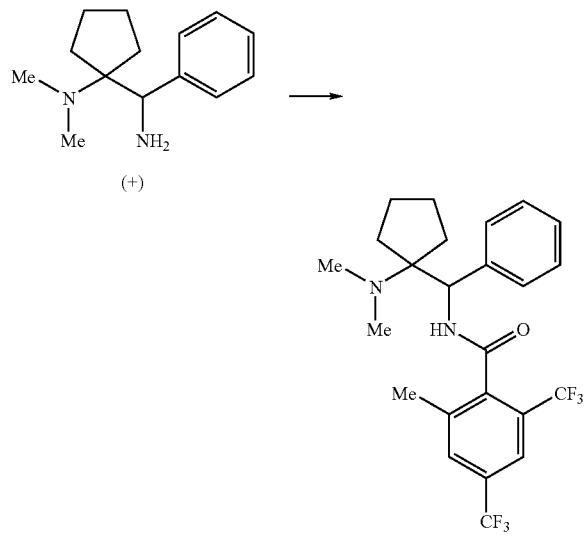

A mixture of 2-methyl-4,6-bis(trifluoromethyl)benzoyl chloride and methyl 2,4-bis(trifluoromethyl)benzoate (approximately 0.5 mmol) prepared as described in D53 was dissolved in dry DCM (3 ml) and treated with (+)-{1-[amino(phenyl)methyl]cyclopentyl}dimethylamine D3 enantiomer 2 (109 mg, 0.50 mmol) and triethylamine (140 ul, 1.00 mmol) and left overnight at room temperature. The volatile components were removed under reduced pressure and the residue chromatographed on silica gel. Elution with 0-80% ethyl acetate in pentane gave the title product (86 mg, ca.36%). $^1$H NMR (CDCl$_3$) δ: 0.95 (1H, br m), 1.44-1.86 (7H, overlapping m), 2.20 (6H, s), 2.41 (3H, br s), 5.10 (1H, d, J=5.6 Hz), 7.07 (1H, br s), 7.26-7.42 (5H, overlapping m), 7.67 (1H, s), 7.77 (1H, s). Mass Spectrum (Electrospray LC/MS): Found 473 (MH$^+$) C$_{24}$H$_{26}$F$_6$N$_2$O requires 472. Ret time 2.25 min.

The title product was converted to the hydrochloride salt (90 mg) by addition of excess 1M HCl in ether to a chloroform solution of the amine and removal of the solvent under reduced pressure.

The compounds of the Examples above could be converted to their corresponding hydrochloride salts by dissolving the parent free base in DCM or DCM/methanol mixtures and adding 1M hydrogen chloride in ether, followed by evaporation and drying in vacuo. Compounds purified by Mass Directed Auto-Purification were isolated as the formate salt which could be converted to the free base via an SCX column and to the corresponding hydrochloride salt by reaction with 1M hydrogen chloride in ether as described above.

The invention claimed is:

1. A composition of matter comprising 2-(methyloxy)-N-[2-methyl-1-phenyl-2-(1-pyrrolidinyl)propyl]-4,6-bis(trifluoromethyl)benzamide as a racemic mixture, or a stereoisomer thereof; or a salt thereof.

2. The composition of claim 1 wherein the salt form is a pharmaceutically acceptable salt.

3. The composition of claim 1 comprising 2-(methyloxy)-N-[2-methyl-1-phenyl-2-(1-pyrrolidinyl)propyl]-4,6-bis(trifluoromethyl)benzamide as a racemic mixture, or a stereoisomer thereof.

4. The composition of claim 1 comprising the hydrochloride salt form of 2-(methyloxy)-N-[2-methyl-1-phenyl-2-(1-pyrrolidinyl)propyl]-4,6-bis(trifluoromethyl)benzamide as a racemic mixture, or a stereoisomer thereof.

5. A method of treating schizophrenia in a patient comprising administering to a patient in need thereof an effective amound of the composition of matter according to claim 1 or a pharmaceutically acceptable salt thereof, either neat, or admixed with a pharmaceutically acceptable carrier.

6. The method of treating schizophrenia in a patient according to claim 5 wherein the composition of matter comprises the hydrochloride salt form of 2-(methyloxy)-N-[2-methyl-1-phenyl-2-(1-pyrrolidinyl)propyl]-4,6-bis(trifluoromethyl)benzamide as a racemic mixture, or a stereoisomer thereof; either neat, or admixed with a pharmaceutically acceptable carrier.

7. The method of treating schizophrenia according to claim 5 wherein the composition of matter comprises 2-(methyloxy)-N-[2-methyl-1-phenyl-2-(1-pyrrolidinyl)propyl]-4,6-bis(trifluoromethyl)benzamide as a racemic mixture, or a stereoisomer thereof; either neat, or admixed with a pharmaceutically acceptable carrier.

8. A pharmaceutical composition comprising a composition of matter comprising 2-(methyloxy)-N-[2-methyl-1-phenyl-2-(1-pyrrolidinyl)propyl]-4,6-bis(trifluoromethyl)benzamide as a racemic mixture, or a stereoisomer thereof, or a pharmaceutically acceptable salt thereof and a pharmaceutically acceptable excipient.

9. The pharmaceutical composition of claim 8 wherein the composition of matter comprises 2-(methyloxy)-N-[2-methyl-1-phenyl-2-(1-pyrrolidinyl)propyl]-4,6-bis(trifluoromethyl)benzamide as a racemic mixture, or a stereoisomer thereof; and a pharmaceutically acceptable excipient.

10. The pharmaceutical composition of claim 8 wherein the composition of matter composition of matter comprises the hydrochloride salt form of 2-(methyloxy)-N-[2-methyl-1-phenyl-2-(1-pyrrolidinyl)propyl]-4,6-bis(trifluoromethyl)benzamide as a racemic mixture, or a stereoisomer thereof; and a pharmaceutically acceptable excipient.

11. A composition of matter comprising a chirally enriched enantiomer of 2-(methyloxy)-N-[2-methyl-1-phenyl-2-(1-pyrrolidinyl)propyl]-4,6-bis(trifluoromethyl)benzamide, or a salt thereof.

12. The composition of claim 11 comprising a chirally enriched enantiomer of a pharmaceutically acceptable salt form of 2-(methyloxy)-N-[2-methyl-1-phenyl-2-(1-pyrrolidinyl)propyl]-4,6-bis(trifluoromethyl)benzamide.

13. The composition of claim 12 comprising a chirally enriched enantiomer of the hydrochloride salt form of 2-(methyloxy)-N-[2-methyl-1-phenyl-2-(1-pyrrolidinyl)propyl]-4,6-bis(trifluoromethyl)benzamide.

* * * * *